(12) United States Patent
Klaveness et al.

(10) Patent No.: US 9,585,880 B2
(45) Date of Patent: Mar. 7, 2017

(54) CYCLIC AMINO COMPOUNDS FOR USE IN THE TREATMENT OF CARDIAC DISORDERS

(71) Applicant: Universitetet I Oslo, Blindern (NO)

(72) Inventors: Jo Klaveness, Oslo (NO); Kjetil Tasken, Rykkinn (NO)

(73) Assignee: Universitetet I Oslo, Blindern (NO)

( * ) Notice: Subject to any disclaimer, the term of this patent is extended or adjusted under 35 U.S.C. 154(b) by 45 days.

(21) Appl. No.: 14/549,414

(22) Filed: Nov. 20, 2014

(65) Prior Publication Data

US 2015/0141456 A1    May 21, 2015

(30) Foreign Application Priority Data

Nov. 20, 2013 (GB) .................... 1320506.7

(51) Int. Cl.
| | | |
|---|---|---|
| A61K 31/44 | (2006.01) | |
| A61K 31/472 | (2006.01) | |
| A61K 31/4035 | (2006.01) | |
| A61K 31/4439 | (2006.01) | |

(52) U.S. Cl.
CPC ........ *A61K 31/472* (2013.01); *A61K 31/4035* (2013.01); *A61K 31/4439* (2013.01)

(58) Field of Classification Search
CPC .................................................. C07D 471/10
USPC ....................................................... 514/278
See application file for complete search history.

(56) References Cited

U.S. PATENT DOCUMENTS

| | | |
|---|---|---|
| 6,107,104 A | 8/2000 | Lockerbie et al. |
| 6,723,743 B1 | 4/2004 | Thurkauf et al. |
| 6,958,214 B2 | 10/2005 | Braun |
| 7,432,342 B2 | 10/2008 | Braun et al. |
| 2005/0282814 A1 | 12/2005 | Wrasidlo et al. |
| 2006/0154330 A1 | 7/2006 | Klussmann et al. |
| 2009/0104177 A1 | 4/2009 | Klussmann et al. |
| 2011/0158905 A1 | 6/2011 | Goldenberg et al. |

FOREIGN PATENT DOCUMENTS

| | | |
|---|---|---|
| CN | 1865221 A | 11/2006 |
| DE | 2150293 A1 | 4/1973 |
| EP | 1777230 A1 | 4/2007 |
| EP | 2098226 A1 | 9/2009 |
| WO | WO0027852 A1 | 5/2000 |
| WO | WO03057673 A1 | 7/2003 |
| WO | WO2004081576 A2 | 9/2004 |
| WO | WO2006011043 A1 | 2/2006 |
| WO | WO2006032909 A2 | 3/2006 |
| WO | WO2006032923 A2 | 3/2006 |
| WO | WO2006122546 A1 | 11/2006 |
| WO | WO2007028969 A2 | 3/2007 |
| WO | WO2010073235 A1 | 7/2010 |
| WO | WO2012080762 A1 | 6/2012 |
| WO | WO2013171332 A2 | 11/2013 |

OTHER PUBLICATIONS

The International Search Report and Written Opinion mailed Feb. 25, 2014 in connection with International Application No. PCT/EP2013/060263.
Singh, Chingakham B. et al. "Aqueous-Mediated N-Alkylation of Amines." Eur. J. Org. Chem. 2007, pp. 1369-1377.
"XP002719557." Database Registry, Chemical Abstracts Service, Colombus, Ohio, U.S., Aug. 3, 2005.
"XP002719558." Database Registry, Chemical Abstracts Service, Colombus, Ohio, U.S., Sep. 10, 2008.
"XP002719559." Database Registry, Chemical Abstracts Service, Colombus, Ohio, U.S., Sep. 10, 2008.

*Primary Examiner* — Raymond Henley, III
(74) *Attorney, Agent, or Firm* — Dorsey & Whitney LLP

(57) ABSTRACT

The present invention relates to tertiary amines of formula (I) for use in therapy, particularly for use in treating cardiovascular disorders. The compounds have been found to regulate phospholamban phosphorylation by interfering with the A-kinase anchor protein 18delta (AKAP18δ) binding to the PKA substrate phospholamban. The compounds share a tri(alkylaryl/alkylheteroaryl) amine structure.

21 Claims, 6 Drawing Sheets

Compound 2

Compound 3

Compound 4

Compound 5

Compound 6

Compound 7

Compound 8

Compound 9

CYCLIC AMINO COMPOUNDS FOR USE IN THE TREATMENT OF CARDIAC DISORDERS

TECHNICAL FIELD

The invention relates to new chemical compounds, new pharmaceutical compositions and use of these compounds and their compositions for treatment of cardiac disorders especially reperfusion syndrome following myocardial infarction and post-infarction chronic heart failure. The specific compounds interfere with the A-kinase anchor protein (AKAP) 18delta (AKAP18δ) binding to the PKA substrate phospholamban.

BACKGROUND

The A-kinase anchor proteins (AKAPs) are a group of structurally diverse proteins which have the common function of binding to the regulatory subunit of protein kinase A (PKA) and confining the PKA holoenzyme to discrete locations within the cell. There are at least 50 different AKAPs, all of which have been cloned. Typical AKAPs include for example AKAP79, AKAP18, AKAP450, all of which are somewhat arbitrarily named after their apparent mobility by SDS-poly acrylamide gel electrophoresis. Later, the gene nomenclature committee has also introduced a separate nomenclature for AKAPs where they are consecutively numbered AKAP1, AKAP2, AKAP3 etc. In addition, some AKAPs like ezrin and Opa1 have already been assigned other names that are in use.

KAPs act as targeting devices that assemble signaling elements on a scaffold (the AKAP) that itself targets to microdomains in cells. This allows specific targeting of substrates to be regulated by phosphorylation (by PKA) and dephosphorylation (by phosphatases). PKA binds via its regulatory subunits (RIα, RIIα, RIβ, RIIβ) directly to an amphipathic α-helix in the AKAP, which is a common feature of AKAPs. The AKAPs also bind other components including; phosphodiesterases (PDEs) which break down cAMP, phosphatases which dephosphorylate downstream PKA targets and also other kinases (PKC and MAPK). Some AKAPs are able to bind both regulatory subunits (RI & RII) of PKA and are dual-specific AKAPs (for example D-AKAP1, D-AKAP2, ezrin, OPA1).

For references related the various AKAPs and their biological functions see for example:

Tasken and Aandahl in Physiological Reviews volume 84, issue 1, page 137-167 (2004), Pidoux and Tasken in Journal of Molecular Endocrinology volume 44, issue 5, page 271-284 (2010), Feliciello et al in Journal of Molecular Biology, volume 308, issue 2, page 99-114 (2001), A. McCahill et al. in Cellular Signalling, volume 17, issue 9, page 1158-1173 (2005), L. Cardone et al. in Journal of Molecular Biology, volume 320, issue 3, page 663-675, A. M. Sardanelli et al. in FEBS Letters, volume 580, issue 24, page 5690-5696 (2006), B. Hu et al. in Biochemical and Biophysical Research Communications, volume 285, issue 5, page 1369-1376 (2001), S. Herrgaard et al. in FEBS Letters, volume 486, issue 2, page 107-111 (2000), B. Abrenica et al. in Journal of Molecular and Cellular Cardiology, volume 46, issue 5, 674-681 (2009), O. M. Seternes et al. in Cellular Signaling, volume 11, issue 3, page 211-219 (1999), K. Kurihara et al. in Biochemical Pharmacology, volume 66, issue 2, page 239-250 (2003), S. B. Moss et al. in Trends in Endocrinology & Metabolism, volume 12, issue 10, page 434-440 (2001), T. E. Lewis et al. in Urologic Oncology: Seminars and Original Investigations, volume 23, issue 6, page 407-412 (2005), F. W. Herberg et al. in Journal of Molecular Biology, volume 298, issue 2, page 329-339 (2000), C. R. Carlson et al. in Journal of Molecular Biology, volume 327, issue 3, page 609-618 (2003), R. B. Brown et al. in Biochemical and Biophysical Research Communications, volume 306, issue 2, page 394-401 (2003), T. Kurosu et al. in Brain Research, volume 1251, page 53-64 (2009), M. Hadad et al. in Mechanisms of Development, volume 128, issues 7-10, page 471-482 (2011), L. R. Johnson et al. in Development Biology, volume 192, issue 2, page 340-350 (1997), D. Diviani et al. in European Journal of Cell Biology, volume 85, issue 7, page 603-610 (2006), A. Feliciello et al. in Current Biology, volume 7, issue 12, page 1011-1014 (1997), G. K. Carnegie et al. in Molecular Cell, volume 15, issue 6, 889-899 (2004), A. Tamai et al. in International Congress Series, volume 1283, page 263-264 (2005), F. S. Kinderman et al. Molecular Cell, volume 24, issue 3, page 397-408 (2006), M. Colledge et al. in Neuron, volume 27, issue 1, page 107-119 (2000), Biochemical and Biophysical Research Communications, volume 225, issue 1, 313-319 ((1996), A. S. Cantrell et al. in Molecular and Cellular Neuroscience, volume 21, issue 1, page 63-80, K. Josefsen et al. in FEBS Letters, volume 584, issue 1, page 81-85 (2010), P. Klingbell et al. in Mechanisms of Development, volume 100, issue 2, page 323-326 (2001), G. K. Carnegie et al. in Molecular Cell, volume 32, issue 2, page 169-179 (2008), C. Riether et al. in Brain, Behavior, and Immunity, volume 25, issue 1, page 59-66 (2011), D. Diviani et al. in Current Biology, volume 10, issue 7, page 417-420 (2000), J. D. Scott et al in Handbook of Cell Signaling, volume 2, page 283-388 (2003), T-T Aye et al. in Journal of Molecular and Cellular Cardiology, volume 52, issue 2, 511-518 (2012), A. L. Bauman et al. in Neuropharmacology, volume 46, issue 3, page 299-310 (2004), J. D. Scott et al. in Handbook of Cell Signaling (Second Edition), page 1337-1347 (2010), M. G. Gold et al. in Molecular Cell, volume 24, issue 3, 383-395 (2006), A. Carrera et al. in Development Biology, volume 180, issue 1, page 284-296 (1996), M. L. Dell'Acqua el al. in European Journal of Cell Biology, volume 85, issue 7, page 627-633 (2006), N. W. Court et al. in Biochimica et Biophysica Acta (BBA)-Molecular Cell Research, volume 1744, issue 1, page 68-75 (2005)

There are a so far only a limited number of patent documents describing AKAPs. The most relevant documents are:

US2011/158905 (IBC Pharmaceuticals) describes a fusion protein comprising an 20 Nov. 2013 anchoring domain (AD) moiety or a dimerization and docking domain (DDD) moiety, wherein the AD moiety consists of the amino acid sequence of the AD moiety of an AKAP (A-kinase anchoring protein) and the DDD moiety consists of the amino acid sequence of the DDD moiety of a human protein kinase A regulatory subunit; and an effector moiety. The effector moiety is selected from the group consisting of an antibody, an antigen-binding antibody fragment, a cytokine, a viral antigen, a xenoantigen, an RNase, a heat shock protein, the N-A1 domain of CEACAM5, the A3-B3 domain of CEACAM5, alpha2-macroglobulin, HSA (human serum albumin), a human protamine, and Fc fragment of a human antibody and a nucleic acid binding protein. The proteins might be useful for treatment of various diseases or conditions selected from the group consisting of cancer, autoimmune disease, immune dysregulation disease, organ-graft rejection, graft-versus-host disease, a neurodegenerative disease, a metabolic disease and a cardiovascular disease.

U.S. Pat. No. 7,432,342 (Sequenom) relates to A-kinase anchor protein (AKAPs) muteins, peptides thereof, and nucleic acids encoding the peptides, especially a polypeptide that is a mutein of a D-AKAP2 polypeptide, wherein the mutein exhibits modified binding to a regulatory subunit of PKA compared to a native D-AKAP2.

EP2098226 (Forsungsverbund Berlin E.V.) describes use of bicyclic compounds (I) or their salts, solvates, hydrates or formulations for preparing a medicament for the prophylaxis or treatment of diseases associated with defect of compartmentalized cyclic adenosine monophosphate (cAMP)-dependent signal transduction, is claimed. Use of bicyclic compounds of formula (I) or their salts, solvates, hydrates or formulations for preparing a medicament for the prophylaxis or treatment of diseases associated with defect of compartmentalized cyclic adenosine monophosphate (cAMP)-dependent signal transduction, is claimed. Formula (X) describes a general bicyclic formula in EP2098226, while formula (I) describes biphenyl compounds which are the most preferred compounds.

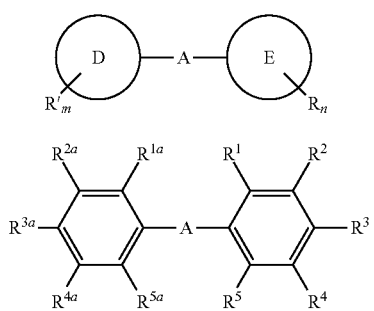

A: O, S, NH, CO, (hetero)alkyl, alkenyl, alkynyl, (hetero) aryl, cycloalkylene, (hetero)alkylcycloalkylene, heterocycloalkylene or (hetero)aralkylene group; R, R1: H, halo, $NH_2$, OH, $NO_2$, (hetero)alkyl, alkenyl, alkynyl (all preferred), SH, $N_3$, (hetero)aryl, (hetero)cycloalkyl, (hetero) alkylcycloalkyl or (hetero)aralkyl residue; D, E: (hetero) aryl, (hetero)cycloalkyl, (hetero)alkylcycloalkyl or (hetero) aralkyl (preferably substituted phenyl group); and m, n: 0-5 (preferably 1-3). The mechanism of action for these bicyclic compounds are protein kinease A and as AKAP interaction inhibitor. The indications for these agents are cardiovascular indications like hypertension and vasotropic activity.

WO2007/028969 (University of Oslo) relates to molecules which modify the binding between AKAP 18d and phosphodiesterase 4D or AKAP 18d and phospholamban and their use in altering PKA type II-mediated, activation of SERCA2 in a cell, for example to alleviate cardiovascular disease. Preferably such molecules include the motif RRASTIE. Molecules such as those which mimic binding of AKAP 18d to PKA, which allow enhanced phosphorylation of PLB are also discussed. No low-molecular weight compounds are specifically mentioned in this document.

WO2006/122546 describes non-peptide protein kinase A/protein kinase A anchor protein decouplers or disruptors. The compounds are listed in extensive tables of compounds. The chemical structures are structurally diverse and cannot be represented in any general formula. The compounds disclosed in these tables do not fall within the general formula of compounds of the present invention. The potential indications for use of these compounds are very broad including an extensive listing of very many different diseases, disorders and conditions.

WO2006/154330 (Forsungsverbund Berlin E.V.) relates to a nucleic acid sequence encoding a protein kinase A anchor protein, to the use of said nucleic acid sequence in a fusion protein, to a method of determining the interaction of said protein kinase A anchor protein with regulatory subunits of protein kinase A, and to a method of identifying cell-permeable substances.

WO2006/032923 (University of Oslo) describes a PKA I anchoring disrupting molecule or AKAP mimic, wherein said molecule or mimic is a polypeptide which comprises the following amino acid sequence: X1 X2 X3 Y A X4 X5 L A X6 X7 X8 I X9 X10 X11 X12 X13 (sequence (1)) or a peptidomimetic or analogue thereof is provided. Also provided are antibodies to the molecule, nucleic acid molecules comprising a sequence encoding the molecule and pharmaceutical compositions. A method of altering the PKA type I signaling pathway in a cell by administration of the anchoring disruption molecule or AKAP mimic, in particular to treat immunosuppressive disorders, proliferative diseases or autoimmune diseases is also described.

WO2006/032909 (University of Oslo) describes a PKA II anchoring disruption molecule or AKAP mimic, wherein said molecule or mimic is a polypeptide which comprises the following amino acid sequence: X1 X2 E X3 X4 A K Q I V X5 X6 X7 I X8 X9 X10 (sequence (1)) or a peptidomimetic or analogue thereof is provided. Also provided are antibodies to the molecule, nucleic acid molecules comprising a sequence encoding the molecule and pharmaceutical compositions. A method of altering the PKA type II signaling pathway in a cell by administration of the anchoring disruption molecule or AKAP mimic, in particular to treat cardiovascular and metabolic disorders is also described.

US2009/104177 (Forsungsverbund Berlin E.V.) relates to a nucleic acid sequence encoding peptides which inhibit the interaction of protein kinase A (PKA) and protein kinase A anchor proteins (AKAP), to a host organism comprising said nucleic acid sequence and optionally expressing said peptides, to the use of said peptides and of said host organism in investigating diseases associated with said AKAP-PKA interaction, and to the use of said peptides as pharmaceutical agent for the treatment of such diseases.

U.S. Pat. No. 6,958,214 (Sequenom) relates to polymorphic A-kinase anchor proteins (AKAPs) and nucleic acids encoding the proteins are provided herein. Methods of detecting polymorphic AKAPs and nucleic acids encoding the AKAPs, and kits for use in the detection methods are also provided. Further provided herein are methods of identifying subjects having or at risk of developing disorders of signal transduction. Methods of determining susceptibility to morbidity and/or increased or early mortality are also described.

WO2004/081576 (Sequenom) relates to polymorphic A-kinase anchor proteins (AKAPs) and nucleic acids encoding the proteins are provided herein. Methods of detecting polymorphic AKAPs and nucleic acids encoding the AKAPs, and kits for use in the detection methods are also provided. Further provided herein are methods of identifying subjects having or at risk of developing diseases or disorders, such as those related to signal transduction and/or cardiovascular disease. Methods of determining susceptibility to morbidity and/or increased or early mortality are also described.

U.S. Pat. No. 6,107,104 (ICOS) relates to compositions and methods useful for isolating calcineurin as well as inhibiting calcineurin activity. The compositions are peptides that contain regions that are homologous to calcineurin-binding regions of Akap79. Also provided are methods for determining if a cell contains a calcineurin-binding and PKA-binding anchoring protein that are useful for identifying additional proteins that bind both calcineurin and PKA. Another aspect of the present invention is methods for enhancing expression of interleukin 2 by T cells. Further provided are methods to identify proteins which interact with AKAP79, and methods to identify inhibitors of AKAP 79 interaction with other proteins.

PCT/EP2013/060263 (WO2013/171332) discloses trialkyl(hetero)aryl amines which interfere with the ability of the A-kinase anchor protein (AKAP) 18δ to bind to the PKA substrate phospholamban. The compounds find use in treatment of cardiac disorders, especially cardiac failure.

SUMMARY

The present invention relates to new chemical compounds, new pharmaceutical compositions and use of compounds and their compositions for treatment of cardiac disorders, especially cardiac failure. The compounds interfere with the ability of the A-kinase anchor protein (AKAP) 18δ to bind to the PKA substrate phospholamban and by disrupting this interaction specifically inhibit PKA phosphorylation of phospholamban upon adrenergic stimulation.

DETAILED DESCRIPTION

Figure 1:
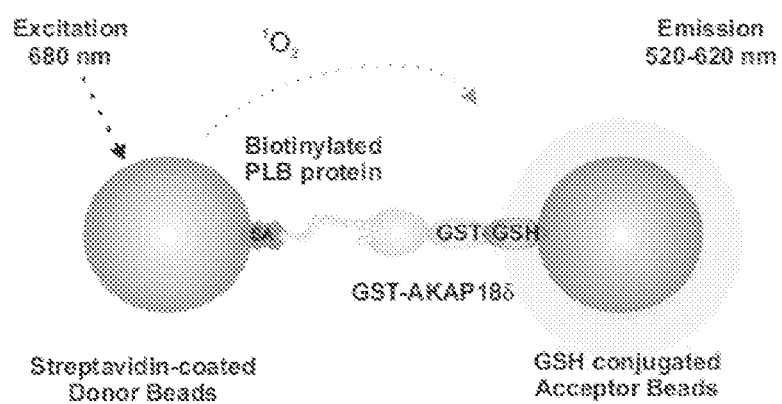
FIG. 1A is a schematic diagram showing a GST-AKAP18δ: PLB-biotin interaction assay by AlphaScreen.
FIG. 1B is a plot showing cross-titration of preparations of GST-AKAP18δ and biotinylated PLB.
Figure 1:
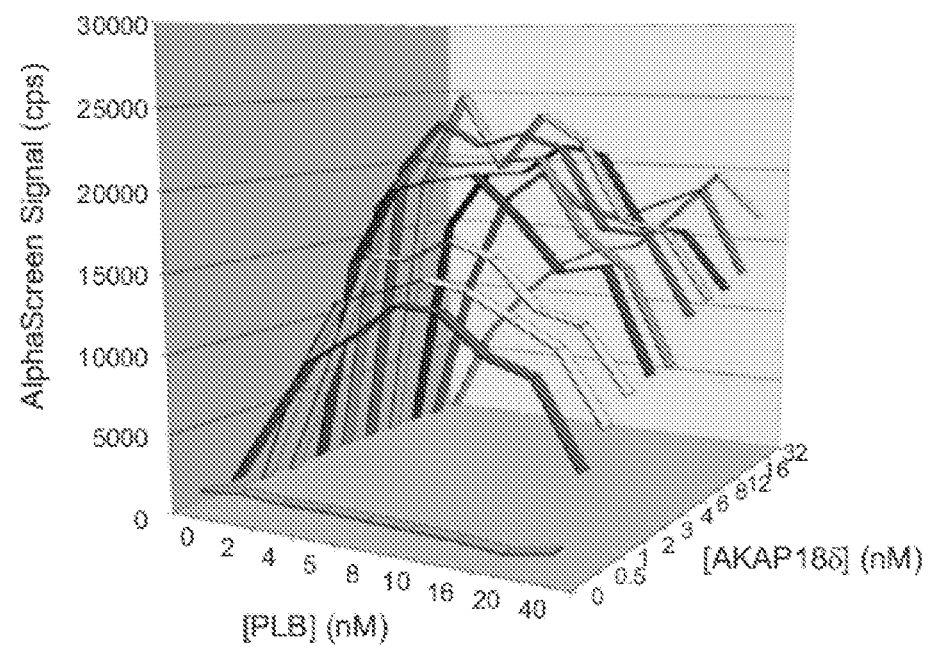
Figure 2A:
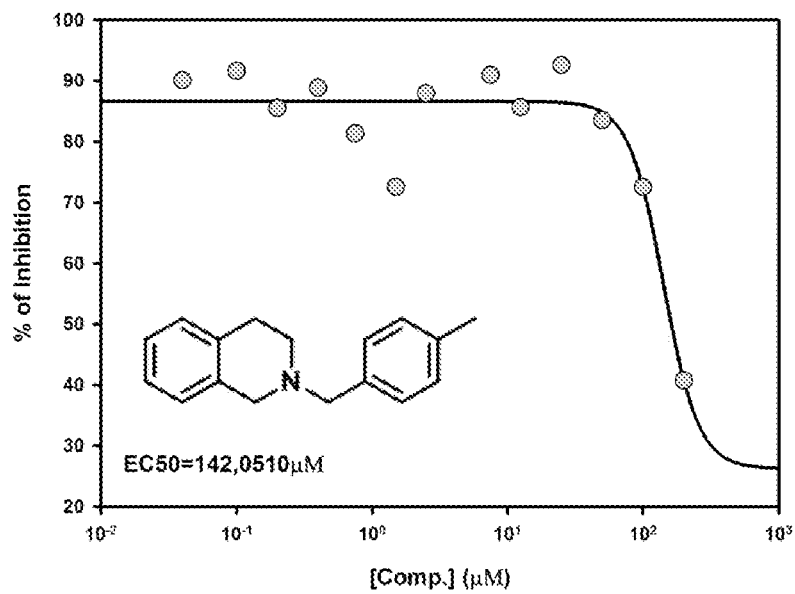
FIGS. 2a-2i are concentration-response curves of compounds of the invention in the AKAP18δ-PLB AlphaScreen assay, further wherein the x-axis is logarithmic.
Figure 2B:
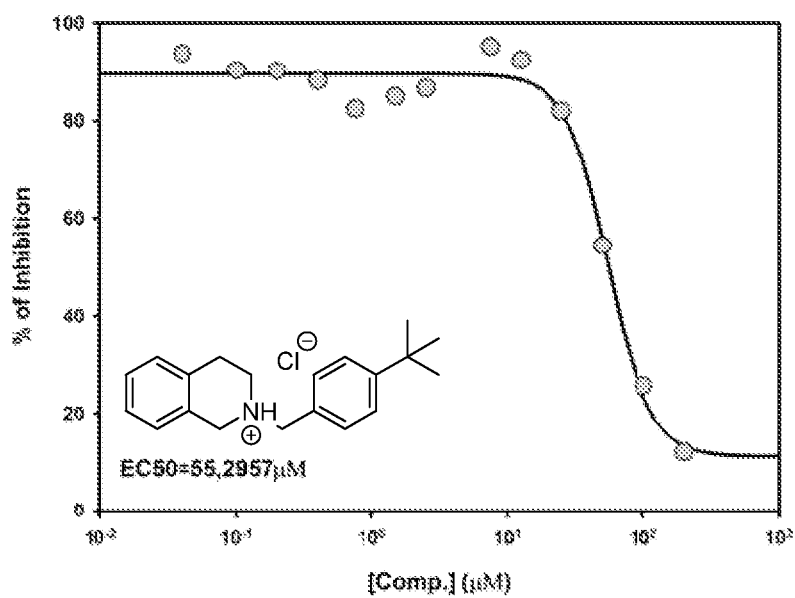
Figure 2C:
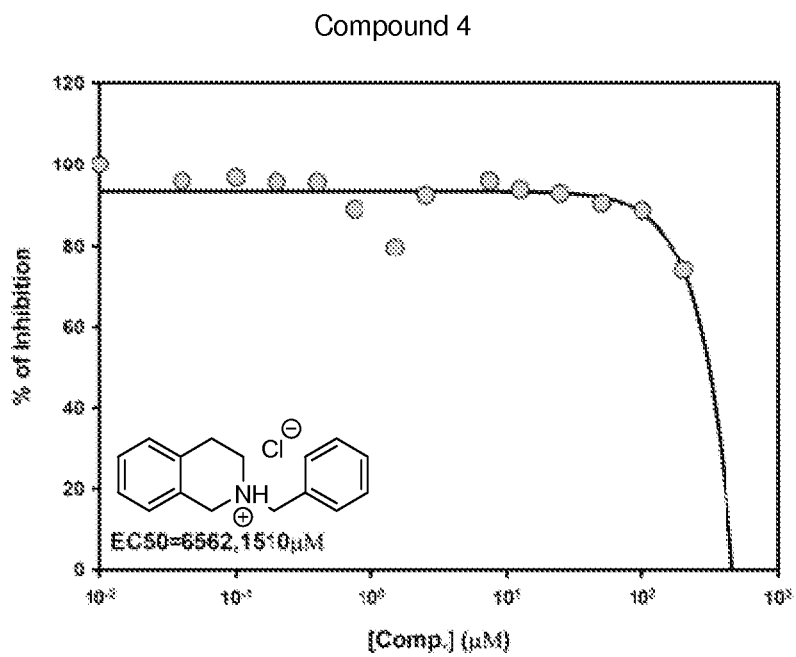
Figure 2D:
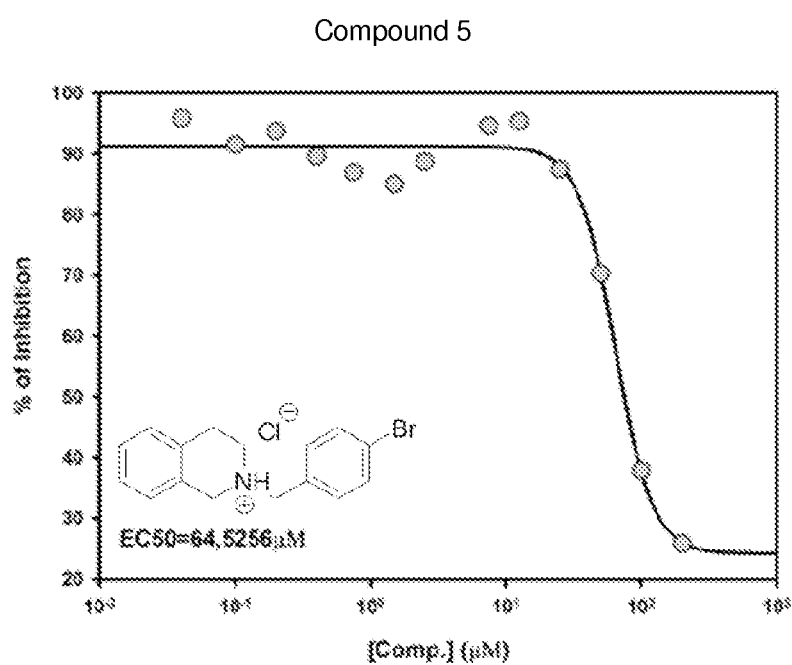
Figure 2E:
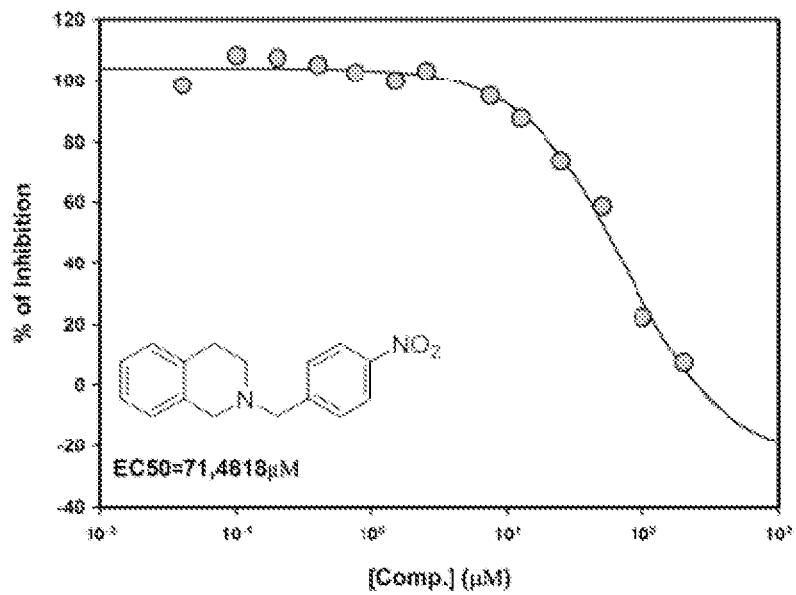
Figure 2F:
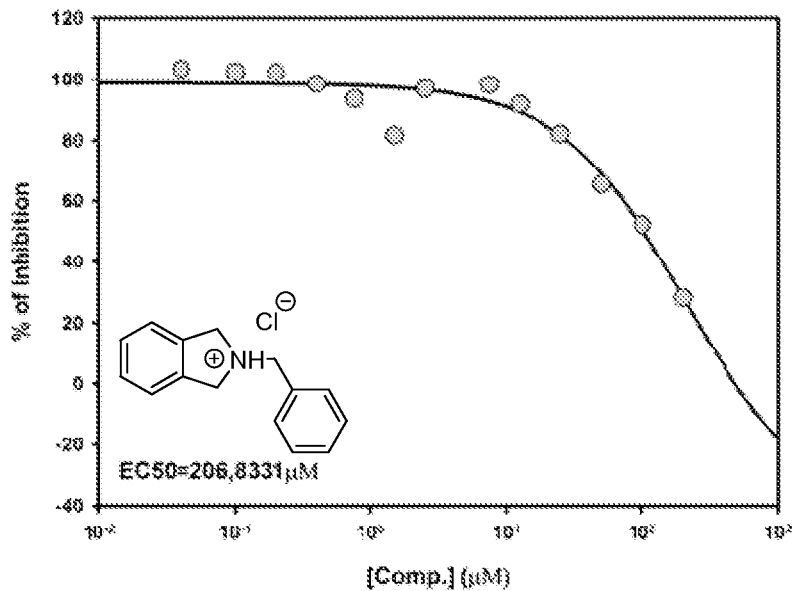
Figure 2G:
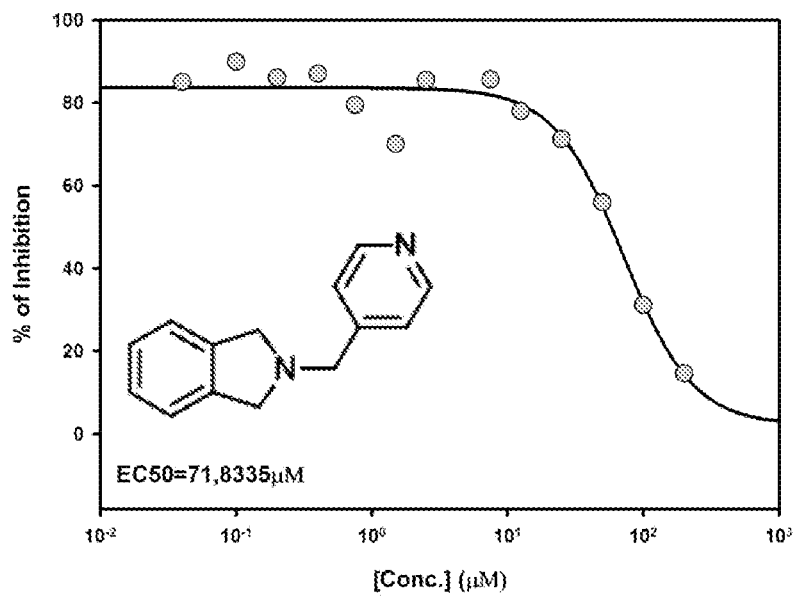
Figure 2H:
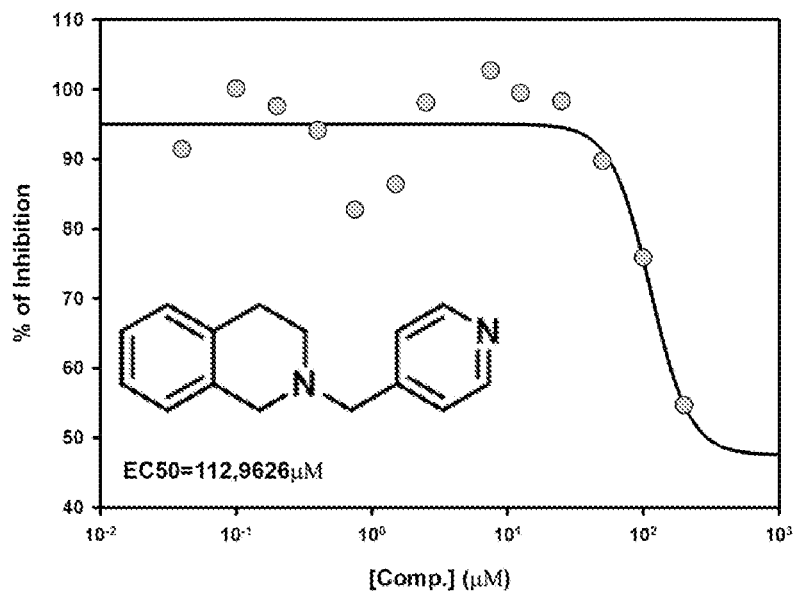
Figure 2I:
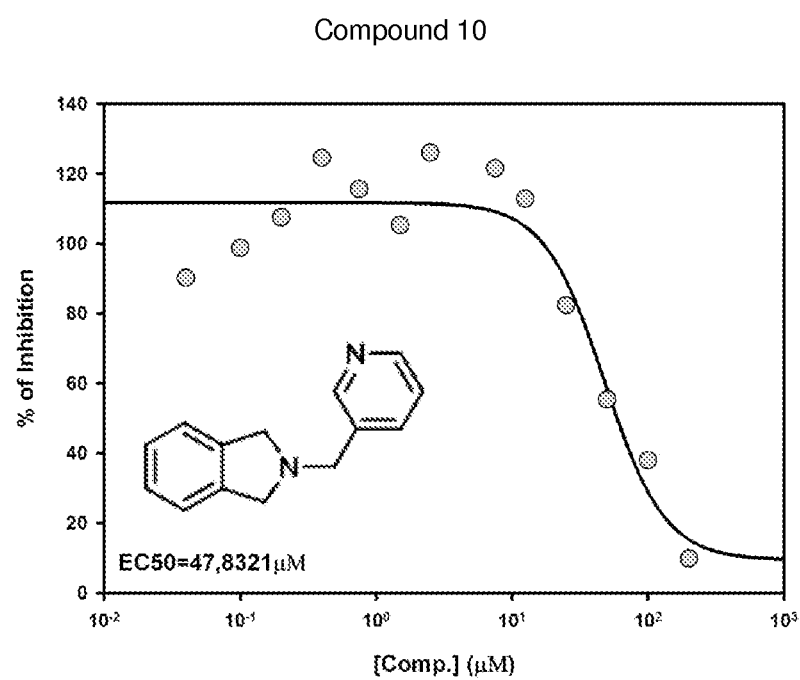

One aspect of the present invention relates to specific compounds interfering with A-kinase anchor proteins.

Thus, the present invention relates to a compound of formula (I), or a pharmaceutically acceptable salt thereof, including all stereoisomers and tautomers thereof, for use in therapy:

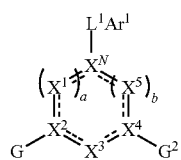

(I)

wherein
$X^N$ denotes N;
$L^1$ denotes $C(=O)C_1$-$C_3$-alkylene optionally substituted with one phenyl, or $C_1$-$C_4$-alkylene optionally substituted with one phenyl;
$G^2$ denotes H or $L^2Ar^2$;
$L^2$ denotes a bond or $C_1$-$C_3$-alkylene optionally substituted with one phenyl;
$X^1$ denotes CH or $CH_2$;
a and b independently denote 0 or 1;
$X^2G$ denotes C=O, C-$L^3$-$Ar^3$, CH-$L^3$-$Ar^3$ or

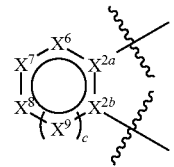

in which $X^{2a}$—$X^{2b}$ correspond to $X^2$ in the structure of formula (I);
c is 0 or 1;
$X^{2a}$, $X^{2b}$, $X^6$, $X^7$, $X^8$, and $X^9$ together form a 5-6 membered heteroaryl optionally substituted with —C(=O)Z or one or more R; or a 6 membered aryl optionally substituted with one or more R;
$L^3$ denotes a bond or $C_1$-$C_3$-alkylene optionally substituted with one phenyl;
$X^3$ denotes a bond, $Y^1$, $Y^1$—$Y^2$, $Y^1$—$Y^3$—$Y^2$, or

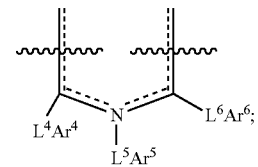

$L^4$ and $L^6$ independently denote a bond or $C_1$-$C_3$-alkylene optionally substituted with one phenyl;
$L^5$ denotes $C(=O)C_1$-$C_3$-alkylene optionally substituted with one phenyl, or $C_1$-$C_4$-alkylene optionally substituted with one phenyl;
$Y^1$, $Y^2$ and $Y^3$ independently denote CH, $CH_2$, N, $NZ^x$ or O, provided that when one of $Y^1$, $Y^2$ or $Y^3$ denotes O, the remainder denote CH, $CH_2$ or N;
$Z^x$ denotes H, $C_1$-$C_4$-alkyl, C(=O)H, C(=O)$C_1$-$C_4$-alkyl, or C(=O)O$R_z$;
$X^4$ denotes C, CH or N;
$X^5$ denotes CH or $CH_2$;
provided that $X^N$, $X^1$, $X^2$, $X^3$, $X^4$, $X^5$ together denote a 5-6 membered heterocycle or 5-6 membered heteroaryl;
$Ar^1$, $Ar^2$, $Ar^3$, $Ar^4$, $Ar^5$ and $Ar^6$ independently denote a 5-10 membered heteroaryl optionally substituted with —C(=O)Z or one or more R; or a 6-10 membered aryl optionally substituted with one or more R;
Z denotes $OR^a$ or $NR^bR^c$;
$R^a$ denotes H, $C_1$-$C_4$-alkyl, $C_3$-$C_6$-cycloalkyl, $C_2$-$C_4$-alkylene-O—$C_1$-$C_4$-alkyl, $C_2$-$C_4$-alkylene-CN; $C_1$-$C_4$-alkyl substituted with one or two $Ar^7$;
$R^b$ denotes H, $C_1$-$C_4$-alkyl, $C_3$-$C_6$-cycloalkyl, $C_2$-$C_4$-alkylene-CN; $C_2$-$C_4$-alkylene-O—$C_1$-$C_4$-alkyl; or $C_1$-$C_4$-alkyl substituted with one or two $Ar^7$;
$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

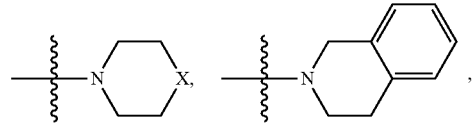

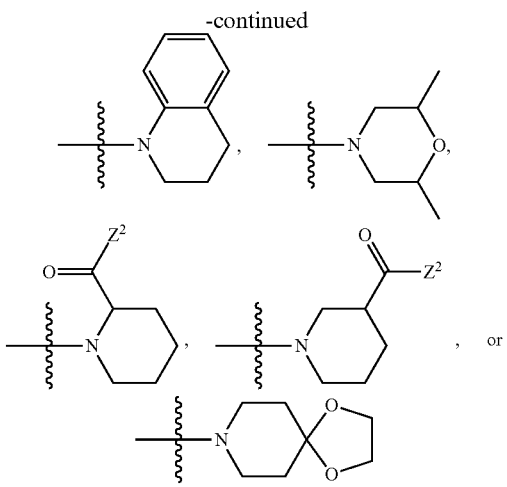

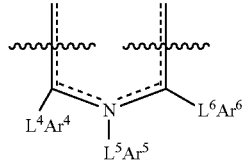

a and b must both be zero, otherwise the central ring formed by $X^N$, $X^1$, $X^2$, $X^3$, $X^4$ and $X^5$ will contain more than 6 atoms.

The present invention preferably relates to a compound of formula (Ia), or a pharmaceutically acceptable salt thereof, including all stereoisomers and tautomers thereof, for use in therapy:

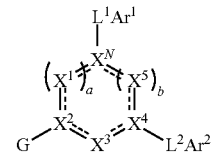

(Ia)

wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_3$-$C_6$-cycloalkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H, $C_1$-$C_4$-alkyl or $C_3$-$C_6$-cycloalkyl;

R independently denotes F, Cl, Br, I, $C_1$-$C_4$-haloalkyl, $OR^1$, $SR^1$, $NO_2$, $NR^2R^3$, $R^4$, C(=O)Y, $SO_3H$, $C_1$-$C_4$-alkyl, $C_1$-$C_4$-alkyl-phenyl, a 5-membered heteroaryl; or a phenyl substituted with a 5-membered heteroaryl;

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl; or $NR^2R^3$ denotes —NHC(=O)—$NHAr^8$; or together two adjacent $NR^2R^3$ groups denote —$NR^2$—CH=N— or —$NR^2$—$CH_2$—$NR^2$—; or together with an adjacent $OR^1$ group, $NR^2R^3$ denotes —$NR^2$—$CH_2$—O— or —N=CH—O—; or together with an adjacent $SR^1$ group, $NR^2R^3$ denotes —$NR^2$—$CH_2$—S— or —N=CH—S—;

$Ar^8$ denotes phenyl optionally substituted with $R^h$;

$R^h$ denotes halogen or $C_1$-$C_4$ alkyl;

$R^4$ denotes $C_1$-$C_4$-alkyl; or together with an adjacent $OR^1$ group, $R^4$ denotes —$CH_2CH_2$—O—; or together two adjacent $R^4$ groups denote —(CH)$_4$— or —(CH$_2$)$_4$—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

The compounds of formula (I) contain a central 5-6 membered, nitrogen-containing heterocycle or heteroaryl, which is bonded to two or three aryl or heteroaryl rings. It is to be understood that the requirement that the central ring contains 5-6 members places implicit limitations on the variables a, b and $X^3$. Thus, when $X^3$ denotes:

wherein $X^N$ denotes N;

$L^1$ denotes C(=O)$C_1$-$C_3$-alkylene optionally substituted with one phenyl, or $C_1$-$C_4$-alkylene optionally substituted with one phenyl;

$L^2$ denotes a bond or $C_1$-$C_3$-alkylene optionally substituted with one phenyl;

$X^1$ denotes CH or $CH_2$;

a and b independently denote 0 or 1;

$X^2G$ denotes C=O, C-$L^3$-$Ar^3$, CH-$L^3$-$Ar^3$ or

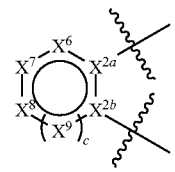

in which $X^{2a}$—$X^{2b}$ correspond to $X^2$ in the structure of formula (Ia);

c is 0 or 1;

$X^{2a}$, $X^{2b}$, $X^6$, $X^7$, $X^8$, and $X^9$ together form a 5-6 membered heteroaryl optionally substituted with —C(=O)Z or one or more R; or a 6 membered aryl optionally substituted with one or more R;

$L^3$ denotes a bond or $C_1$-$C_3$-alkylene optionally substituted with one phenyl;

$X^3$ denotes a bond, $Y^1$, $Y^1$—$Y^2$, $Y^1$—$Y^3$—$Y^2$, or

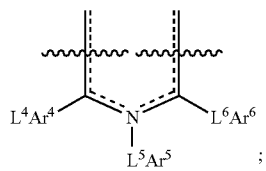

$L^4$ and $L^6$ independently denote a bond or $C_1$-$C_3$-alkylene optionally substituted with one phenyl;

$L^5$ denotes $C(=O)C_1$-$C_3$-alkylene optionally substituted with one phenyl, or $C_1$-$C_4$-alkylene optionally substituted with one phenyl;

$Y^1$, $Y^2$ and $Y^3$ independently denote CH, $CH_2$, N, $NZ^x$ or O, provided that when one of $Y^1$, $Y^2$ or $Y^3$ denotes O, the remainder denote CH, $CH_2$ or N;

$Z^x$ denotes H, $C_1$-$C_4$-alkyl, $C(=O)H$, $C(=O)C_1$-$C_4$-alkyl, or $C(=O)OR_z$;

$X^4$ denotes C, CH or N;

$X^5$ denotes CH or $CH_2$;

provided that $X^N$, $X^1$, $X^2$, $X^3$, $X^4$, $X^5$ together denote a 5-6 membered heterocycle or 5-6 membered heteroaryl;

$Ar^1$, $Ar^2$, $Ar^3$, $Ar^4$, $Ar^5$ and $Ar^6$ independently denote a 5-10 membered heteroaryl optionally substituted with —$C(=O)Z$ or one or more R; or a 6-10 membered aryl optionally substituted with one or more R;

Z denotes $OR^a$ or $NR^bR^c$;

$R^a$ denotes H, $C_1$-$C_4$-alkyl, $C_3$-$C_6$-cycloalkyl, $C_2$-$C_4$-alkylene-O—$C_1$-$C_4$-alkyl, $C_2$-$C_4$-alkylene-CN; $C_1$-$C_4$-alkyl substituted with one or two $Ar^7$;

$R^b$ denotes H, $C_1$-$C_4$-alkyl, $C_3$-$C_6$-cycloalkyl, $C_2$-$C_4$-alkylene-CN; $C_2$-$C_4$-alkylene-O—$C_1$-$C_4$-alkyl; or $C_1$-$C_4$-alkyl substituted with one or two $Ar^7$;

$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes wherein X denotes $CHZ^1$, O, or $NZ^1$;

$Z^1$ denotes H, $C(=O)H$, $C(=O)C_1$-$C_4$-alkyl, $C(=O)OR^z$, $Ar^7$, $C_1$-$C_4$-alkyl, $C_3$-$C_6$-cycloalkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H, $C_1$-$C_4$-alkyl or $C_3$-$C_6$-cycloalkyl;

R independently denotes F, Cl, Br, I, $C_1$-$C_4$-haloalkyl, $OR^1$, $SR^1$, $NO_2$, $NR^2R^3$, $R^4$, $C(=O)Y$, $SO_3H$, $C_1$-$C_4$-alkyl, $C_1$-$C_4$-alkyl-phenyl, a 5-membered heteroaryl; or a phenyl substituted with a 5-membered heteroaryl;

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl; or $NR^2R^3$ denotes —$NHC(=O)$—$NHAr^8$; or together two adjacent $NR^2R^3$ groups denote —$NR^2$—CH—N— or —$NR^2$—$CH_2$—$NR^2$—; or together with an adjacent $OR^1$ group, $NR^2R^3$ denotes —$NR^2$—$CH_2$—O— or —N—CH—O—; or together with an adjacent $SR^1$ group, $NR^2R^3$ denotes —$NR^2$—$CH_2$—S— or —N—CH—S—;

$Ar^8$ denotes phenyl optionally substituted with $R^h$;

$R^h$ denotes halogen or $C_1$-$C_4$ alkyl;

$R^4$ denotes $C_1$-$C_4$-alkyl; or together with an adjacent $OR^1$ group, $R^4$ denotes —$CH_2CH_2$—O—; or together two adjacent $R^4$ groups denote —$(CH)_4$— or —$(CH_2)_4$—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

Preferably, the present invention relates to a compound of formula (Ib), or a pharmaceutically acceptable salt thereof, including all stereoisomers and tautomers thereof, for use in therapy, (Ib)

wherein $X^N$ denotes N;

$L^1$ denotes $C(=O)C_1$-$C_3$-alkylene optionally substituted with one phenyl, or $C_1$-$C_4$-alkylene optionally substituted with one phenyl;

$L^2$ denotes a bond or $C_1$-$C_3$-alkylene optionally substituted with one phenyl;

$X^1$ denotes CH or $CH_2$;

a and b independently denote 0 or 1;

$X^2G$ denotes C=O, C-$L^3$-$Ar^3$, or in which $X^{2a}$—$X^{2b}$ correspond to $X^2$ in the structure of formula (Ib);

c is 0 or 1;

$X^{2a}$, $X^{2b}$, $X^6$, $X^7$, $X^8$, and $X^9$ together form a 5-6 membered heteroaryl optionally substituted with —$C(=O)Z$ or one or more R; or a 6 membered aryl optionally substituted with one or more R;

$L^3$ denotes a bond or $C_1$-$C_3$-alkylene optionally substituted with one phenyl;

$X^3$ denotes a bond, $Y^1$, $Y^1$—$Y^2$, $Y^1$—$Y^3$—$Y^2$, or

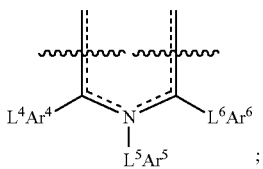

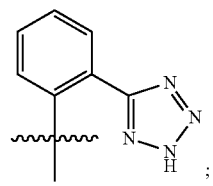 [SMILES: *c1ccccc1-c1nn[nH]n1]

$L^4$ and $L^6$ independently denote a bond or $C_1$-$C_3$-alkylene optionally substituted with one phenyl;

$L^5$ denotes $C(=O)C_1$-$C_3$-alkylene optionally substituted with one phenyl, or $C_1$-$C_4$-alkylene optionally substituted with one phenyl;

$Y^1$, $Y^2$ and $Y^3$ independently denote CH, $CH_2$, N, $NZ^x$ or O;

$Z^x$ denotes H, $C_1$-$C_4$-alkyl, $C(=O)H$, $C(=O)C_1$-$C_4$-alkyl, or $C(=O)OR_z$;

$X^4$ denotes C, CH or N;

$X^5$ denotes CH or $CH_2$;

provided that $X^N$, $X^1$, $X^2$, $X^3$, $X^4$, $X^5$ together denote a 5-6 membered heterocycle or 5-6 membered heteroaryl;

$Ar^1$, $Ar^2$, $Ar^3$, $Ar^4$, $Ar^5$ and $Ar^6$ independently denote a 5-10 membered heteroaryl optionally substituted with —C(=O)Z or one or more R; or a 6-10 membered aryl optionally substituted with one or more R;

Z denotes $OR^a$ or $NR^bR^c$;

$R^a$ denotes H or $C_1$-$C_4$-alkyl;

$R^b$ denotes H, $C_1$-$C_4$-alkyl, $C_2$-$C_4$-alkyl-CN; or $C_1$-$C_4$-alkyl substituted with one or two $Ar^7$;

$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

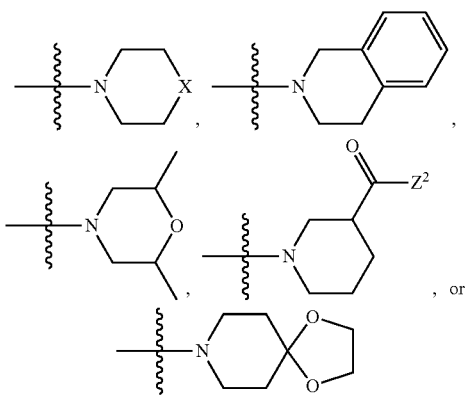

wherein X denotes $CHZ^1$, O, or $NZ^1$;

$Z^1$ denotes H, $C(=O)H$, $C(=O)C_1$-$C_4$-alkyl, $C(=O)OR^z$, $Ar^7$, $C_1$-$C_4$-alkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H or $C_1$-$C_4$-alkyl;

R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl, 5-tetrazolyl or $R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl;

$R^4$ denotes $C_1$-$C_4$-alkyl; or together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$-cycloalkyl.

In the compounds of formula (I) (or (Ia) or (Ib)), together $X^N$, $X^1$, $X^2$, $X^3$, $X^4$ and $X^5$ form a 5-6 membered heterocycle or 5-6 membered heteroaryl. Preferred embodiments include:

Embodiment 1 in which:

a and b denote 0;

$X^2G$ denotes C=O, C-$L^3$-$Ar^3$ or CH-$L^3$-$Ar^3$;

$X^3$ denotes $Y^1$—$Y^2$, or $Y^1$—$Y^3$—$Y^2$; and $X^4$ denotes C or CH.

Alternatively, embodiment 1a is identical to embodiment 1, except $Y^1$, $Y^2$, and $Y^3$ independently denote CH or $CH_2$.

Embodiment 2 in which:

a and b denote 0;

$X^2G$ denotes C-$L^3$-$Ar^3$ or CH-$L^3$-$Ar^3$;

$X^3$ denotes $Y^1$—$Y^2$, or $Y^1$—$Y^3$—$Y^2$; and $X^4$ denotes C or CH.

Alternatively, embodiment 2a is identical to embodiment 2, except $Y^1$, $Y^2$, and $Y^3$ independently denote CH or $CH_2$.

Embodiment 3 in which:

a and b denote 0;

$X^2G$ denotes C=O;

$X^3$ denotes $Y^1$—$Y^2$, or $Y^1$—$Y^3$—$Y^2$; and $X^4$ denotes C or CH.

Alternatively, embodiment 3a is identical to embodiment 3, except $Y^1$, $Y^2$, and $Y^3$ independently denote CH or $CH_2$.

Embodiment 4 in which:

a and b denote 0;

$L^1$ denotes $C_1$-$C_4$-alkylene optionally substituted with one phenyl;

$X^2G$ denotes CH-$L^3$-$Ar^3$;

$X^3$ denotes $Y^1$—$Y^2$ or $Y^1$—$Y^3$—$Y^2$;

$Y^1$, $Y^2$ and $Y^3$ independently denote $CH_2$, $NZ^x$ or O, provided that at least one of $Y^1$, $Y^2$ or $Y^3$ denotes $CH_2$ and that when one of $Y^1$, $Y^2$ or $Y^3$ denotes O, the remainder denote $CH_2$; and $X^4$ denotes CH.

Alternatively, embodiment 4a is identical to embodiment 4, except $Y^1$, $Y^2$ and $Y^3$ independently denote $CH_2$.

Embodiment 5 in which:

a and b denote 0;

$L^1$ denotes $C_1$-$C_4$-alkylene optionally substituted with one phenyl;

$X^2G$ denotes CH-$L^3$-$Ar^3$;

$X^3$ denotes $Y^1$—$Y^2$;

$Y^1$ and $Y^2$ independently denote $CH_2$, $NZ^x$ or O, provided that when one of $Y^1$ or $Y^2$ denotes O, the other denotes $CH_2$;

$X^4$ denotes CH.

Alternatively, embodiment 5a is identical to embodiment 5, except $Y^1$, $Y^2$ and $Y^3$ independently denote $CH_2$.

Embodiment 6 in which:

a and b denote 0;

$L^1$ denotes $C_1$-$C_4$-alkylene optionally substituted with one phenyl;

$X^2G$ denotes CH-$L^3$-$Ar^3$;

$X^3$ denotes $Y^1$—$Y^3$—$Y^2$;

$Y^1$, $Y^2$ and $Y^3$ independently denote $CH_2$, $NZ^x$ or O, provided that at least one of $Y^1$, $Y^2$ or $Y^3$ denotes $CH_2$ and that when one of $Y^1$, $Y^2$ or $Y^3$ denotes O, the remainder denote $CH_2$;

$X^4$ denotes CH.

Alternatively, embodiment 6a is identical to embodiment 6, except $Y^1$, $Y^2$ and $Y^3$ independently denote $CH_2$.

Embodiment 7 in which:

a and b denote 0;

$L^1$ denotes $C_1$-$C_4$-alkylene optionally substituted with one phenyl;

$X^2G$ denotes C=O;

$X^3$ denotes $Y^1$—$Y^2$ or $Y^1$—$Y^3$—$Y^2$;

$Y^1$, $Y^2$ and $Y^3$ independently denote $CH_2$, $NZ^x$ or O, provided that at least one of $Y^1$, $Y^2$ or $Y^3$ denotes $CH_2$ and that when one of $Y^1$, $Y^2$ or $Y^3$ denotes O, the remainder denote $CH_2$;

$X^4$ denotes CH.

Alternatively, embodiment 7a is identical to embodiment 7, except $Y^1$, $Y^2$ and $Y^3$ independently denote $CH_2$.

Embodiment 8 in which:

a and b denote 0;

$L^1$ denotes $C_1$-$C_4$-alkylene optionally substituted with one phenyl;

$X^2G$ denotes C=O;

$X^3$ denotes $Y^1$—$Y^2$;

$Y^1$ and $Y^2$ independently denote $CH_2$, $NZ^x$ or O, provided that when one of $Y^1$ or $Y^2$ denotes O, the other denotes $CH_2$;

$X^4$ denotes CH.

Alternatively, embodiment 8a is identical to embodiment 8, except $Y^1$, $Y^2$ and $Y^3$ independently denote $CH_2$.

Embodiment 9 in which:

a and b denote 0;

$L^1$ denotes $C_1$-$C_4$-alkylene optionally substituted with one phenyl;

$X^2G$ denotes C=O;

$X^3$ denotes $Y^1$—$Y^3$—$Y^2$;

$Y^1$, $Y^2$ and $Y^3$ independently denote $CH_2$, $NZ^x$ or O, provided that at least one of $Y^1$, $Y^2$ or $Y^3$ denotes $CH_2$ and that when one of $Y^1$, $Y^2$ or $Y^3$ denotes O, the remainder denote $CH_2$;

$X^4$ denotes CH.

Alternatively, embodiment 9a is identical to embodiment 9, except $Y^1$, $Y^2$ and $Y^3$ independently denote $CH_2$.

Embodiment 10 in which:

a and b denote 0;

$L^1$ denotes C(=O)$C_1$-$C_3$-alkylene optionally substituted with one phenyl;

$X^2G$ denotes CH-$L^3$-$Ar^3$;

$X^3$ denotes $Y^1$—$Y^2$ or $Y^1$—$Y^3$—$Y^2$;

$Y^1$, $Y^2$ and $Y^3$ independently denote $CH_2$, $NZ^x$ or O, provided that at least one of $Y^1$, $Y^2$ or $Y^3$ denotes $CH_2$ and that when one of $Y^1$, $Y^2$ or $Y^3$ denotes O, the remainder denote $CH_2$;

$X^4$ denotes CH.

Alternatively, embodiment 10a is identical to embodiment 10, except $Y^1$, $Y^2$ and $Y^3$ independently denote $CH_2$.

Embodiment 11 in which:

a and b denote 0;

$L^1$ denotes C(=O)$C_1$-$C_3$-alkylene optionally substituted with one phenyl;

$X^2G$ denotes CH-$L^3$-$Ar^3$;

$X^3$ denotes $Y^1$—$Y^2$;

$Y^1$ and $Y^2$ independently denote $CH_2$, $NZ^x$ or O, provided that when one of $Y^1$ or $Y^2$ denotes O, the other denotes $CH_2$;

$X^4$ denotes CH.

Alternatively, embodiment 11a is identical to embodiment 11, except $Y^1$, $Y^2$ and $Y^3$ independently denote $CH_2$.

Embodiment 12 in which:

a and b denote 0;

$L^1$ denotes C(=O)$C_1$-$C_3$-alkylene optionally substituted with one phenyl;

$X^2G$ denotes CH-$L^3$-$Ar^3$;

$X^3$ denotes $Y^1$—$Y^3$—$Y^2$;

$Y^1$, $Y^2$ and $Y^3$ independently denote $CH_2$, $NZ^x$ or O, provided at least one of $Y^1$, $Y^2$ or $Y^3$ denotes $CH_2$ and that when one of $Y^1$, $Y^2$ or $Y^3$ denotes O, the remainder denote $CH_2$;

X⁴ denotes CH.

Alternatively, embodiment 12a is identical to embodiment 12, except $Y^1$, $Y^2$ and $Y^3$ independently denote $CH_2$.

Embodiment 13 in which:
a and b denote 0;
$L^1$ denotes $C(=O)C_1$-$C_3$-alkylene optionally substituted with one phenyl, or $C_1$-$C_4$-alkylene optionally substituted with one phenyl;
$X^2G$ denotes C-$L^3$-$Ar^3$;
$X^3$ denotes $Y^1$—$Y^2$ or $Y^1$—$Y^3$—$Y^2$;
$Y^1$, $Y^2$ and $Y^3$ independently denote CH or N, provided that at least one of $Y^1$, $Y^2$ or $Y^3$ is CH;
$X^4$ denotes C.

Alternatively, embodiment 13a is identical to embodiment 13, except $Y^1$, $Y^2$ and $Y^3$ independently denote CH.

Embodiment 14 in which:
a and b denote 0;
$L^1$ denotes $C(=O)C_1$-$C_3$-alkylene optionally substituted with one phenyl, or $C_1$-$C_4$-alkylene optionally substituted with one phenyl;
$X^2G$ denotes C-$L^3$-$Ar^3$;
$X^3$ denotes $Y^1$—$Y^2$;
$Y^1$ and $Y^2$ independently denote CH or N;
$X^4$ denotes C.

Alternatively, embodiment 14a is identical to embodiment 14, except $Y^1$, $Y^2$ and $Y^3$ independently denote CH.

Embodiment 15 in which:
a and b denote 0;
$L^1$ denotes $C(=O)C_1$-$C_3$-alkylene optionally substituted with one phenyl, or $C_1$-$C_4$-alkylene optionally substituted with one phenyl;
$X^2G$ denotes C-$L^3$-$Ar^3$;
$X^3$ denotes $Y^1$—$Y^3$—$Y^2$;
$Y^1$, $Y^2$ and $Y^3$ independently denote CH or N, provided that at least one of $Y^1$, $Y^2$ or $Y^3$ is CH;
$X^4$ denotes C.

Alternatively, embodiment 15a is identical to embodiment 15, except $Y^1$, $Y^2$ and $Y^3$ independently denote CH.

Embodiment 16 in which:
a and b denote 0;
$X^2G$ denotes CH-$L^3$-$Ar^3$;
$X^3$ denotes

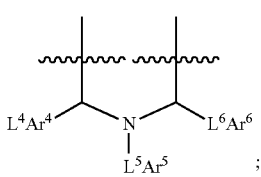

and
$X^4$ denotes CH.

Embodiment 17 in which:
a denotes 1;
$X^1$ denotes $CH_2$;
$X^2G$ denotes CH-$L^3$-$Ar^3$;
$X^3$ denotes $CH_2$;
$X^4$ denotes CH;
b denotes 0 or 1; and
$X^5$ denotes $CH_2$.

Embodiment 18 in which:
a denotes 1;
$X^1$ denotes $CH_2$;
$X^2G$ denotes

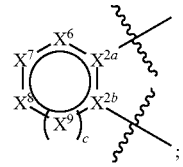

$X^3$ denotes $CH_2$;
$X^4$ denotes N; and
b denotes 0.

The present invention preferably relates to a compound of formula (Ic), or a pharmaceutically acceptable salt thereof, including all stereoisomers and tautomers thereof, for use in therapy:

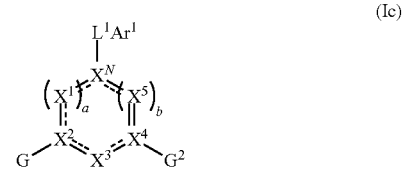

wherein
$X^N$ denotes N;
$L^1$ denotes $C(=O)C_1$-$C_3$-alkylene optionally substituted with one phenyl, or $C_1$-$C_4$-alkylene optionally substituted with one phenyl;
$G^2$ denotes H;
$X^1$ denotes $CH_2$;
a denotes 1;
b denotes 0;
$X^2G$ denotes

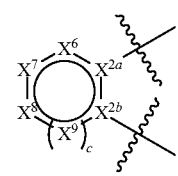

in which $X^{2a}$—$X^{2b}$ correspond to $X^2$ in the structure of formula (Ic);

c is 1;

$X^{2a}$, $X^{2b}$, $X^6$, $X^7$, $X^8$, and $X^9$ together form a 6 membered aryl optionally substituted with one or more R;

$X^3$ denotes a $CH_2$ or a bond;

$X^4$ denotes CH;

$Ar^1$ denotes a 5-10 membered heteroaryl optionally substituted with —C(=O)Z or one or more R; or a 6-10 membered aryl optionally substituted with one or more R;

Z denotes $OR^a$ or $NR^bR^c$;

$R^a$ denotes H, $C_1$-$C_4$-alkyl, $C_3$-$C_6$-cycloalkyl, $C_2$-$C_4$-alkylene-O—$C_1$-$C_4$-alkyl, $C_2$-$C_4$-alkylene-CN; $C_1$-$C_4$-alkyl substituted with one or two $Ar^7$;

$R^b$ denotes H, $C_1$-$C_4$-alkyl, $C_3$-$C_6$-cycloalkyl, $C_2$-$C_4$-alkylene-CN; $C_2$-$C_4$-alkylene-O—$C_1$-$C_4$-alkyl; or $C_1$-$C_4$-alkyl substituted with one or two $Ar^7$;

$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

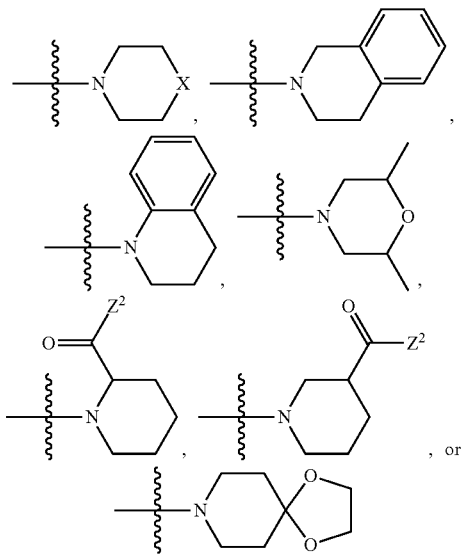

wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_3$-$C_6$-cycloalkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H, $C_1$-$C_4$-alkyl or $C_3$-$C_6$-cycloalkyl;

R independently denotes F, Cl, Br, I, $C_1$-$C_4$-haloalkyl, $OR^1$, $SR^1$, $NO_2$, $NR^2R^3$, $R^4$, C(=O)Y, $SO_3H$, $C_1$-$C_4$-alkyl, $C_1$-$C_4$-alkyl-phenyl, a 5-membered heteroaryl; or a phenyl substituted with a 5-membered heteroaryl;

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl; or $NR^2R^3$ denotes —NHC(=O)—$NHAr^8$; or together two adjacent $NR^2R^3$ groups denote —$NR^2$—CH=N— or —$NR^2$—$CH_2$—$NR^2$—; or together with an adjacent $OR^1$ group, $NR^2R^3$ denotes —$NR^2$—$CH_2$—O— or —N—CH—O—; or together with an adjacent $SR^1$ group, $NR^2R^3$ denotes —$NR^2$—$CH_2$—S— or —N—CH—S—;

$Ar^8$ denotes phenyl optionally substituted with $R^h$;

$R^h$ denotes halogen or $C_1$-$C_4$ alkyl;

$R^4$ denotes $C_1$-$C_4$-alkyl; or together with an adjacent $OR^1$ group, $R^4$ denotes —$CH_2CH_2$—O—; or together two adjacent $R^4$ groups denote —$(CH)_4$— or —$(CH_2)_4$—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

The compound of formula (Ic) may alternatively be represented by the following structure:

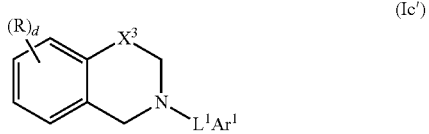

wherein $L^1$ denotes C(=O)$C_1$-$C_3$-alkylene optionally substituted with one phenyl, or $C_1$-$C_4$-alkylene optionally substituted with one phenyl;

d denotes an integer from 0 to 4;

$X^3$ denotes a $CH_2$ or a bond;

$Ar^1$ denotes a 5-10 membered heteroaryl optionally substituted with —C(=O)Z or one or more R; or a 6-10 membered aryl optionally substituted with one or more R;

Z denotes $OR^a$ or $NR^bR^c$;

$R^a$ denotes H, $C_1$-$C_4$-alkyl, $C_3$-$C_6$-cycloalkyl, $C_2$-$C_4$-alkylene-O—$C_1$-$C_4$-alkyl, $C_2$-$C_4$-alkylene-CN; $C_1$-$C_4$-alkyl substituted with one or two $Ar^7$;

$R^b$ denotes H, $C_1$-$C_4$-alkyl, $C_3$-$C_6$-cycloalkyl, $C_2$-$C_4$-alkylene-CN; $C_2$-$C_4$-alkylene-O—$C_1$-$C_4$-alkyl; or $C_1$-$C_4$-alkyl substituted with one or two $Ar^7$;

$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

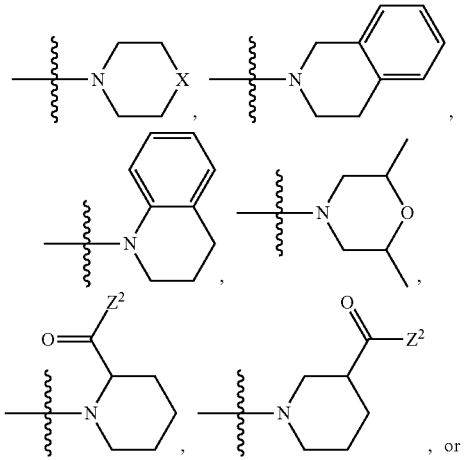

-continued

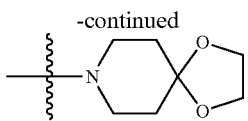

wherein X denotes CHZ$^1$, O, or NZ$^1$;

Z$^1$ denotes H, C(=O)H, C(=O)C$_1$-C$_4$-alkyl, C(=O)OR$^z$, Ar$^7$, C$_1$-C$_4$-alkyl, C$_3$-C$_6$-cycloalkyl, C$_1$-C$_4$-alkyl substituted with one or two Ar$^7$; C$_2$-C$_4$—NR$^d$R$^e$, or C$_2$-C$_4$—OR$^f$;

Z$^2$ denotes OR$^a$ or NR$^g$R$^g$;

Ar$^7$ denotes 5-6 membered heteroaryl; or phenyl optionally substituted with one or more R;

R$^d$, R$^e$ and R$^f$ independently denote H or C$_1$-C$_4$-alkyl;

R$^g$ denotes R$^b$;

R$^z$ denotes H, C$_1$-C$_4$-alkyl or C$_3$-C$_6$-cycloalkyl;

R independently denotes F, Cl, Br, I, C$_1$-C$_4$-haloalkyl, OR$^1$, SR$^1$, NO$_2$, NR$^2$R$^3$, R$^4$, C(=O)Y, SO$_3$H, C$_1$-C$_4$-alkyl, C$_1$-C$_4$-alkyl-phenyl, a 5-membered heteroaryl; or a phenyl substituted with a 5-membered heteroaryl;

R$^1$ denotes H, C$_1$-C$_4$-alkyl or C$_1$-C$_4$-alkyl-phenyl; or together two adjacent OR$^1$ groups denote —O—CH$_2$—O—;

R$^2$ and R$^3$ independently denote H or C$_1$-C$_4$-alkyl; or NR$^2$R$^3$ denotes —NHC(=O)—NHAr$^8$; or together two adjacent NR$^2$R$^3$ groups denote —NR$^2$—CH=N— or —NR$^2$—CH$_2$—NR$^2$—; or together with an adjacent OR$^1$ group, NR$^2$R$^3$ denotes —NR$^2$—CH$_2$—O— or —N=CH—O—; or together with an adjacent SR$^1$ group, NR$^2$R$^3$ denotes —NR$^2$—CH$_2$—S— or —N=CH—S—;

Ar$^8$ denotes phenyl optionally substituted with R$^h$;

R$^h$ denotes halogen or C$_1$-C$_4$ alkyl;

R$^4$ denotes C$_1$-C$_4$-alkyl; or together with an adjacent OR$^1$ group, R$^4$ denotes —CH$_2$CH$_2$—O—; or together two adjacent R$^4$ groups denote —(CH)$_4$— or —(CH$_2$)$_4$—;

Y denotes OR$^5$ or NR$^6$R$^7$;

R$^5$ denotes H or C$_1$-C$_4$-alkyl;

R$^6$ and R$^7$ independently denote H, C$_1$-C$_8$-alkyl or C$_3$-C$_6$ cycloalkyl.

As used herein, any reference to a compound of formula (Ic) should be interpreted as also a reference to the equivalent formula (Ic'). Thus, any method, use, composition or preferred substituent definition of formula (Ic) should also be interpreted as a reference to the compound of formula (Ic').

Preferably, in the compound of formula (Ic):
X$^3$ denotes CH$_2$.

Preferably, in the compound of formula (Ic):
X$^3$ denotes a bond.

Preferably, in the compound of formula (Ic):
d denotes 0, 1 or 2.

Preferably, in the compound of formula (Ic):
d denotes 0 or 1.

Preferably, in the compound of formula (Ic):
d denotes 0.

The following preferred embodiments relate to the compounds of formula (I), (Ia), (Ib) and (Ic) as defined above, as well as embodiments 1, 1a, 2, 2a, 3, 3a, 4, 4a, 5, 5a, 6, 6a, 7, 7a, 8, 8a, 9, 9a, 10, 10a, 11, 11a, 12, 12a, 13, 13a, 14, 14a, 15, 15a, and 16-18 as defined above:

Preferably, Ar$^1$, Ar$^2$, Ar$^3$, Ar$^4$, Ar$^5$ and Ar$^6$ independently denote a 5-9 membered heteroaryl optionally substituted with —C(=O)Z or one or more R; or a 6-10 membered aryl optionally substituted with one or more R.

Preferably, Ar$^1$, Ar$^2$, Ar$^3$, Ar$^4$, Ar$^5$ and Ar$^6$ independently denote a 5-6 membered heteroaryl optionally substituted with —C(=O)Z or one or more R; or a 6-10 membered aryl optionally substituted with one or more R.

Preferably, Ar$^1$, Ar$^2$, Ar$^3$, Ar$^4$, Ar$^5$ and Ar$^6$ independently denote a 5- or 6-membered heteroaryl optionally substituted with —C(=O)Z or one or more R; or a phenyl optionally substituted with one or more R.

Preferably, Ar$^1$, Ar$^2$, Ar$^3$, Ar$^4$, Ar$^5$ and Ar$^6$ independently denote a thiazole optionally substituted with —C(=O)Z; an oxazole optionally substituted with —C(=O)Z; or a phenyl optionally substituted with one or more R.

Preferably, Ar$^1$, Ar$^2$, Ar$^3$, Ar$^4$, Ar$^5$ and Ar$^6$ independently denote a thiazole optionally substituted with —C(=O)Z; or a phenyl optionally substituted with one or more R.

Preferably, when Ar$^1$, Ar$^2$, Ar$^3$ or Ar$^7$ are optionally substituted with one or more R, the (hetero)aryl ring has 0, 1 or 2 substituents.

Preferably, Ar$^1$ denotes phenyl optionally substituted with one or two R;

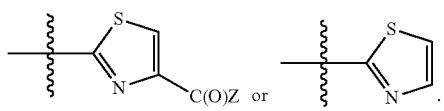

Preferably, Ar$^1$ denotes phenyl optionally substituted with one or two R; or

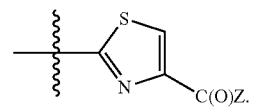

Preferably, Ar$^1$ denotes

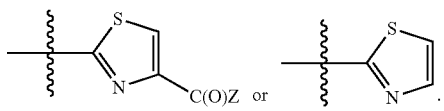

Preferably, Ar$^1$ denotes

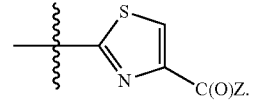

Preferably, Ar$^1$ denotes phenyl optionally substituted with one or more R.

Preferably, Ar$^1$ denotes phenyl optionally substituted with one or two R.

Preferably, Ar$^3$ denotes phenyl optionally substituted with one or two R.

Preferably, Ar$^5$ denotes phenyl optionally substituted with one or two R.

Preferably, Ar$^6$ denotes phenyl optionally substituted with one or two R.

Preferably, Ar$^2$ denotes phenyl optionally substituted with one or two R; or thiazole optionally substituted with —C(=O)Z.

Preferably, Ar$^4$ denotes phenyl optionally substituted with one or two R; or thiazole optionally substituted with —C(=O)Z.

Preferably, Ar² denotes phenyl optionally substituted with one or two R; or thiazole optionally substituted with —C(=O)Z.

Preferably, Ar² denotes phenyl optionally substituted with one or two R;

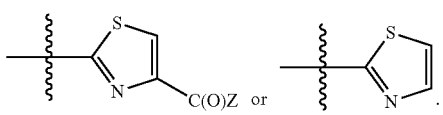

Preferably, Ar² denotes phenyl optionally substituted with one or two R; or

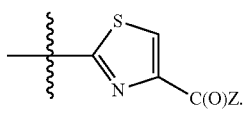

Preferably, $L^1$ and $L^5$ independently denote $C_1$-$C_3$-alkylene optionally substituted with one phenyl.

Preferably, $L^1$ denotes —CH₂—.

Preferably, $L^5$ denotes —CH₂—.

Preferably, $L^2$, $L^3$, $L^4$ and $L^6$ independently denote a bond or $C_1$-$C_2$-alkylene optionally substituted with one phenyl.

Preferably, $L^2$, $L^3$, $L^4$ and $L^6$ denote a bond.

Preferably, Ar³ denotes phenyl optionally substituted with one or two R; pyridyl, or 2-furyl.

Preferably, Ar³ denotes phenyl optionally substituted with one or two R; or pyridyl.

Preferably, Ar³ denotes phenyl optionally substituted with one or two R.

Preferably, $L^3$ denotes —CH₂—, —CH(CH₃)— or —CH₂CH₂CH(C₆H₅)—.

Preferably, $L^3$ denotes —CH₂— or —CH₂CH₂CH(C₆H₅)—; and

Ar³ denotes phenyl optionally substituted with one or two R.

Preferably, Z denotes ORᵃ.

Preferably, Rᵃ denotes H or Me.

Preferably, Z denotes NRᵇRᶜ.

Preferably, Rᵇ denotes H or $C_1$-$C_4$-alkyl; and

Rᶜ denotes H, $C_1$-$C_4$ alkyl, cyclopropyl, cyclohexyl, Ar⁷, $C_1$-$C_4$-alkyl substituted with one or two Ar⁷; OH, or O—$C_1$-$C_4$-alkyl;

or together NRᵇRᶜ denotes

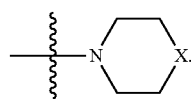

Preferably, Rᵇ denotes H or $C_1$-$C_4$-alkyl; and

Rᶜ denotes H, $C_1$-$C_6$ alkyl, $C_1$-$C_4$-alkyl substituted with one or two Ar⁷;

or together NRᵇRᶜ denotes

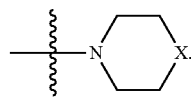

Preferably, Rᵇ denotes H; and

Rᶜ denotes H, $C_1$-$C_6$ alkyl, $C_1$-$C_4$-alkyl substituted with one or two Ar⁷;

or together NRᵇRᶜ denotes

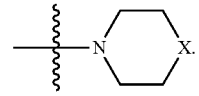

Preferably, together NRᵇRᶜ denotes

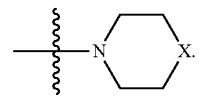

Preferably, X denotes NZ¹.

Preferably, Z¹ denotes H, C(=O)H, C(=O)$C_1$-$C_4$-alkyl, C(=O)ORᶻ, Ar⁷, $C_1$-$C_4$-alkyl, or $C_1$-$C_4$-alkyl substituted with one or two Ar⁷.

Preferably, Z¹ denotes H, C(=O)H, C(=O)$C_1$-$C_4$-alkyl, or C(=O)ORᶻ.

Preferably, Z¹ denotes H, Ar⁷, $C_1$-$C_4$-alkyl, or $C_1$-$C_4$-alkyl substituted with one or two Ar⁷.

Preferably, Ar⁷ denotes phenyl optionally substituted with one or two R.

Preferably, Rᵍ denotes H or $C_1$-$C_4$-alkyl.

Preferably, Rʰ denotes F or $C_1$-$C_4$-alkyl.

Preferably, Rʰ denotes F or methyl.

Preferably, Rᶻ denotes H or methyl.

Preferably, R independently denotes F, Cl, CF₃, OR¹, NO₂, NR²R³, R⁴, C(=O)Y, $C_1$-$C_4$-alkyl, $C_1$-$C_4$-alkyl-phenyl, or

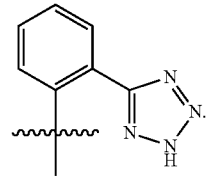 [SMILES: *c1ccccc1-c1nn[nH]n1]

Preferably, R independently denotes F, Cl, CF₃, OR¹, C(=O)Y, $C_1$-$C_4$-alkyl, $C_1$-$C_4$-alkyl-phenyl or

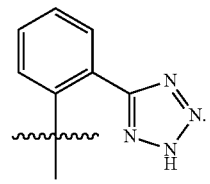 [SMILES: *c1ccccc1-c1nn[nH]n1]

Preferably, R independently denotes F, Cl, CF₃, OR¹, C(=O)Y, $C_1$-$C_4$-alkyl or $C_1$-$C_4$-alkyl-phenyl.

Preferably, Y denotes OR⁵.

Preferably, R⁶ and R⁷ independently denote H and $C_1$-$C_6$-alkyl.

The above noted preferred embodiments can of course be combined with one another. Thus, particularly preferred embodiments of the invention include:

Embodiment 19

A compound of formula (Ia), or a pharmaceutically acceptable salt thereof, including all stereoisomers and tautomers thereof, for use in therapy, wherein $L^1$ denotes $C_1$-$C_3$-alkylene optionally substituted with one phenyl;

$L^2$ and $L^3$ independently denote a bond or $C_1$-$C_2$-alkylene optionally substituted with one phenyl;

$Ar^1$ denotes phenyl optionally substituted with one or more R;

$Ar^2$ denotes phenyl optionally substituted with one or two R; or thiazole optionally substituted with —C(=O)Z;

$Ar^3$ denotes phenyl optionally substituted with one or two R; pyridyl, or 2-furyl;

Z denotes $OR^a$ or $NR^bR^c$;

$R^a$ denotes H or $C_1$-$C_4$-alkyl;

$R^b$ denotes H, $C_1$-$C_4$-alkyl, $C_2$-$C_4$-alkyl-CN; or $C_1$-$C_4$-alkyl substituted with one or two $Ar^7$;

$R^c$ denotes H, $C_1$-$C_8$ alkyl, $C_3$-$C_6$ cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

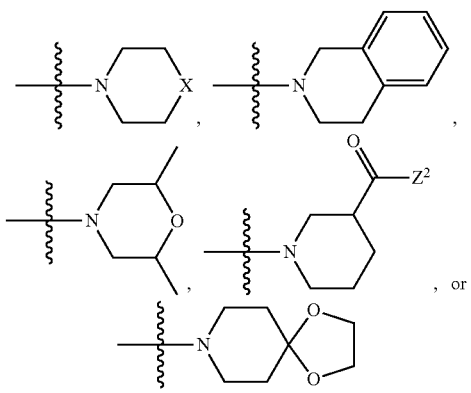

wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes phenyl optionally substituted with one or two R;

$R^d$, $R^e$ and $R^f$ independently denote H or $C_1$-$C_4$-alkyl;

$R^g$ denotes $R^b$;

$R^z$ denotes H or $C_1$-$C_4$-alkyl;

R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl or

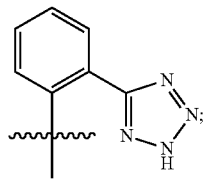 [SMILES: *c1ccccc1-c1nn[nH]n1]

$R^1$ denotes H, $C_1$-$C_4$-alkyl or $C_1$-$C_4$-alkyl-phenyl; or together two adjacent $OR^1$ groups denote —O—$CH_2$—O—; or together two adjacent $NR^2R^3$ groups denote —$NR^2$—CH—N— or —$NR^2$—$CH_2$—$NR^2$—; or together with an adjacent $OR^1$ group, $NR^2R^3$ denotes —$NR^2$—$CH_2$—O— or —N—CH—O—;

$R^2$ and $R^3$ independently denote H or $C_1$-$C_4$-alkyl;

$R^4$ denotes $C_1$-$C_4$-alkyl; or together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

Alternatively, embodiment 19a is identical to embodiment 19 except $Ar^1$ denotes phenyl optionally substituted with one or two R; or thiazole optionally substituted with —C(=O)Z; and $Ar^2$ denotes phenyl optionally substituted with one or more R.

Preferably, in embodiment 19 and 19a a, b, $X^2G$, $X^3$ and $X^4$ are as in any of embodiments 2, 2a, 4, 4a, 5, 5a, 6, 6a, 13, 13a, 14, 14a, 15 or 15a.

Embodiment 20

A compound of formula (Ia), or a pharmaceutically acceptable salt thereof, including all stereoisomers and tautomers thereof, for use in therapy, wherein $L^1$ denotes $C_1$-$C_3$-alkylene optionally substituted with one phenyl; $L^2$ and $L^3$ independently denote a bond or $C_1$-$C_2$-alkylene optionally substituted with one phenyl;

$Ar^1$ denotes phenyl optionally substituted with one or more R;

$Ar^2$ denotes phenyl optionally substituted with one or two R;

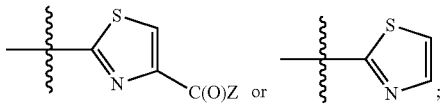

$Ar^a$ denotes phenyl optionally substituted with one or two R; pyridyl, or 2-furyl;

Z denotes $OR^a$ or $NR^bR^c$;

$R^a$ denotes H or $C_1$-$C_4$-alkyl;

$R^b$ denotes $R^b$ denotes H or $C_1$-$C_4$-alkyl; and $R^c$ denotes H, $C_1$-$C_4$ alkyl, cyclopropyl, cyclohexyl, $Ar^7$, $C_1$-$C_4$-alkyl substituted with one or two $Ar^7$; OH, or O—$C_1$-$C_4$-alkyl;

or together $NR^bR^c$ denotes

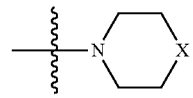

X denotes $CHZ^1$, O, or $NZ^1$;

$Z^1$ denotes $Z^1$ denotes H, C(=O)H, C(=O)$C_1$-$C_4$-alkyl, C(=O)$OR^z$, $Ar^7$, $C_1$-$C_4$-alkyl, or $C_1$-$C_4$-alkyl substituted with one or two $Ar^7$;

$Z^2$ denotes $OR^a$ or $NR^gR^g$;

$Ar^7$ denotes phenyl optionally substituted with one or two R;

$R^d$, $R^e$ and $R^f$ independently denote H or $C_1$-$C_4$-alkyl;

$R^g$ denotes $R^b$;

$R^z$ denotes H or $C_1$-$C_4$-alkyl;

R independently denotes F, Cl, $CF_3$, $OR^1$, C(=O)Y, $C_1$-$C_4$-alkyl, $C_1$-$C_4$-alkyl-phenyl or

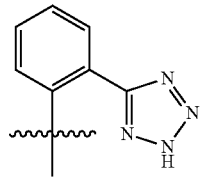 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—;

$R^2$ and $R^3$ independently denote H or $C_1$-$C_4$-alkyl;

$R^4$ denotes $C_1$-$C_4$-alkyl; or
together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H and $C_1$-$C_6$-alkyl.

Alternatively, embodiment 20a is identical to embodiment 20 except $Ar^1$ denotes phenyl optionally substituted with one or two R;

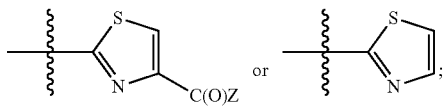

and $Ar^2$ denotes phenyl optionally substituted with one or more R.

Preferably, in embodiment 20 and 20a a, b, $X^2G$, $X^3$ and $X^4$ are as in any of embodiments 2, 2a, 4, 4a, 5, 5a, 6, 6a, 13, 13a, 14, 14a, 15 or 15a.

Embodiment 21

A compound of formula (Ia), or a pharmaceutically acceptable salt thereof, including all stereoisomers and tautomers thereof, for use in therapy, wherein $L^1$ denotes —$CH_2$;

$L^2$ denotes a bond;

$L^3$ denotes a bond, —$CH_2$—, —$CH(CH_3)$— or —$CH_2CH(C_6H_5)$—;

$Ar^1$ denotes phenyl optionally substituted with one or two R;

$Ar^2$ denotes phenyl optionally substituted with one or two R;

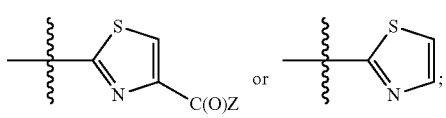

$Ar^3$ denotes phenyl optionally substituted with one or two R; pyridyl, or 2-furyl;

Z denotes $OR^a$ or $NR^bR^c$;

$R^a$ denotes H or $C_1$-$C_4$-alkyl;

$R^b$ denotes H or $C_1$-$C_4$-alkyl; and $R^c$ denotes H, $C_1$-$C_4$ alkyl, cyclopropyl, cyclohexyl, $Ar^7$, $C_1$-$C_4$-alkyl substituted with one or two $Ar^7$; OH, or O—$C_1$-$C_4$-alkyl;

or together $NR^bR^c$ denotes

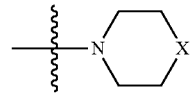

X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, or $C_1$-$C_4$-alkyl substituted with one or two $Ar^7$;

$Z^2$ denotes $OR^a$ or $NR^gR^g$;

$Ar^7$ denotes phenyl optionally substituted with one or two R;

$R^d$, $R^e$ and $R^f$ independently denote H or $C_1$-$C_4$-alkyl;

$R^g$ denotes $R^b$;

$R^z$ denotes H or $C_1$-$C_4$-alkyl;

R independently denotes F, Cl, $CF_3$, $OR^1$, C(=O)Y, $C_1$-$C_4$-alkyl, $C_1$-$C_4$-alkyl-phenyl or

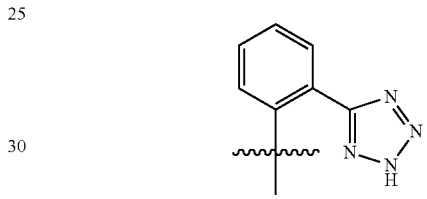

$R^1$ denotes H, $C_1$-$C_4$-alkyl or $C_1$-$C_4$-alkyl-phenyl; or
together two adjacent $OR^1$ groups denote —O—$CH_2$—O—;

$R^2$ and $R^3$ independently denote H or $C_1$-$C_4$-alkyl;

$R^4$ denotes $C_1$-$C_4$-alkyl; or
together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H and $C_1$-$C_6$-alkyl.

Alternatively, embodiment 21a is identical to embodiment 21 except $Ar^1$ denotes phenyl optionally substituted with one or two R,

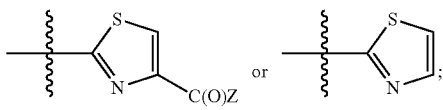

and $Ar^2$ denotes phenyl optionally substituted with one or two R.

Preferably, in embodiment 21 and 21a a, b, $X^2G$, $X^3$ and $X^4$ are as in any of embodiments 2, 2a, 4, 4a, 5, 5a, 6, 6a, 13, 13a, 14, 14a, 15 or 15a.

Embodiment 22

A compound of formula (Ia), or a pharmaceutically acceptable salt thereof, including all stereoisomers and tautomers thereof, for use in therapy, wherein $L^1$ denotes —$CH_2$;

$L^2$ denotes a bond;

$L^3$ denotes a bond, —$CH_2$—, —$CH(CH_3)$— or —$CH_2CH(C_6H_5)$—;
$Ar^1$ denotes phenyl optionally substituted with one or two R;
$Ar^2$ denotes phenyl optionally substituted with one or two R;

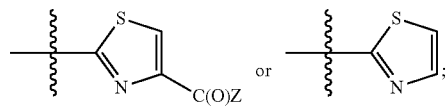

$Ar^a$ denotes phenyl optionally substituted with one or two R; pyridyl, or 2-furyl;
Z denotes $NR^bR^c$;
$R^b$ denotes H; and
$R^c$ denotes H, $C_1$-$C_6$ alkyl, $C_1$-$C_4$-alkyl substituted with one or two $Ar^7$;
or together $NR^bR^c$ denotes

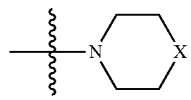

X denotes $NZ^1$;
$Z^1$ denotes H, C(=O)H, C(=O)$C_1$-$C_4$-alkyl, C(=O)$OR^z$, $Ar^7$, $C_1$-$C_4$-alkyl, or $C_1$-$C_4$-alkyl substituted with one or two $Ar^7$;
$Z^2$ denotes $OR^a$ or $NR^gR^g$;
$Ar^7$ denotes phenyl optionally substituted with one or two R;
$R^d$, $R^e$ and $R^f$ independently denote H or $C_1$-$C_4$-alkyl;
$R^g$ denotes $R^b$;
$R^z$ denotes H or $C_1$-$C_4$-alkyl;
R independently denotes F, Cl, $CF_3$, $OR^1$, C(=O)Y, $C_1$-$C_4$-alkyl, $C_1$-$C_4$-alkyl-phenyl or

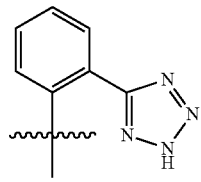 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.
Alternatively, embodiment 22a is identical to embodiment 22, except
$Ar^1$ denotes phenyl optionally substituted with one or two R,

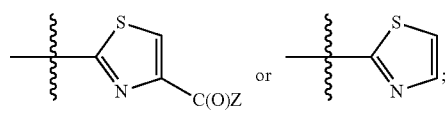

and
$Ar^2$ denotes phenyl optionally substituted with one or two R.
Preferably, in embodiment 22 and 22a
a, b, $X^2G$, $X^3$ and $X^4$ are as in any of embodiments 2, 2a, 4, 4a, 5, 5a, 6, 6a, 13, 13a, 14, 14a, 15 or 15a.

Embodiment 23

A compound of formula (Ia), or a pharmaceutically acceptable salt thereof, including all stereoisomers and tautomers thereof, for use in therapy, wherein
$L^1$ denotes —$CH_2$;
$L^2$ denotes a bond;
$L^3$ denotes a bond, —$CH_2$—, —$CH(CH_3)$— or —$CH_2CH(C_6H_5)$—;
$Ar^1$ denotes phenyl optionally substituted with one or two R;
$Ar^2$ denotes phenyl optionally substituted with one or two R;

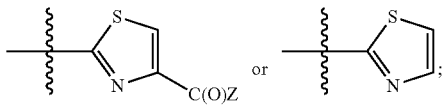

$Ar^3$ denotes phenyl optionally substituted with one or two R; pyridyl, or 2-furyl;
Z denotes $NR^bR^c$;
$R^b$ denotes H; and
$R^c$ denotes H, $C_1$-$C_6$ alkyl, $C_1$-$C_4$-alkyl substituted with one or two $Ar^7$;
or together $NR^bR^c$ denotes

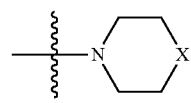

X denotes $NZ^1$;
$Z^1$ denotes H, C(=O)H, C(=O)$C_1$-$C_4$-alkyl, C(=O)$OR^z$, $Ar^7$, $C_1$-$C_4$-alkyl, or $C_1$-$C_4$-alkyl substituted with one or two $Ar^7$;
$Z^2$ denotes $OR^a$ or $NR^gR^g$;
$Ar^7$ denotes phenyl optionally substituted with one or two R;
$R^d$, $R^e$ and $R^f$ independently denote H or $C_1$-$C_4$-alkyl;
$R^g$ denotes $R^b$;
$R^z$ denotes H or $C_1$-$C_4$-alkyl;
R independently denotes F, Cl, $CF_3$, $OR^1$, C(=O)Y, $C_1$-$C_4$-alkyl or $C_1$-$C_4$-alkyl-phenyl;
$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.

Alternatively, embodiment 23a is identical to embodiment 23, except

Ar¹ denotes phenyl optionally substituted with one or two R,

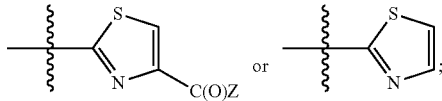

and

Ar² denotes phenyl optionally substituted with one or two R.

Preferably, in embodiment 23 and 23a
a, b, $X^2G$, $X^3$ and $X^4$ are as in any of embodiments 2, 2a, 4, 4a, 5, 5a, 6, 6a, 13, 13a, 14, 14a, 15 or 15a.

Embodiment 24

A compound of formula (Ic), or a pharmaceutically acceptable salt thereof, including all stereoisomers and tautomers thereof, for use in therapy, wherein $L^1$ denotes $C_1$-$C_3$-alkylene optionally substituted with one phenyl;

$Ar^1$ denotes phenyl optionally substituted with one or more R; thiazole optionally substituted with —C(=O)Z; pyridyl or 2-furyl;

Z denotes $OR^a$ or $NR^bR^c$;

$R^a$ denotes H or $C_1$-$C_4$-alkyl;

$R^b$ denotes H, $C_1$-$C_4$-alkyl, $C_2$-$C_4$-alkyl-CN; or $C_1$-$C_4$-alkyl substituted with one or two $Ar^7$;

$R^c$ denotes H, $C_1$-$C_8$ alkyl, $C_3$-$C_6$ cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

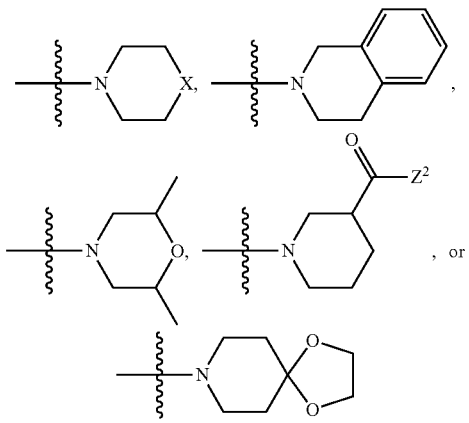

wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes phenyl optionally substituted with one or two R;

$R^d$, $R^e$ and $R^f$ independently denote H or $C_1$-$C_4$-alkyl;

$R^g$ denotes $R^b$;

$R^z$ denotes H or $C_1$-$C_4$-alkyl;

R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl or

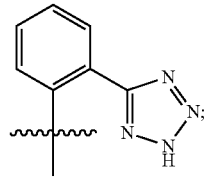 [SMILES: *c1ccccc1-c1nn[nH]n1]

$R^1$ denotes H, $C_1$-$C_4$-alkyl or $C_1$-$C_4$-alkyl-phenyl; or together two adjacent $OR^1$ groups denote —O—$CH_2$—O—; or together two adjacent $NR^2R^3$ groups denote —$NR^2$—CH—N— or —$NR^2$—$CH_2$—$NR^2$—; or together with an adjacent $OR^1$ group, $NR^2R^3$ denotes —$NR^2$—$CH_2$—O— or —N—CH—O—;

$R^2$ and $R^3$ independently denote H or $C_1$-$C_4$-alkyl;

$R^4$ denotes $C_1$-$C_4$-alkyl; or together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

Embodiment 25

A compound of formula (Ic), or a pharmaceutically acceptable salt thereof, including all stereoisomers and tautomers thereof, for use in therapy, wherein $L^1$ denotes $C_1$-$C_3$-alkylene optionally substituted with one phenyl;

$Ar^1$ denotes phenyl optionally substituted with one or more R; pyridyl; 2-furyl;

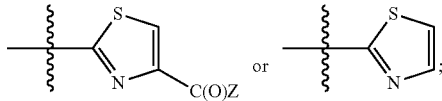

Z denotes $OR^a$ or $NR^bR^c$;

$R^a$ denotes H or $C_1$-$C_4$-alkyl;

$R^b$ denotes $R^b$ denotes H or $C_1$-$C_4$-alkyl; and $R^c$ denotes H, $C_1$-$C_4$ alkyl, cyclopropyl, cyclohexyl, $Ar^7$, $C_1$-$C_4$-alkyl substituted with one or two $Ar^7$; OH, or O—$C_1$-$C_4$-alkyl;

or together $NR^bR^c$ denotes

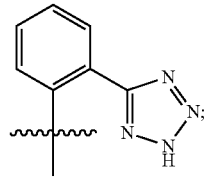 [SMILES: *c1ccccc1-c1nn[nH]n1]

X denotes $CHZ^1$, O, or $NZ^1$;

$Z^1$ denotes $Z^1$ denotes H, C(=O)H, C(=O)$C_1$-$C_4$-alkyl, C(=O)$OR^z$, $Ar^7$, $C_1$-$C_4$-alkyl, or $C_1$-$C_4$-alkyl substituted with one or two $Ar^7$;

$Z^2$ denotes $OR^a$ or $NR^gR^g$;

$Ar^7$ denotes phenyl optionally substituted with one or two R;

$R^d$, $R^e$ and $R^f$ independently denote H or $C_1$-$C_4$-alkyl;

$R^g$ denotes $R^b$;
$R^z$ denotes H or $C_1$-$C_4$-alkyl;
R independently denotes F, Cl, $CF_3$, $OR^1$, C(=O)Y, $C_1$-$C_4$-alkyl, $C_1$-$C_4$-alkyl-phenyl or

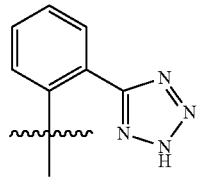 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.

Embodiment 26

A compound of formula (Ic), or a pharmaceutically acceptable salt thereof, including all stereoisomers and tautomers thereof, for use in therapy, wherein
$L^1$ denotes —$CH_2$;
$Ar^1$ denotes phenyl optionally substituted with one or two R; pyridyl; 2-furyl;

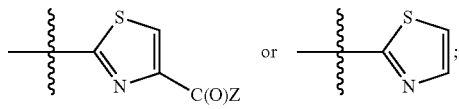

Z denotes $OR^a$ or $NR^bR^c$;
$R^a$ denotes H or $C_1$-$C_4$-alkyl;
$R^b$ denotes H or $C_1$-$C_4$-alkyl; and
$R^c$ denotes H, $C_1$-$C_4$ alkyl, cyclopropyl, cyclohexyl, $Ar^7$, $C_1$-$C_4$-alkyl substituted with one or two $Ar^7$; OH, or O—$C_1$-$C_4$-alkyl;
or together $NR^bR^c$ denotes

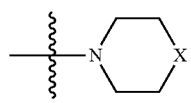

X denotes $CHZ^1$, O, or $NZ^1$;
$Z^1$ denotes H, C(=O)H, C(=O)$C_1$-$C_4$-alkyl, C(=O)$OR^z$, $Ar^7$, $C_1$-$C_4$-alkyl, or $C_1$-$C_4$-alkyl substituted with one or two $Ar^7$;
$Z^2$ denotes $OR^a$ or $NR^gR^g$;
$Ar^7$ denotes phenyl optionally substituted with one or two R;
$R^d$, $R^e$ and $R^f$ independently denote H or $C_1$-$C_4$-alkyl;
$R^g$ denotes $R^b$;
$R^z$ denotes H or $C_1$-$C_4$-alkyl;
R independently denotes F, Cl, $CF_3$, $OR^1$, C(=O)Y, $C_1$-$C_4$-alkyl, $C_1$-$C_4$-alkyl-phenyl or

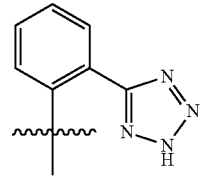 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.

Embodiment 27

A compound of formula (Ic), or a pharmaceutically acceptable salt thereof, including all stereoisomers and tautomers thereof, for use in therapy, wherein
$L^1$ denotes —$CH_2$;
$Ar^1$ denotes phenyl optionally substituted with one or two R; pyridyl;
R independently denotes F, Cl, $CF_3$, $OR^1$, C(=O)Y, $C_1$-$C_4$-alkyl, $C_1$-$C_4$-alkyl-phenyl or

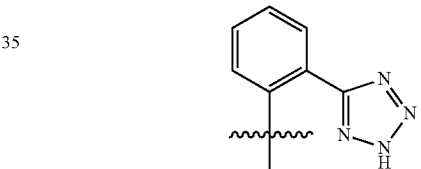

$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.
Preferably, in the compounds of formula (Ic) and particularly embodiments 24, 25, 26, and 27:
$Ar^1$ denotes phenyl optionally substituted with one or two R; 3-pyridyl; or 4-pyridyl.
Preferably, in the compounds of formula (Ic) and particularly embodiments 24, 25, 26, and 27:
$Ar^1$ denotes phenyl optionally substituted with one or two R.
Preferably, in the compounds of formula (Ic) and particularly embodiments 24, 25, 26, and 27:
$Ar^1$ denotes 3-pyridyl; or 4-pyridyl.
Preferably, in the compounds of formula (Ic) and particularly embodiments 24, 25, 26, and 27:
R independently denotes F, Cl, Br, I, $C_1$-$C_4$-haloalkyl, $OR^1$, $NO_2$, $R^4$, $C_1$-$C_4$-alkyl, or $C_1$-$C_4$-alkyl-phenyl.

Preferably, in the compounds of formula (Ic) and particularly embodiments 24, 25, 26, and 27:

R independently denotes F, Cl, Br, I, $OR^1$, $NO_2$, $R^4$, or $C_1$-$C_4$-alkyl; and $R^1$ denotes H or $C_1$-$C_4$-alkyl.

Preferably, in the compounds of formula (Ic) and particularly embodiments 24, 25, 26, and 27:

R independently denotes F, Cl, Br, I, $NO_2$, or $C_1$-$C_4$-alkyl.

Typically, the compound of formula (I) contains at least one group capable of acting as a hydrogen bond donor, and/or at least one group capable of acting as a hydrogen bond acceptor.

Preferably, the compound of formula (I) will contain at least one, more preferably two, groups capable of acting as a hydrogen bond donor.

Preferably, the compound of formula (I) will contain at least one, more preferably two, groups capable of acting as a hydrogen bond acceptor.

By "hydrogen bond donor" is meant a group containing a hydrogen atom capable of forming a hydrogen bond, such as OH or NH. Hydrogen bond donors may also form part of a ring, such as tetrazole NH groups.

By "hydrogen bond acceptor" is meant a group capable of forming a hydrogen bond with a hydrogen atom, such as OMe or $NMe_2$. Hydrogen bond acceptors may also form part of a ring, such as pyridyl nitrogen atoms.

In some embodiments, the $L^2Ar^2$ and $L^3Ar^3$ moieties in the compound of formula (Ia) are identical.

In some embodiments $L^2Ar^2$ and $L^3Ar^3$ in the compound of formula (Ia) are different.

The invention relates to compounds of formula (I) for use in therapy. However, some of the compounds themselves are previously unknown. The invention therefore also provides novel compounds that find use in therapy, for example compounds of formula (I) having the following structure:

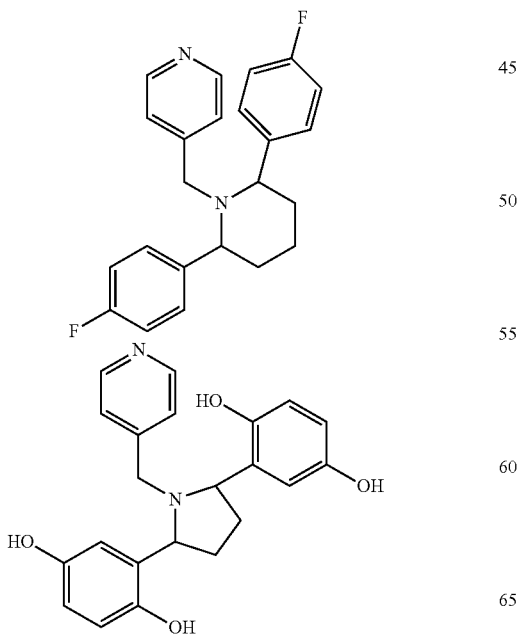

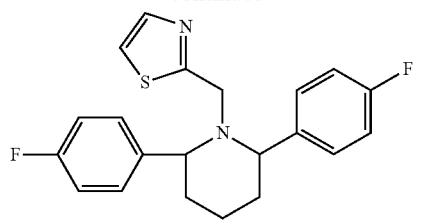

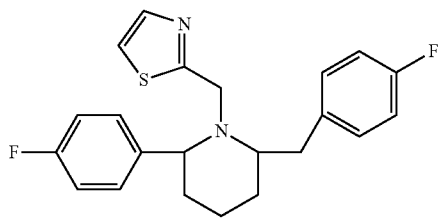

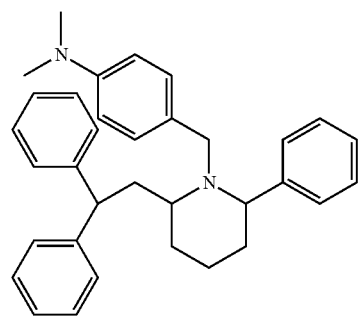

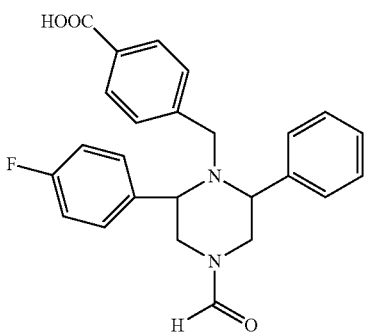

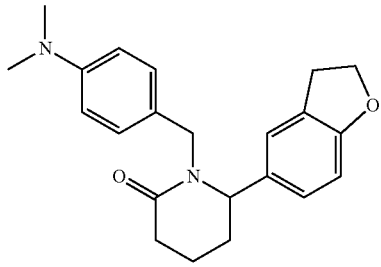

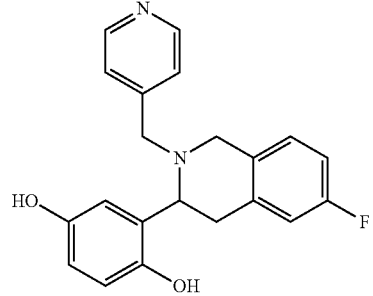

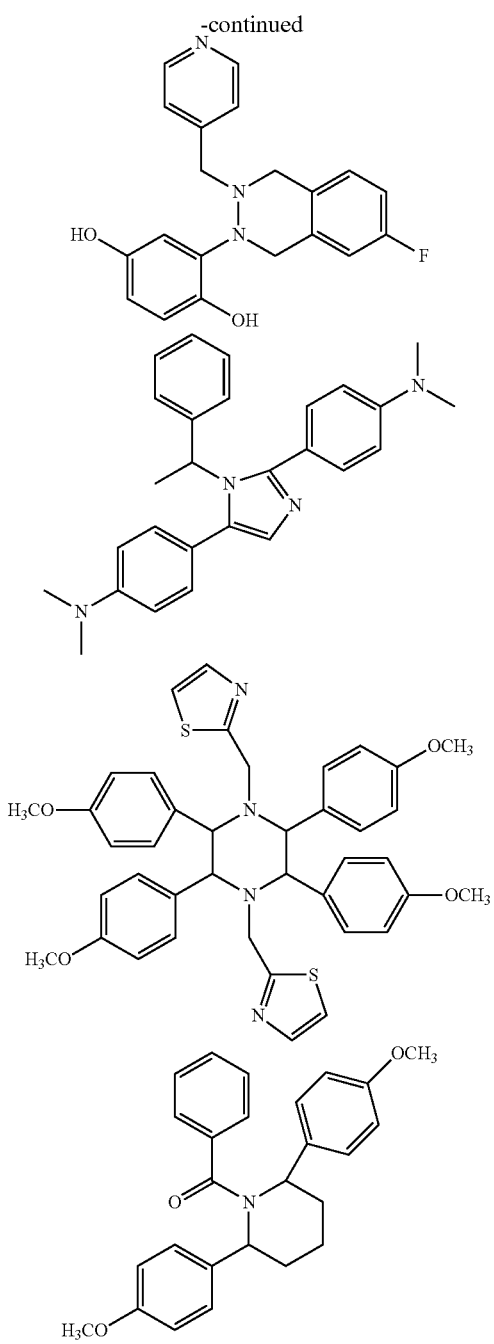

It is to be understood that where the preferred embodiments mentioned above are not mutually exclusive, they can be combined with one another. For example, the skilled person would understand that the above preferred embodiments in which Ar' (e.g. Ar$^1$) denotes phenyl optionally substituted with one or more R can be combined with the preferred embodiments in which R independently denotes F, Cl, CF$_3$, OR$^1$, C(=O)Y, C$_1$-C$_4$-alkyl or C$_1$-C$_4$-alkyl-phenyl. The same holds true for the other non-mutually exclusive preferred embodiments mentioned above. The skilled person would understand which embodiments where mutually exclusive and would thus readily be able to determine the combinations of preferred embodiments that are contemplated by the present application.

The compounds of the invention may be synthesised from readily available starting materials using general synthetic methods known in the art. Such methods include condensation reactions forming a heterocyclic ring. One such reaction is illustrated in Scheme 1 below.

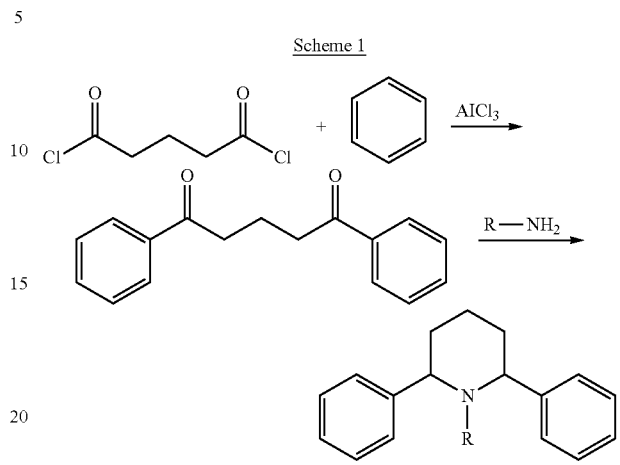

Scheme 1

As shown in Scheme 1, 2,6-diarylpiperidines may be prepared by reductive condensation of 1,3-diaroylpropanes with primary amines. The 1,3-diaroylpropanes may themselves be prepared by Friedel-Crafts reaction of glutaryl dichloride with excess arene, using methodology analogous to that used for the synthesis of 1,4-dibenzoylbutane from adipic acid by Reynold C. Fuson at al, in Organic Syntheses, Coll. Vol. 2, p. 169 (1943); Vol. 13, p. 32 (1933). Various amines, including for example benzyl amine, can be used in the condensation reaction. The formed products may then be further modified if required, for example by electrophilic aromatic substitution reactions on the aromatic rings and/or by salt formation.

If ammonia or a protected form of ammonia is used in the condensation reaction, a cyclic secondary amine is formed. This secondary amine may then be N-alkylated with various alkylating agents. The formed products may then be further modified, for example by electrophilic aromatic substitution reactions and/or salt formation.

In an alternative method, saturated or partially unsaturated compounds can be prepared by selective reduction of the corresponding fully unsaturated compounds, as illustrated in Scheme 2 below.

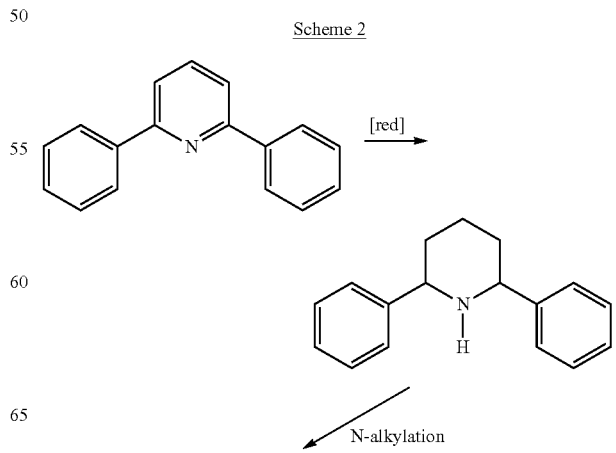

Scheme 2

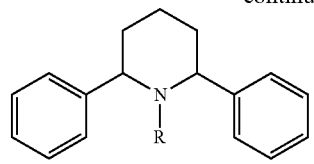

[red] = reduction

The products of the reduction may then be N-alkylated and, if desired, further modified, for example by electrophilic aromatic substitution reactions and/or salt formation.

Schemes 1 and 2 illustrate preparation of some piperidine derivatives. Other cyclic amines can be prepared in a similar way using different stating materials and methods well known in the literature.

Scheme 3 provides a more detailed outline for synthesis of compounds of the invention, using the general approach of Scheme 1.

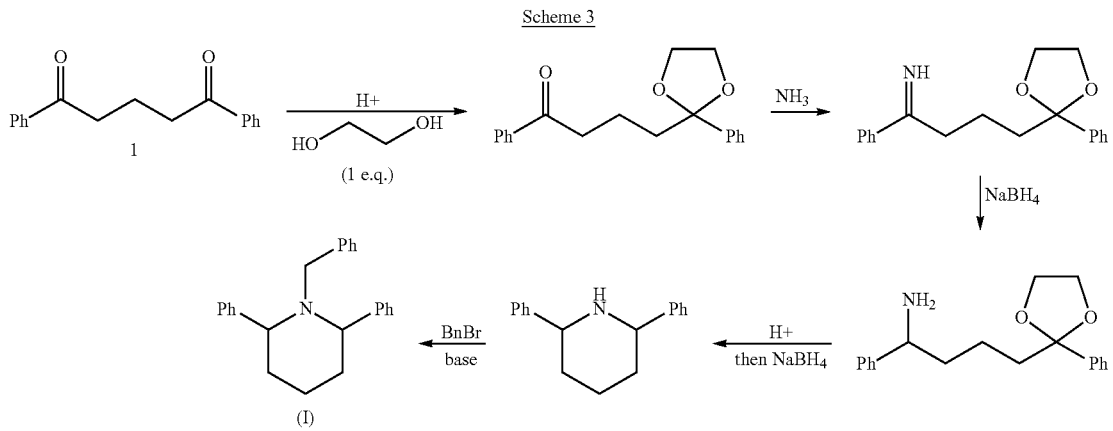

Scheme 3

Synthesis may begin with commercially available 1,3-dibenzoylpropane (1), or this may be synthesised via a Friedel-Crafts reaction, as outlined in Scheme 1. The final step in the reaction sequence could be adjusted to form various analogs of compounds of the invention. Many analogs of benzyl bromide are commercially available. For example, use of 4-methylbenzyl bromide would form an analogous compound with a methyl in the 4-position of the benzyl group. If desired, substituents could be added to the phenyl rings of starting material (1) using standard techniques known in the art, such as Friedel-Crafts alkylation. This could be carried our prior to the synthesis of compound (1), or afterwards. If carried out afterwards, depending on the methodology used to introduce additional functionality, protection of the ketone groups may be necessary. Protecting groups for ketones are well known in the art. An authoritative account describing the many alternatives to the trained practitioner is Greene et al. (*Protective Groups in Organic Synthesis*, 3rd Ed., Wiley-Interscience (1999)).

As used herein, "alkyl" or "alkylene" is intended to include both branched and straight-chain saturated aliphatic hydrocarbon groups having the specified number of carbon atoms. For example, "$C_1$-$C_6$ alkyl" is intended to include $C_1$, $C_2$, $C_3$, $C_4$, $C_5$ and $C_6$ alkyl groups. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

By "haloalkyl" is meant both branched and straight chain saturated aliphatic hydrocarbon groups having the specified number of carbon atoms, wherein at least one of the hydrogen atoms has been replaced by F, Cl, Br or I. Preferably, haloalkyl refers to perfluoroalkyl.

The term "cycloalkyl" refers to cyclized alkyl groups, including mono-, bi- or poly-cyclic ring systems. Exemplary cycloalkyl groups include, but are not limited to, cyclopropyl, cyclobutyl, cyclopentyl, cyclohexyl, norbornyl, adamantyl and the like. Branched cycloalkyl groups such as 1-methylcyclopropyl and 2-methylcyclopropyl are included in the definition of "cycloalkyl".

As used herein, the term "aryl", is intended to mean an aromatic moiety containing, if specified, the specified number of carbon atoms; for example phenyl or naphthyl.

As used herein, the term "heteroaryl", is intended to mean an aromatic moiety containing, if specified, the specified number of atoms with at least one of the ring atoms being selected from N, O or S. Examples of heteroaryl rings include pyrrole, furan, thiophene, imidazole, pyrazole, 1,2,3-triazole, 1,2,4-triazole, tetrazole, thiazole, oxazole, isoxazole, benzofuran, isobenzofuran, indole, isoindole, benzothiophene, benzo[c]thiophene, benzinimdazole, indazole, purine, benzoxazole, benzothiazole, pyridine, pyrimidine, pyrazine, pyrazidine, quinoline, isoquinoline, quinoxaline, quinazoline and cinnoline.

The compounds of formula (I), (Ia), (Ib) and (Ic), particularly the preferred embodiments set out above, are found to selectively target and disrupt Phospholamban-AKAP18δ, indicating that they would find use as cardioprotective agents following myocardial infarction.

Therefore, the present invention also relates to a compound of formula (I), (Ia), (Ib) or (Ic), or a pharmaceutically acceptable salt thereof, including all stereoisomers and tautomers thereof, for use in therapy.

These compounds, and pharmaceutical compositions comprising these compounds, may be used for treating or preventing conditions in which PKA type II signalling which regulates SERCA2 is abnormal, in particular when the activity of this pathway is elevated or reduced. Furthermore, anchoring disruption may be beneficial also when the signalling is normal in cases when the heart is damaged and needs to be protected from adrenergic stimuli and pacing.

Thus, viewed from a further aspect, the present invention preferably provides a method of regulating SERCA2 activity in a human or non-human animal wherein a compound of formula (I), (Ia), (Ib) or (Ic), or a pharmaceutically acceptable salt thereof, including all stereoisomers and tautomers thereof, is administered to said animal.

Viewed another way, the present invention provides a method of treating or preventing diseases or disorders exhibiting abnormal SERCA2 activity or which would benefit from a reduction or elevation in the activity of SERCA2 in a human or non-human animal wherein a compound of formula (I), (Ia), (Ib) or (Ic), or a pharmaceutically acceptable salt thereof, including all stereoisomers and tautomers thereof, is administered to said animal.

Alternatively stated, the present invention provides the use of a compound of formula (I), (Ia), (Ib) or (Ic), or a pharmaceutically acceptable salt thereof, including all stereoisomers and tautomers thereof, for the preparation of a medicament for the regulation of SERCA2 activity, preferably as described hereinbefore.

Alternatively stated, the present invention provides the use of a compound of formula (I), (Ia), (Ib) or (Ic), or a pharmaceutically acceptable salt thereof, including all stereoisomers and tautomers thereof, for the preparation of a medicament for treating or preventing diseases or disorders exhibiting abnormal SERCA2 activity or which would benefit from a reduction or elevation in the activity of SERCA2.

Preferably, the present invention relates to a compound of formula (I), (Ia), (Ib) or (Ic), or a pharmaceutically acceptable salt thereof, including all stereoisomers and tautomers thereof, for use in treating or preventing diseases or disorders exhibiting abnormal SERCA2 activity or which would benefit from a reduction or elevation in the activity of SERCA2.

A number of the examples show that the regulation of SERCA2 activity provided by the compounds of the invention is associated with their effect on PKA type II signalling.

Thus, viewed from a further aspect the present invention preferably provides a method of treating or preventing diseases or disorders exhibiting abnormal PKA type II signalling that regulates SERCA2 activity or which would benefit from a reduction or elevation in the levels of SERCA2 mediated PKA type II signalling, preferably as described hereinbefore, in a human or non-human animal wherein a pharmaceutical composition as described hereinbefore is administered to said animal.

Alternatively stated, the present invention provides the use of a pharmaceutical composition as defined herein for the preparation of a medicament for the treatment or prevention of diseases or disorders exhibiting abnormal PKA type II signalling that regulates SERCA2 activity or which would benefit from a reduction or elevation in the levels of SERCA2 mediated PKA type II signalling, preferably as described hereinbefore.

Preferably, the present invention relates to a compound of formula (I), (Ia), (Ib) or (Ic), or a pharmaceutically acceptable salt thereof, including all stereoisomers and tautomers thereof, for use in treating or preventing cardiovascular disease.

As referred to herein "cardiovascular disease" refers to a disease or disorder of the heart or vascular system which may be congenital or acquired and encompasses diseases such as congenital heart failure, hypertension, myocardial infarction, congestive heart failure, reperfusion damage, dilated cardiomyopathy, post infarction heart failure, arrhythmia, atherosclerotic peripheral arterial disease and alveolar hypoxia leading to pulmonary hypertension and right ventricle failure.

As used herein, "treating" refers to the reduction, alleviation or elimination, preferably to normal levels, of one or more of the symptoms of said disease, disorder or condition which is being treated, e.g. normal blood pressure, cardiac function, etc., relative to the symptoms prior to treatment. Where not explicitly stated, treatment encompasses prevention. "Preventing" refers to absolute prevention, i.e. maintenance of normal levels with reference to the extent or appearance of a particular symptom (e.g. hypertension) or reduction or alleviation of the extent or timing (e.g. delaying) of the onset of that symptom.

Preferably, the present invention relates to a compound of formula (I), (Ia), (Ib) or (Ic), or a pharmaceutically acceptable salt thereof, including all stereoisomers and tautomers thereof, for use in treating conditions related to the heart.

By "conditions related to the heart" is meant any disease or disorder related to the heart which may be congenital or acquired and encompasses diseases such as congenital heart failure, myocardial infarction, post infarction heart failure, congestive heart failure, reperfusion damage, dilated cardiomyopathy and arrhythmia.

Preferably, the present invention relates to a compound of formula (I), (Ia), (Ib) or (Ic), or a pharmaceutically acceptable salt thereof, including all stereoisomers and tautomers thereof, for use in treating myocardial infarction.

Preferably, the present invention relates to a compound of formula (I), (Ia), (Ib) or (Ic), or a pharmaceutically acceptable salt thereof, including all stereoisomers and tautomers thereof, for use in treating congestive heart failure.

Preferably, the present invention relates to a compound of formula (I), (Ia), (Ib) or (Ic), or a pharmaceutically acceptable salt thereof, including all stereoisomers and tautomers thereof, for use in protecting against reperfusion damage.

Preferably, the present invention relates to a compound of formula (I), (Ia), (Ib) or (Ic), or a pharmaceutically acceptable salt thereof, including all stereoisomers and tautomers thereof, for use in protecting against post infarction heart failure.

Preferably, the present invention relates to a compound of formula (I), (Ia), (Ib) or (Ic), or a pharmaceutically acceptable salt thereof, including all stereoisomers and tautomers thereof, for use in protecting against congenital heart failure.

Preferably, the present invention relates to a compound of formula (I), (Ia), (Ib) or (Ic), or a pharmaceutically acceptable salt thereof, including all stereoisomers and tautomers thereof, for use in protecting against dilated cardiomyopathy.

Preferably, the present invention relates to a compound of formula (I), (Ia), (Ib) or (Ic), or a pharmaceutically acceptable salt thereof, including all stereoisomers and tautomers thereof, for use in protecting against arrhythmia heart failure.

Preferably, the present invention relates to a compound of formula (I), (Ia), (Ib) or (Ic), or a pharmaceutically acceptable salt thereof, including all stereoisomers and tautomers thereof, for use in interfering with one or more functions of A-kinase proteins.

Preferably, the present invention relates to a compound of formula (I), (Ia), (Ib) or (Ic), or a pharmaceutically acceptable salt thereof, including all stereoisomers and tautomers thereof, for use in inhibiting phospholamban phosphorylation.

Preferably, the present invention relates to a compound of formula (I), (Ia), (Ib) or (Ic), or a pharmaceutically acceptable salt thereof, including all stereoisomers and tautomers thereof, for use in inhibiting phospholamban phosphorylation upon adrenergic stimulation.

Preferably, the present invention relates to a compound of formula (I), (Ia), (Ib) or (Ic), or a pharmaceutically acceptable salt thereof, including all stereoisomers and tautomers thereof, for use in inhibiting PKA-mediated phospholamban phosphorylation upon adrenergic stimulation.

Preferably, the present invention relates to a compound of formula (I), (Ia), (Ib) or (Ic), or a pharmaceutically acceptable salt thereof, including all stereoisomers and tautomers thereof, for use in regulating SERCA2 activity.

Preferably, the present invention relates to a compound of formula (I), (Ia), (Ib) or (Ic), or a pharmaceutically acceptable salt thereof, including all stereoisomers and tautomers thereof, for use in regulating or modulating adrenergic pacing of the heart.

Preferably, the present invention relates to a compound of formula (I), (Ia), (Ib) or (Ic), or a pharmaceutically acceptable salt thereof, including all stereoisomers and tautomers thereof, for use in mediating the adrenergic pacing of the heart.

Preferably, the present invention relates to a compound of formula (I), (Ia), (Ib) or (Ic), or a pharmaceutically acceptable salt thereof, including all stereoisomers and tautomers thereof, for use in inhibiting the adrenergic pacing of the heart.

Preferably, the present invention relates to a compound of formula (I), (Ia), (Ib) or (Ic), or a pharmaceutically acceptable salt thereof, including all stereoisomers and tautomers thereof, for use in preventing arrhythmia.

Preferably, the present invention relates to a compound of formula (I), (Ia), (Ib) or (Ic), or a pharmaceutically acceptable salt thereof, including all stereoisomers and tautomers thereof, for use in inhibiting protein kinase A binding to A-kinase anchor proteins.

Preferably, the present invention relates to a compound of formula (I), (Ia), (Ib) or (Ic), or a pharmaceutically acceptable salt thereof, including all stereoisomers and tautomers thereof, for use in inhibiting AKAP18δ binding to phospholamban.

The present invention also relates to methods of treating/inhibiting/protecting against/mediating (as the case may be) the above conditions, comprising administering to a human or non-human animal (e.g. a mammal) in need thereof a compound according to formula (I), (Ia), (Ib) or (Ic), or a pharmaceutically acceptable salt thereof, including all stereoisomers and tautomers thereof.

Subjects which may be treated are preferably mammalian, preferably humans and companion or agricultural animals such as dogs, cats, monkeys, horses, sheep, goats, cows, rabbits, rats and mice.

Preferred mammals are humans.

The present invention also relates to the use of a compound according to formula (I), (Ia), (Ib) or (Ic), or a pharmaceutically acceptable salt thereof, including all stereoisomers and tautomers thereof, for treating/inhibiting/protecting against/mediating (as the case may be) the above conditions.

The present invention also relates to a compound according to formula (I), (Ia), (Ib) or (Ic), or a pharmaceutically acceptable salt thereof, including all stereoisomers and tautomers thereof, for use in the manufacture of a medicament for use in treating/inhibiting/protecting against/mediating (as the case may be) the above conditions.

As shown by the examples below, the compounds of the invention are capable of influencing phospholamban phosphorylation. This is believed to be the first time the activity of this target has been modulated by chemical moieties.

Thus, viewed from a further aspect the present invention preferably provides a method of treating or preventing diseases or disorders associated with phospholamban phosphorylation, comprising administering to a subject in need thereof a pharmaceutically effective amount of a compound with molecular weight below 1000 Daltons (or g/mol) or pharmaceutically acceptable salts thereof.

By "diseases or disorders associated with phospholamban phosphorylation" is meant conditions which arise due to abnormal phospholamban phosphorylation, such as but not limited to post infarction heart failure and congestive heart failure, as well as conditions that may occur in patients showing normal phospholamban phosphorylation but which would benefit from a cardioprotective effect due to inhibition of phospholamban phosphorylation, such as but not limited to congenital heart failure, myocardial infarction, reperfusion damage, dilated cardiomyopathy, and arrhythmia.

Preferred diseases or disorders associated with phospholamban phosphorylation are cardiovascular diseases.

Preferred diseases or disorders associated with phospholamban phosphorylation are cardiovascular diseases selected from congenital heart failure, myocardial infarction, post infarction heart failure, congestive heart failure, reperfusion damage, dilated cardiomyopathy and arrhythmia.

The invention also relates to a method of regulating phospholamban phosphorylation comprising administering to a subject a pharmaceutically effective amount of a compound with molecular weight below 1000 Daltons, or pharmaceutically acceptable salts thereof.

The invention also relates to a method of inhibiting phospholamban phosphorylation comprising administering to a subject a pharmaceutically effective amount of a compound with molecular weight below 1000 Daltons, or pharmaceutically acceptable salts thereof.

The invention also relates to a method of regulating SERCA2 activity by influencing its interaction with phospholamban. This is believed to be the first time that this interaction has been selectively modulated by small molecule inhibitors.

In preferred embodiments, these methods use a nitrogen-containing compound. More preferably, said nitrogen-containing compound is an amine. Even more preferably, said amine is a tertiary amine.

Most preferably, said amine is an alkylaryl or alkylheteroaryl tertiary amine.

Thus, in a preferred aspect, the invention relates to a method of treating or preventing diseases or disorders associated with phospholamban phosphorylation, comprising administering to a subject in need thereof a pharmaceutically effective amount of a alkylaryl or alkylheteroaryl tertiary amine with molecular weight below 1000 Daltons or pharmaceutically acceptable salts thereof.

In such embodiments, "alkylaryl" means an alkylene group bonded to an aromatic ring containing only carbon atoms, which may optionally be substituted. By "alkylheteroaryl" is meant an alkylene group bonded to an aromatic ring containing carbon atoms and at least one heteroatom, which may optionally be substituted.

In preferred embodiments, the alkylaryl or alkylheteroaryl tertiary amine is a compound of formula (I), (Ia), (Ib) or (Ic), or a pharmaceutically acceptable salt thereof, including all stereoisomers and tautomers thereof.

The present invention also relates to pharmaceutical compositions comprising a compound according to formula (I), (Ia), (Ib) or (Ic), or a pharmaceutically acceptable salt thereof, including all stereoisomers and tautomers thereof, and one or more pharmaceutically acceptable excipients and/or diluents.

By "pharmaceutically acceptable" is meant that the ingredient must be compatible with other ingredients in the composition as well as physiologically acceptable to the recipient.

By "pharmaceutically acceptable salts" of compounds of formula (I) (or (Ia)) is meant pharmaceutically acceptable acid addition salts or pharmaceutically acceptable base salts.

Pharmaceutically acceptable acid addition salts comprise the therapeutically active non-toxic acid addition salts that the compounds of formula (I) (or (Ia)) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

As employed herein below the definition of compounds of formula (I) is intended to include all tautomers of said compounds, and solvates of said compounds (including solvates of salts of said compounds) unless the context specifically indicates otherwise. Examples of solvates include hydrates.

The invention provided herein extends to prodrugs of the compound of formula (I), that is to say compounds which break down and/or are metabolised in vivo to provide an active compound of formula (I). General examples of prodrugs include simple esters, and other esters such as mixed carbonate esters, carbamates, glycosides, ethers, acetals and ketals.

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from O-dealkylation.

The compounds of the disclosure include those where the atom specified is a naturally occurring or non-naturally occurring isotope, preferably a stable isotope. Thus the compounds of the disclosure include, for example, deuterium containing compounds and the like.

The disclosure also extends to all polymorphic forms of the compounds herein defined.

Pharmaceutical compositions for use according to the invention may be formulated in conventional manner using readily available ingredients. Thus, the active ingredient may be incorporated, optionally together with other active substances as a combined preparation, with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are well known in the art and include lactose, dextrose, sucrose, sorbitol, mannitol, starches, gum acacia, calcium phosphate, calcium carbonate, calcium lactose, corn starch, alginates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used. The compositions may additionally include lubricating agents, wetting agents, viscosity increasing agents, colouring agents, granulating agents, disintegrating agents, binding agents, osmotic active agents, emulsifying agents, suspending agents, preserving agents, sweetening agents, flavouring agents, adsorption enhancers, e.g. for nasal delivery (bile salts, lecithins, surfactants, fatty acids, chelators) and the like. The compositions of the invention may be formulated so as to provide quick, sustained or delayed release of the active ingredient after administration of the patient by employing procedures well known in the art.

The active ingredient in such compositions may comprise from about 0.01% to about 99% by weight of the formulation, preferably from about 0.1 to about 50%, for example 10%.

The invention also extends to pharmaceutical compositions as described above for use as a medicament.

It will be understood that preferred methods/uses/compositions described above utilise the preferred compounds of formula (I), (Ia), (Ib) or (Ic) defined above, particularly the preferred embodiments mentioned above.

The administration may be by any suitable method known in the medicinal arts, including for example oral, parenteral (e.g. intramuscular, subcutaneous, intraperitoneal or intravenous), percutaneous, buccal, rectal or topical administration or administration by inhalation.

The preferred routes of administration are oral administration and intravenous administration. Preferred formulations for the composition of the invention are therefore as a tablet, a capsule or an intravenous solution.

The tablets are typically prepared by direct compression or a granulation procedure, for example using standard fluid bed technology. The tablets are preferably coated with film coating or another coating such as an enteric coating.

The capsules are preferably gelatine capsules.

The composition for injection can be a ready to use solution or a dry material to be dissolved before administration. All intravenous compositions are sterile. Any sterilization method may be used, such as heat sterilization and aseptic preparation.

The compositions of the invention may contain the compound of formula (I) as a pharmaceutically acceptable salt thereof. Such salts might typically be HCl, HBr, sulphate salt, phosphate salt, nitrate salt and salts with sulphonic acids like for example methanesulphonic acid. Other salts include organic salts like acetate, citrate and fumarate. A salt form of the compound of formula (I) is preferred for intravenous administration.

The unit dose will vary depending upon choice of compound and disease or disorder being treated.

Typically, the unit dose will vary from 0.1 mg to 500 mg; more preferably from 1 mg to 300 mg. A typical daily dose will be from 0.1 mg to 2 grams, more preferably 1 mg to 1 g, even more preferably 1 mg to 600 mg.

Typical daily doses per kg body weight of the patient vary from 5 mg/kg/day to 50 mg/kg/day, preferably from 10 mg/kg/day to 40 mg/kg/day.

Typically, the tablet or capsule weight is between 70 mg and 1 gram. Typically, the injection or infusion volume is between 0.3 ml and 500 ml.

The dosing regime will vary depending upon the clinical situation. Typical average dosing will be once, twice or three times a day, preferably once or twice a day.

The precise dosage of the active compound to be administered and the length of the course of treatment will of course, depend on a number of factors including for example, the age and weight of the patient, the specific condition requiring treatment and its severity, and the route of administration.

The compounds of formula (I) typically show an $EC_{50}$ value (as determined by the AlphaScreen described in the Examples) of 200 μM or below, preferably 100 μM or below, more preferably 50 μM or below, more preferably 25 μM or below, most preferably 10 μM or below, such as 5 μM or below.

The method of treatment according to the invention may advantageously be combined with administration of one or more active ingredients which are effective in treating the disorder or disease to be treated. Thus, pharmaceutical compositions of the invention may additionally contain one or more of such active ingredients.

Co-administration with other cardiovascular drugs is particularly preferred. For example, it is preferable to co-administer the compounds of formula (I) with drugs that treat hypertension, heart failure, arrhythmia and post infarction. It is more preferable to co-administer the compounds of formula (I) with drugs that treat hypertension, heart failure, arrhythmia and post infarction myocardial reperfusion syndrome.

The most preferred drugs to be administered together with the compounds of formula (I) are beta-blockers, calcium antagonists, ACE-inhibitors, ATII/-blockers and anti-arrhythmic drugs.

The following Examples are given by way of illustration only.

EXAMPLES

Binding Assay

Stable and optimal assay conditions were determined by cross-titrating GST-AKAP186 and biotinylated PLB using 10 μg/ml glutathione acceptor beads and 10 μg/ml streptavidin donor beads in an AlphaScreen assay. The excitation wavelength was 680 nm, with the emission wavelength being 520-560 nm. Signal intensity in each well was registered and the optimal concentration to use was chosen to be the concentration prior to the peak of the signal. The set up of the assay and cross-titration results are shown in FIGS. 1A and 1B.

Concentrations to give a reliable signal were determined to be between 2 and 16 nM for AKAP18δ-GST and 4 and 20 nM PLB-biotin for relevant preparations of protein, for example 4 nM and 20 nM, respectively.

Example 1

Screening compound library was screened with the above assay. The following compounds analogous to those of formula (I) were identified as having relatively low $EC_{50}$ values (2.0 μM-137 μM).

TABLE 1

Group of compounds similar to those of formula (I)

| Structure | $EC_{50}$ |
|---|---|
| 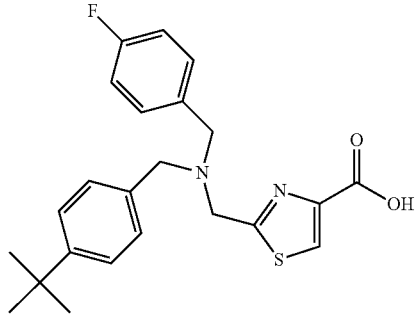 [SMILES: CC(C)(C)c1ccc(CN(Cc2ccc(F)cc2)Cc2nc(C(=O)O)cs2)cc1] | 41.6 μM |
| 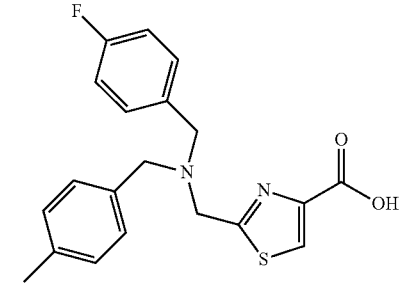 [SMILES: Cc1ccc(CN(Cc2ccc(F)cc2)Cc2nc(C(=O)O)cs2)cc1] | 137 μM |
| 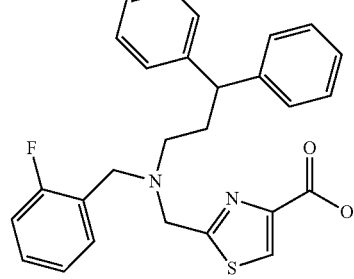 | 10.6 μM |

TABLE 1-continued
Group of compounds similar to those of formula (I)
| Structure | EC$_{50}$ |
|---|---|
| 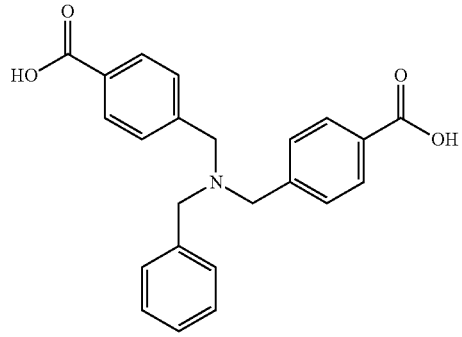 | 18 μM |
| 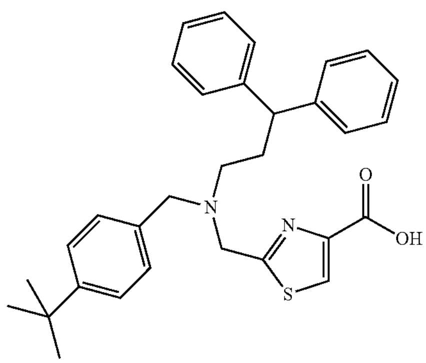 [SMILES: CC(C)(C)c1ccc(CN(CCC(c2ccccc2)c2ccccc2)Cc2nc(C(=O)O)cs2)cc1] | 21.1 μM |
| 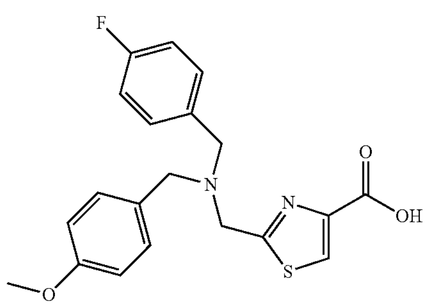 [SMILES: COc1ccc(CN(Cc2ccc(F)cc2)Cc2nc(C(=O)O)cs2)cc1] | 25.6 μM |
| 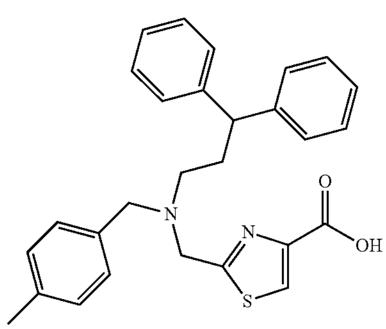 [SMILES: Cc1ccc(CN(CCC(c2ccccc2)c2ccccc2)Cc2nc(C(=O)O)cs2)cc1] | 35.4 μM |
TABLE 1-continued
Group of compounds similar to those of formula (I)
| Structure | EC$_{50}$ |
|---|---|
| 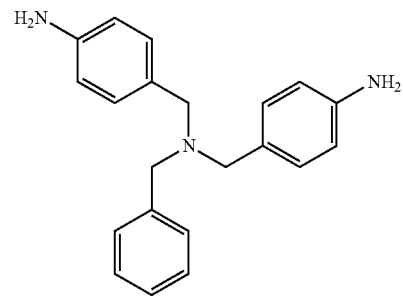 [SMILES: Nc1ccc(CN(Cc2ccccc2)Cc2ccc(N)cc2)cc1] | 29.6 μM |
| 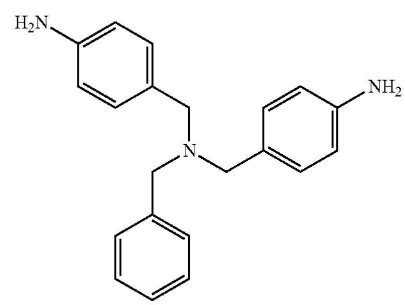 | 3.8 μM |
| 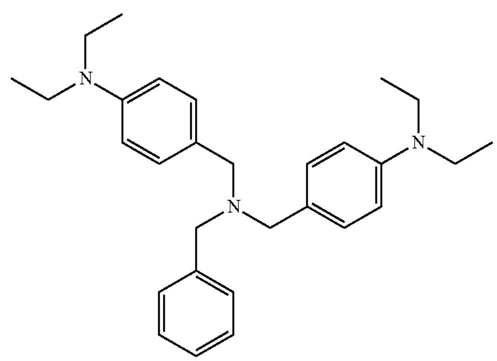 [SMILES: CCN(CC)c1ccc(CN(Cc2ccccc2)Cc2ccc(N(CC)CC)cc2)cc1] | 2.9 μM |
| 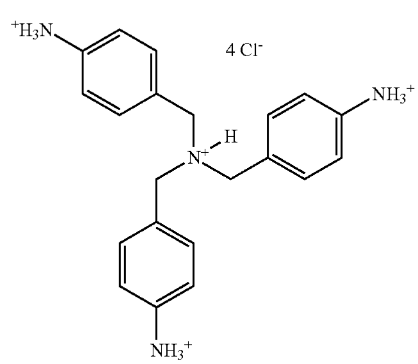 [SMILES: [NH3+]c1ccc(C[NH+](Cc2ccc([NH3+])cc2)Cc2ccc([NH3+])cc2)cc1] | 22.2 μM |

TABLE 1-continued

Group of compounds similar to those of formula (I)

| Structure | EC$_{50}$ |
|---|---|
| 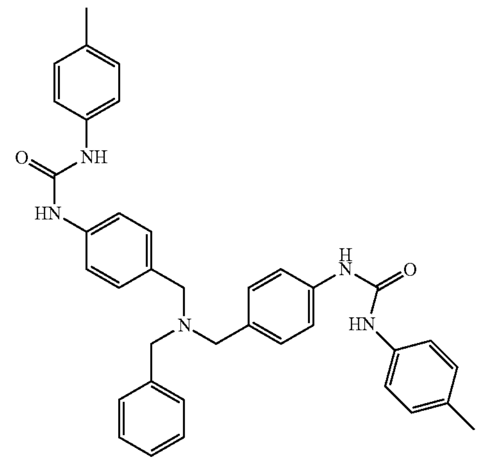 [SMILES: Cc1ccc(NC(=O)Nc2ccc(CN(Cc3ccccc3)Cc3ccc(NC(=O)Nc4ccc(C)cc4)cc3)cc2)cc1] | 2.5 μM |
| 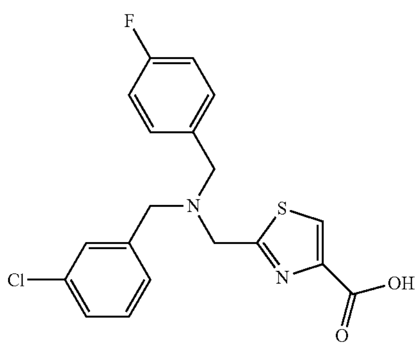 [SMILES: O=C(O)c1csc(CN(Cc2ccc(F)cc2)Cc2cccc(Cl)c2)n1] | 36.4 μM |
| 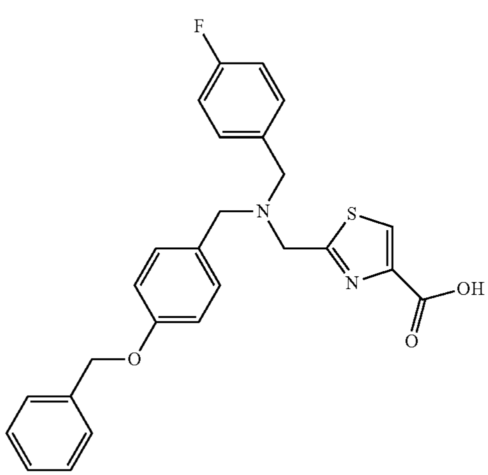 [SMILES: O=C(O)c1csc(CN(Cc2ccc(F)cc2)Cc2ccc(OCc3ccccc3)cc2)n1] | 39.5 μM |
| 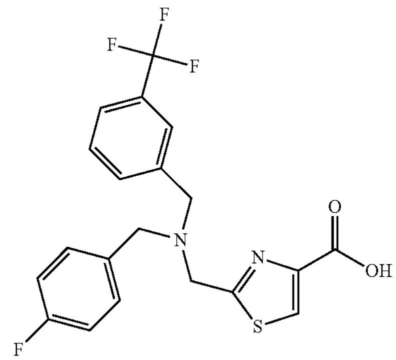 [SMILES: O=C(O)c1csc(CN(Cc2ccc(F)cc2)Cc2cccc(C(F)(F)F)c2)n1] | 60.5 μM |
| 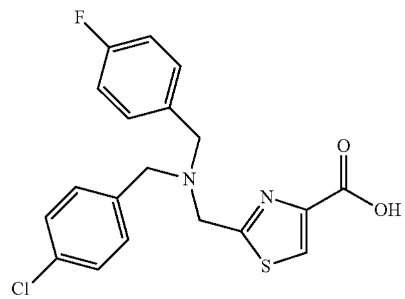 [SMILES: O=C(O)c1csc(CN(Cc2ccc(F)cc2)Cc2ccc(Cl)cc2)n1] | 94.3 μM |
| 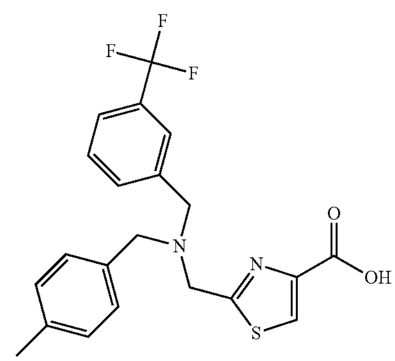 [SMILES: Cc1ccc(CN(Cc2cccc(C(F)(F)F)c2)Cc2nc(C(=O)O)cs2)cc1] | 98.3 μM |
| 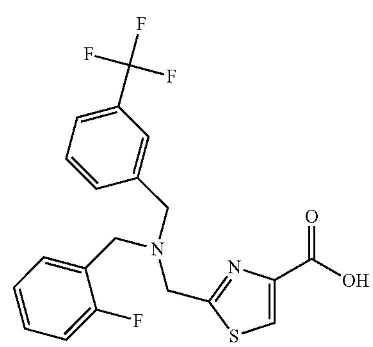 [SMILES: O=C(O)c1csc(CN(Cc2cccc(C(F)(F)F)c2)Cc2ccccc2F)n1] | 215.9 μM |

TABLE 1-continued
Group of compounds similar to those of formula (I)
| Structure | EC$_{50}$ |
|---|---|
| 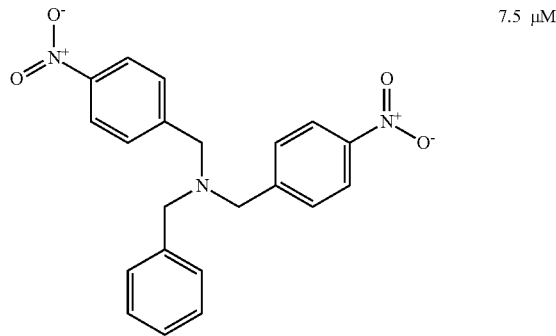 | 7.5 μM |
| 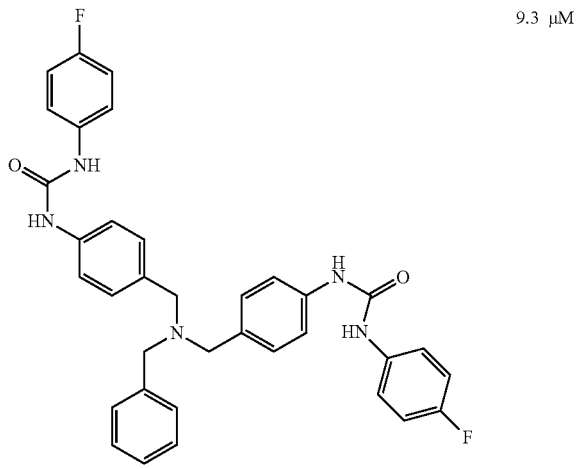 | 9.3 μM |
| 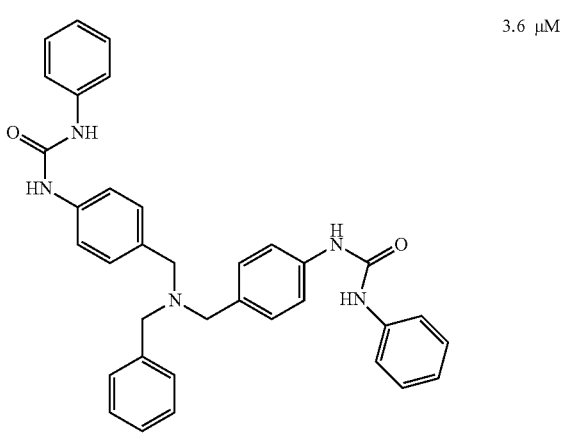 | 3.6 μM |
| | 5.2 μM |
| | 2.0 μM |
The compounds of formula (I) are analogous to the compounds shown above, except that two of the alkylene units linking the aryl/heteroaryl rings are linked so as to form a central, nitrogen containing ring, as shown below:

Hit from Compound Screen

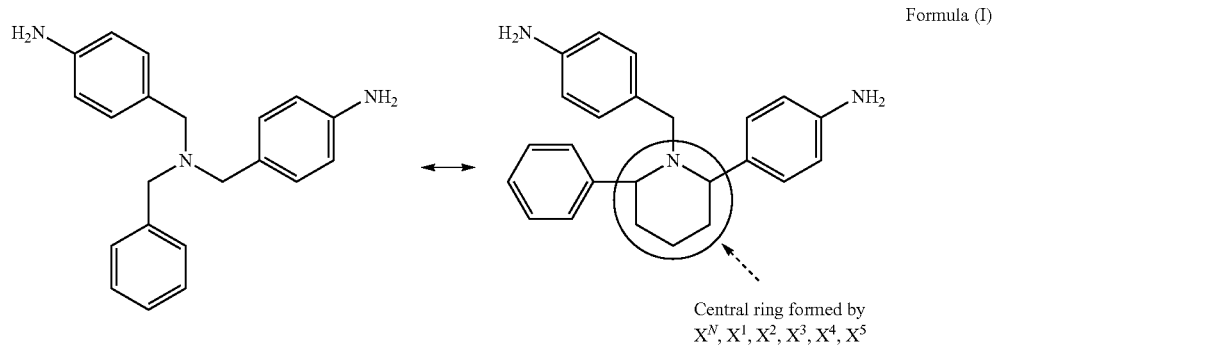

Central ring formed by
$X^N, X^1, X^2, X^3, X^4, X^5$

Formula (I)

Example 2

Synthesis of
N-4-methyl-benzyl-1,2,3,4-tetrahydroisoquinoline 4-methylbenzyl bromide (0.61 g, 3.3 mmol) was added to a stirred suspension of 1,2,3,4-tetrahydroisoquinoline (0.40 g, 3 mmol) and potassium carbonate (0.83 g, 6 mmol) in acetone (30 ml). The stirred mixture was heated to 40° C. for 24 hours. The mixture was cooled to room temperature and filtered. The filtrate was evaporated in vacuum and dichloromethane (50 ml) was added to the residue and washed with water (3×25 ml). The organic layer was dried over magnesium sulfate, filtered and evaporated in vacuum. The product was dried at 40° C. for 24 hours in vacuum. The title compound was isolated as an yellow oil. NMR(CDCl$_3$) (delta): 2.36 (s, 3H), 2.75 (t, 2H), 2.91 (t, 2H), 3.64 (s, 2H), 3.67 (s, 2H), 7.1 (m, 8H). C13 NMR confirmed the identity of the title compound.

Example 3

Synthesis of
N-4-t-butyl-benzyl-1,2,3,4-tetrahydroisoquinoline
hydrochloride salt 4-t-butyl-benzyl bromide (1.21 ml, 6.6 mmol) was added to a stirred suspension of 1,2,3,4-tetrahydroisoquinoline (0.80 g, 6 mmol) and potassium carbonate (1.64 g, 12 mmol) in acetone (60 ml). The stirred mixture was heated to 40° C. for 72 hours. The mixture was cooled to room temperature and filtered. The filtrate was evaporated in vacuum and dichloromethane (50 ml) was added to the residue and washed with water (3×25 ml). The organic layer was dried over magnesium sulfate, filtered and evaporated in vacuum. The residue was dissolved in dichloromethane (3 ml). HCl (2 M) in diethyl ether was added to the stirred solution of dichloromethane solution at room temperature until no more precipitate was formed. The mixture filtered and the solid material dried at 40° C. for 24 hours in vacuum. The title compound was isolated as a white solid material (548 mg). H1-NMR(DMSO-D6) confirmed the identity of the title compound.

Example 4

Synthesis of
N-4-benzyl-1,2,3,4-tetrahydroisoquinoline
hydrochloride salt 4-benzyl bromide (1.62 ml, 6.6 mmol) was added to a stirred suspension of 1,2,3,4-tetrahydroisoquinoline (0.85 g, 6 mmol) and potassium carbonate (3.31 g, 24 mmol) in acetone (60 ml). The stirred mixture was heated to 40° C. for 24 hours. The mixture was cooled to room temperature and filtered. The filtrate was evaporated in vacuum and dichloromethane (50 ml) was added to the residue and washed with water (3×25 ml). The organic layer was dried over magnesium sulfate, filtered and evaporated in vacuum. The residue was dissolved in dichloromethane (3 ml). HCl (2 M) in diethyl ether was added to the stirred solution of dichloromethane solution at room temperature until no more precipitate was formed. The mixture filtered and the solid material dried at 40° C. for 24 hours in vacuum. The title compound was isolated as a light red solid (1.16 g). H1-NMR(DMSO-D6) confirmed the identity of the title compound.

Example 5

Synthesis of
N-4-bromo-benzyl-1,2,3,4-tetrahydroisoquinoline
hydrochloride salt 4-bromobenzyl bromide (0.82 g, 3.3 mmol) was added to a stirred suspension of 1,2,3,4-tetrahydroisoquinoline (0.38 ml, 3 mmol) and potassium carbonate (0.83 g, 6 mmol) in acetone (30 ml). The stirred mixture was heated to 40° C. for 24 hours. The mixture was cooled to room temperature and filtered. The filtrate was evaporated under vacuum and dichloromethane (50 ml) was added to the residue and washed with water (3×25 ml). The organic layer was dried over magnesium sulfate, filtered and evaporated in vacuum. The residue was dissolved in dichloromethane (3 ml). HCl (2 M) in diethyl ether was added to the stirred solution of dichloromethane solution at room temperature until no more precipitate was formed. The mixture filtered and the solid material dried at 40° C. for 24 hours in vacuum. The title compound was isolated as a light brown powder (533 mg). H1-NMR(DMSO-D6) confirmed the identity of the title compound.

Example 6

Synthesis of
N-4-nitro-benzyl-1,2,3,4-tetrahydroisoquinoline 4-nitrobenzyl bromide (0.71 g, 3.3 mmol) was added to a stirred suspension of 1,2,3,4-tetrahydroisoquinoline (0.38 ml, 3 mmol) and potassium carbonate (0.83 g, 6 mmol) in acetone (30 ml). The stirred mixture was heated to 40° C. for 24 hours. The mixture was cooled to room temperature and filtered. The filtrate was evaporated under vacuum and dichloromethane (50 ml) was added to the residue and washed with water (3×25 ml). The organic layer was dried over magnesium sulfate, filtered and evaporated under vacuum. The residue was dissolved in dichloromethane (3 ml). HCl (2 M) in diethyl ether was added to the stirred solution of dichloromethane solution at room temperature until no more precipitate was formed. The mixture filtered and the solid material dried at 40° C. for 24 hours in vacuum. The title compound was isolated as a red/brown powder (550 mg). H1-NMR(DMSO-D6) confirmed the identity of the title compound.

Example 7

Synthesis of N-benzyl-isoindoline hydrochloride salt 1,2-alpha,alpha'-dibromo-o-xylene (1.56 g, 6 mmol) and benzylamine (0.63 g, 6 mmol) were dissolved in dioxane (15 ml). Sodium hydroxide (0.54 g, 13.5 mmol) was added. The mixture was stirred at room temperature for one hour. The mixture was filtered and the filtrate was dissolved in dichloromethane (3 ml). HCl (2 M) in diethyl ether was added to the stirred solution of dichloromethane solution at room temperature until no more precipitate was formed. The mixture filtered and the solid material dried at 40° C. for 24 hours in vacuum. The title compound was isolated as a dark oily residue which crystallized to a green solid material (400 mg). H1-NMR(DMSO-D6) confirmed the identity of the title compound.

Example 8

Synthesis of N-4-methylpyridyl-isoindoline

The title compound was prepared from 1,2-alpha,alpha'-dibromo-o-xylene and 4-methylpyridyl amine as described in the synthesis of N-benzyl-isoindoline. The product was purified by flash chromatography and isolated as a dark oil. H1-NMR(CDCl$_3$) confirmed the identity of the title compound.

Example 9

Synthesis of N-3-methylpyridyl-isoindoline

The title compound was prepared from 1,2-alpha,alpha'-dibromo-o-xylene and 3-methylpyridyl amine as described in the synthesis of N-benzyl-isoindoline. The product was purified by flash chromatography and isolated as a dark oil. H1-NMR(CDCl$_3$) confirmed the identity of the title compound.

Example 10

Synthesis of N-4-methylpyridyl-1,2,3,4-tetrahydroisoquinoline

The title compound was prepared from 1,2,3,4-tetrahydroisoquinoline and 4-(aminomethyl)pyridine as described in the synthesis of N-4-methyl-benzyl-1,2,3,4-tetrahydroisoquinoline. The product was purified by flash chromatography and isolated as a dark oil. H1-NMR(CDCl$_3$) confirmed the identity of the title compound.

Example 11

Pharmacological Testing of the Compounds of Examples 2-10

The compounds of Examples 2-10 were tested for pharmacological activity using the Binding Assay described above. The compounds of Examples 2-10 were dissolved in DMSO to a concentration of 10 mM, diluted in aqueous solution and tested for their ability to disrupt the AKAP18δ-PLB interaction at different concentrations in the AlphaScreen binding assay as described above.

Signal intensity was recorded at each concentration of compound. Maximal signal representing full interaction between AKAP186 and PLB at 0 μM compound was set to 100% and loss of signal (due to compound disruption of the protein-protein interaction) plotted against log [conc compound] and curves fitted in SigmaPlot (see FIGS. 2a-2i). The concentration of compound that produced a half-maximal disruption of the signal and thereby the AKAP18δ-PLB interaction was reported as the EC$_{50}$ for each compound (see Table 2 below).

TABLE 2

EC$_{50}$ data for compounds 2-10

| Compound No. | Structure | EC$_{50}$ |
|---|---|---|
| 2 | 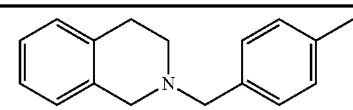 | 142 μM |
| 3 | 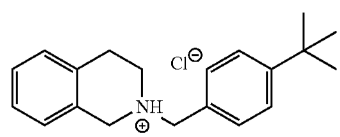 [SMILES: CC(C)(C)c1ccc(C[NH+]2CCc3ccccc3C2)cc1 ; [Cl-]] | 55.3 μM |
| 4 | 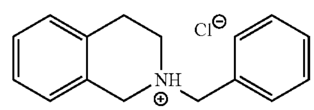 [SMILES: c1ccc(C[NH+]2CCc3ccccc3C2)cc1 ; [Cl-]] | 6.5 mM |
| 5 | 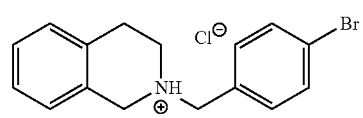 [SMILES: Brc1ccc(C[NH+]2CCc3ccccc3C2)cc1 ; [Cl-]] | 64.5 μM |
| 6 | 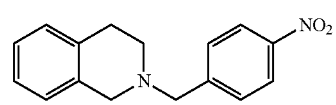 [SMILES: O=[N+]([O-])c1ccc(CN2CCc3ccccc3C2)cc1] | 71.5 μM |
| 7 | 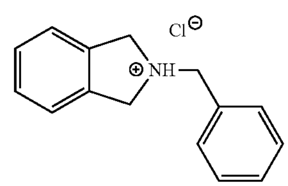 [SMILES: c1ccc(C[NH+]2Cc3ccccc3C2)cc1 ; [Cl-]] | 207 μM |
| 8 | 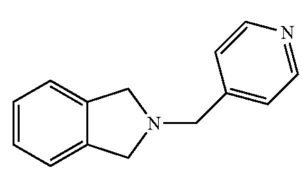 [SMILES: c1ccc2c(c1)CN(Cc1ccncc1)C2] | 71.8 μM |

TABLE 2-continued

EC$_{50}$ data for compounds 2-10

| Compound No. | Structure | EC$_{50}$ |
|---|---|---|
| 9 | [structure: N-(pyridin-4-ylmethyl)-1,2,3,4-tetrahydroisoquinoline] | 113 µM |
| 10 | [structure: 2-(pyridin-3-ylmethyl)isoindoline] | 47.8 µM |

As evident from FIGS. 2a through 2i and Table 2, the group of N-4-benzyl-1,2,3,4-tetrahydroisoquinolines (compounds 2-6) produced EC$_{50}$ values ranging from 55 µM to 6.5 mM. Notably, N-4-benzyl-1,2,3,4-tetrahydroisoquinoline (compound 4) without any substituent on the N-4-benzyl-group returned a single-digit mM EC$_{50}$ value whereas compounds with a methyl-, t-butyl-, bromo- or nitro-substituent in para position on the N-4-benzyl-group returned EC$_{50}$ values from 55 to 142 µM, with the smaller methyl group having the highest EC$_{50}$.

Substituted isoindoline compounds (compounds 7, 8 and 10) returned EC$_{50}$ values from 47 to 206 µM. An N-benzyl-substituted isoindoline (compound 7) gave an EC$_{50}$ of 206 µM, substitutions with a heterocyclic N-3- or N-4-methylpyridyl-group gave lower EC$_{50}$ values of 47 and 71 µM.

Compound 10, combining the 1,2,3,4-tetrahydroisoquinoline group with the heterocyclic N-4-methylpyridyl-group, gave an EC$_{50}$ value of 113 µM.

The invention claimed is:

1. A method of treating cardiovascular disease, the method comprising administering to a human or non-human animal in need thereof a compound according to formula (I), or a pharmaceutically acceptable salt thereof, including all stereoisomers and tautomers thereof:

[Formula (I) structure]

wherein $X^N$ denotes N;

$L^1$ denotes C(=O)C$_1$-C$_3$-alkylene optionally substituted with one phenyl, or C$_1$-C$_4$-alkylene optionally substituted with one phenyl;

$G^2$ denotes H or $L^2Ar^2$;

$L^2$ denotes a bond or C$_1$-C$_3$-alkylene optionally substituted with one phenyl;

$X^1$ denotes CH or CH$_2$;

a and b independently denote 0 or 1;

$X^2G$ denotes C=O, C-$L^3$-Ar$^3$, CH-$L^3$-Ar$^3$ or

[ring structure]

in which $X^{2a}$—$X^{2b}$ correspond to $X^2$ in the structure of formula (I);

c is 0 or 1;

$X^{2a}$, $X^{2b}$, $X^6$, $X^7$, $X^8$, and $X^9$ together form a 5-6 membered heteroaryl optionally substituted with —C(=O)Z or one or more R; or a 6 membered aryl optionally substituted with one or more R;

$L^3$ denotes a bond or C$_1$-C$_3$-alkylene optionally substituted with one phenyl;

$X^3$ denotes a bond, $Y^1$, $Y^1$—$Y^2$, $Y^1$—$Y^3$—$Y^2$, or

[structure with $L^4Ar^4$, $L^5Ar^5$, $L^6Ar^6$]

$L^4$ and $L^6$ independently denote a bond or C$_1$-C$_3$-alkylene optionally substituted with one phenyl;

$L^5$ denotes C(=O)C$_1$-C$_3$-alkylene optionally substituted with one phenyl, or C$_1$-C$_4$-alkylene optionally substituted with one phenyl;

$Y^1$, $Y^2$ and $Y^3$ independently denote CH, CH$_2$, N, NZ$^x$ or O, provided that when one of $Y^1$, $Y^2$ or $Y^3$ denotes O, the remainder denote CH, CH$_2$ or N;

$Z^x$ denotes H, C$_1$-C$_4$-alkyl, C(=O)H, C(=O)C$_1$-C$_4$-alkyl, or C(=O)OR$_z$;

$X^4$ denotes C, CH or N;

$X^5$ denotes CH or CH$_2$;

provided that $X^N$, $X^1$, $X^2$, $X^3$, $X^4$, $X^5$ together denote a 5-6 membered heterocycle or 5-6 membered heteroaryl;

Ar$^1$, Ar$^2$, Ar$^3$, Ar$^4$, Ar$^5$ and Ar$^6$ independently denote a 5-10 membered heteroaryl optionally substituted with —C(=O)Z or one or more R; or a 6-10 membered aryl optionally substituted with one or more R;

Z denotes OR$^a$ or NR$^b$R$^c$;

R$^a$ denotes H, C$_1$-C$_4$-alkyl, C$_3$-C$_6$-cycloalkyl, C$_2$-C$_4$-alkylene-O—C$_1$-C$_4$-alkyl, C$_2$-C$_4$-alkylene-CN; C$_1$-C$_4$-alkyl substituted with one or two Ar$^7$;

R$^b$ denotes H, C$_1$-C$_4$-alkyl, C$_3$-C$_6$-cycloalkyl, C$_2$-C$_4$-alkylene-CN; C$_2$-C$_4$-alkylene-O—C$_1$-C$_4$-alkyl; or C$_1$-C$_4$-alkyl substituted with one or two Ar$^7$;

R$^c$ denotes H, C$_1$-C$_8$ alkyl, C$_3$-C$_6$-cycloalkyl, Ar$^7$, C$_1$-C$_4$-alkyl substituted with one or two Ar$^7$; OH, O—C$_1$-C$_4$-alkyl, C$_2$-C$_4$-alkyl-O—C$_1$-C$_4$-alkyl, or C$_2$-C$_4$-alkyl-NR$^a$R$^a$; or together NR$^b$R$^c$ denotes

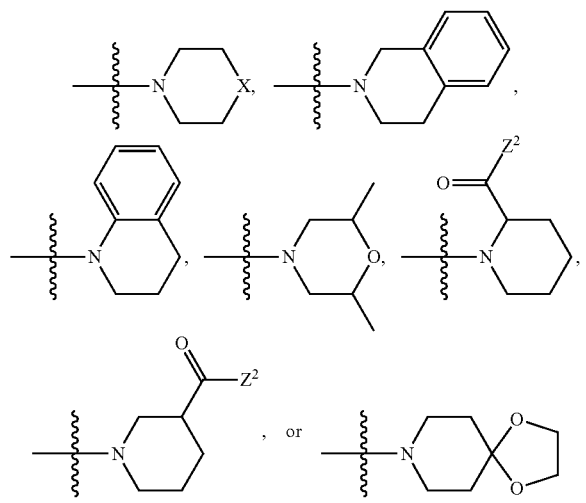

wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_3$-$C_6$-cycloalkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H, $C_1$-$C_4$-alkyl or $C_3$-$C_6$-cycloalkyl;

R independently denotes F, Cl, Br, I, $C_1$-$C_4$-haloalkyl, $OR^1$, $SR^1$, $NO_2$, $NR^2R^3$, $R^4$, C(=O)Y, $SO_3H$, $C_1$-$C_4$-alkyl, $C_1$-$C_4$-alkyl-phenyl, a 5-membered heteroaryl; or a phenyl substituted with a 5-membered heteroaryl;

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl; or $NR^2R^3$ denotes —NHC(=O)—$NHAr^8$; or together two adjacent $NR^2R^3$ groups denote —$NR^2$—CH=N— or —$NR^2$—$CH_2$—$NR^2$—; or together with an adjacent $OR^1$ group, $NR^2R^3$ denotes —$NR^2$—$CH_2$—O— or —N=CH—O—; or together with an adjacent $SR^1$ group, $NR^2R^3$ denotes —$NR^2$—$CH_2$—S— or —N=CH—S—;

$Ar^8$ denotes phenyl optionally substituted with $R^h$;

$R^h$ denotes halogen or $C_1$-$C_4$ alkyl;

$R^4$ denotes $C_1$-$C_4$-alkyl; or together with an adjacent $OR^1$ group, $R^4$ denotes —$CH_2CH_2$—O—; or together two adjacent $R^4$ groups denote —$(CH)_4$— or —$(CH_2)_4$—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

2. The method of claim 1, wherein the compound has formula (Ib):

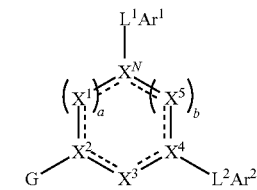

(Ib)

wherein $X^N$ denotes N;

$L^1$ denotes C(=O)$C_1$-$C_3$-alkylene optionally substituted with one phenyl, or $C_1$-$C_4$-alkylene optionally substituted with one phenyl;

$L^2$ denotes a bond or $C_1$-$C_3$-alkylene optionally substituted with one phenyl;

$X^1$ denotes CH or $CH_2$;

a and b independently denote 0 or 1;

$X^2G$ denotes C=O, C-$L^3$-$Ar^3$, or

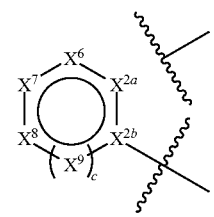

in which $X^{2a}$—$X^{2b}$ correspond to $X^2$ in the structure of formula (Ib);

c is 0 or 1;

$X^{2a}$, $X^{2b}$, $X^6$, $X^7$, $X^8$, and $X^9$ together form a 5-6 membered heteroaryl optionally substituted with —C(=O)Z or one or more R; or a 6 membered aryl optionally substituted with one or more R;

$L^3$ denotes a bond or $C_1$-$C_3$-alkylene optionally substituted with one phenyl;

$X^3$ denotes a bond, $Y^1$, $Y^1$—$Y^2$, $Y^1$—$Y^3$—$Y^2$, or

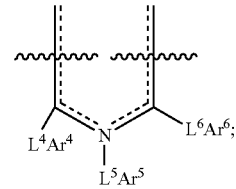

$L^4$ and $L^6$ independently denote a bond or $C_1$-$C_3$-alkylene optionally substituted with one phenyl;

$L^5$ denotes C(=O)$C_1$-$C_3$-alkylene optionally substituted with one phenyl, or $C_1$-$C_4$-alkylene optionally substituted with one phenyl;

$Y^1$, $Y^2$ and $Y^3$ independently denote CH, $CH_2$, N, $NZ^x$ or O;

$Z^x$ denotes H, $C_1$-$C_4$-alkyl, C(=O)H, C(=O)$C_1$-$C_4$-alkyl, or C(=O)$OR^z$;

$X^4$ denotes C, CH or N;

$X^5$ denotes CH or $CH_2$;

provided that $X^N$, $X^1$, $X^2$, $X^3$, $X^4$, $X^5$ together denote a 5-6 membered heterocycle or 5-6 membered heteroaryl;

$Ar^1$, $Ar^2$, $Ar^3$, $Ar^4$, $Ar^5$ and $Ar^6$ independently denote a 5-10 membered heteroaryl optionally substituted with —C(=O)Z or one or more R; or a 6-10 membered aryl optionally substituted with one or more R;

Z denotes $OR^a$ or $NR^bR^c$;

$R^a$ denotes H or $C_1$-$C_4$-alkyl;

$R^b$ denotes H, $C_1$-$C_4$-alkyl, $C_2$-$C_4$-alkyl-CN; or $C_1$-$C_4$-alkyl substituted with one or two $Ar^7$;

$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

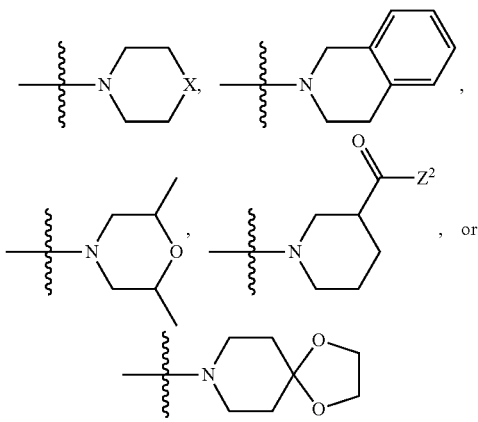

wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H or $C_1$-$C_4$-alkyl;

R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl, 5-tetrazolyl or

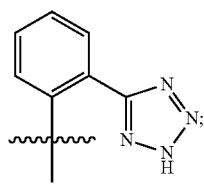 [SMILES: *c1ccccc1-c1nn[nH]n1]

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl;

$R^4$ denotes $C_1$-$C_4$-alkyl; or together with an adjacent $OR^1$ group, $R^4$ denotes —$CH_2CH_2$—O—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$-cycloalkyl.

3. The method of claim 1 wherein
a and b denote 0;
$X^2G$ denotes C=O, C-$L^3$-$Ar^3$ or CH-$L^3$-$Ar^3$;
$X^3$ denotes $Y^1$—$Y^2$, or $Y^1$—$Y^3$—$Y^2$; and
$X^4$ denotes C or CH.

4. The method of claim 1 wherein
a and b denote 0;
$L^1$ denotes $C_1$-$C_4$-alkylene optionally substituted with one phenyl;
$X^2G$ denotes CH-$L^3$-$Ar^3$;
$X^3$ denotes $Y^1$—$Y^2$ or $Y^1$—$Y^3$—$Y^2$;
$Y^1$, $Y^2$ and $Y^3$ independently denote $CH_2$, $NZ^x$ or O, provided that at least one of $Y^1$, $Y^2$ or $Y^3$ denotes $CH_2$ and that when one of $Y^1$, $Y^2$ or $Y^3$ denotes O, the remainder denote $CH_2$; and
$X^4$ denotes CH.

5. The method of claim 1 wherein $Ar^1$, $Ar^2$ and $Ar^3$ independently denote a 5- or 6-membered heteroaryl optionally substituted with —C(=O)Z or one or more R; or a phenyl optionally substituted with one or more R.

6. The method of claim 1 wherein $Ar^1$ denotes phenyl optionally substituted with one or two R.

7. The method of claim 1 wherein $Ar^2$ denotes phenyl optionally substituted with one or two R;

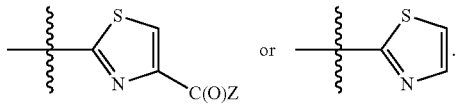

8. The method of claim 1 wherein $L^1$ denotes $C_1$-$C_3$-alkylene optionally substituted with one phenyl; and
$L^2$ and $L^3$ independently denote a bond or $C_1$-$C_2$-alkylene optionally substituted with one phenyl.

9. The method of claim 1 wherein $Ar^3$ denotes phenyl optionally substituted with one or two R; pyridyl, or 2-furyl.

10. The method of claim 1 wherein $L^3$ denotes a bond, —$CH_2$—, —$CH(CH_3)$— or —$CH_2CH(C_6H_5)$—.

11. The method of claim 1 wherein $R^b$ denotes H or $C_1$-$C_4$-alkyl; and
$R^c$ denotes H, $C_1$-$C_4$ alkyl, cyclopropyl, cyclohexyl, $Ar^7$, $C_1$-$C_4$-alkyl substituted with one or two $Ar^7$; OH, or O—$C_1$-$C_4$-alkyl;
or together $NR^bR^c$ denotes

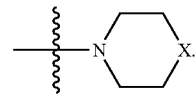

12. The method of claim 1 wherein $Z^1$ denotes H, C(=O)H, C(=O)$C_1$-$C_4$-alkyl, C(=O)$OR^z$, $Ar^7$, $C_1$-$C_4$-alkyl, or $C_1$-$C_4$-alkyl substituted with one or two $Ar^7$.

13. The method of claim 1 wherein R independently denotes F, Cl, $CF_3$, $OR^1$, $NO_2$, $NR^2R^3$, $R^4$, C(=O)Y, $C_1$-$C_4$-alkyl, $C_1$-$C_4$-alkyl-phenyl, or

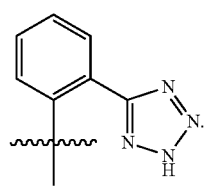 [SMILES: *c1ccccc1-c1nn[nH]n1]

14. The method of claim 1 wherein R independently denotes F, Cl, CF$_3$, OR$^1$, C(=O)Y, C$_1$-C$_4$-alkyl or C$_1$-C$_4$-alkyl-phenyl.

15. The method of claim 1 wherein compound has formula (Ic')

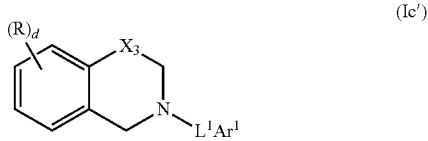

wherein

L$^1$ denotes C(=O)C$_1$-C$_3$-alkylene optionally substituted with one phenyl, or C$_1$-C$_4$-alkylene optionally substituted with one phenyl;

d denotes an integer from 0 to 4;

X$^3$ denotes a CH$_2$ or a bond;

Ar$^1$ denotes a 5-10 membered heteroaryl optionally substituted with —C(=O)Z or one or more R; or a 6-10 membered aryl optionally substituted with one or more R;

Z denotes OR$^a$ or NR$^b$R$^c$;

R$^a$ denotes H, C$_1$-C$_4$-alkyl, C$_3$-C$_6$-cycloalkyl, C$_2$-C$_4$-alkylene-O—C$_1$-C$_4$-alkyl, C$_2$-C$_4$-alkylene-CN; C$_1$-C$_4$-alkyl substituted with one or two Ar$^7$;

R$^b$ denotes H, C$_1$-C$_4$-alkyl, C$_3$-C$_6$-cycloalkyl, C$_2$-C$_4$-alkylene-CN; C$_2$-C$_4$-alkylene-O—C$_1$-C$_4$-alkyl; or C$_1$-C$_4$-alkyl substituted with one or two Ar$^7$;

R$^c$ denotes H, C$_1$-C$_8$ alkyl, C$_3$-C$_6$-cycloalkyl, Ar$^7$, C$_1$-C$_4$-alkyl substituted with one or two Ar$^7$; OH, O—C$_1$-C$_4$-alkyl, C$_2$-C$_4$-alkyl-O—C$_1$-C$_4$-alkyl, or C$_2$-C$_4$-alkyl-NR$^a$R$^a$; or together NR$^b$R$^c$ denotes

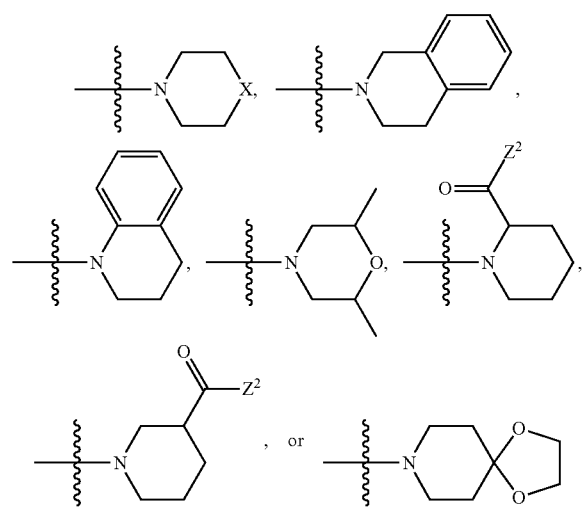

wherein X denotes CHZ$^1$, O, or NZ$^1$;

Z$^1$ denotes H, C(=O)H, C(=O)C$_1$-C$_4$-alkyl, C(=O)OR$^z$, Ar$^7$, C$_1$-C$_4$-alkyl, C$_3$-C$_6$-cycloalkyl, C$_1$-C$_4$-alkyl substituted with one or two Ar$^7$; C$_2$-C$_4$—NR$^d$R$^e$, or C$_2$-C$_4$—OR$^f$;

Z$^2$ denotes OR$^a$ or NR$^g$R$^g$;

Ar$^7$ denotes 5-6 membered heteroaryl; or phenyl optionally substituted with one or more R;

R$^d$, R$^e$ and R$^f$ independently denote H or C$_1$-C$_4$-alkyl;

R$^g$ denotes R$^b$;

R$^z$ denotes H, C$_1$-C$_4$-alkyl or C$_3$-C$_6$-cycloalkyl;

R independently denotes F, Cl, Br, I, C$_1$-C$_4$-haloalkyl, OR$^1$, SR$^1$, NO$_2$, NR$^2$R$^3$, R$^4$, C(=O)Y, SO$_3$H, C$_1$-C$_4$-alkyl, C$_1$-C$_4$-alkyl-phenyl, a 5-membered heteroaryl; or a phenyl substituted with a 5-membered heteroaryl;

R$^1$ denotes H, C$_1$-C$_4$-alkyl or C$_1$-C$_4$-alkyl-phenyl; or together two adjacent OR$^1$ groups denote —O—CH$_2$—O—;

R$^2$ and R$^3$ independently denote H or C$_1$-C$_4$-alkyl; or NR$^2$R$^3$ denotes —NHC(=O)—NHAr$^8$; or together two adjacent NR$^2$R$^3$ groups denote —NR$^2$—CH—N— or —NR$^2$—CH$_2$—NR$^2$—; or together with an adjacent OR$^1$ group, NR$^2$R$^3$ denotes —NR$^2$—CH$_2$—O— or —N—CH—O—; or together with an adjacent SR$^1$ group, NR$^2$R$^3$ denotes —NR$^2$—CH$_2$—S— or —N—CH—S—;

Ar$^8$ denotes phenyl optionally substituted with R$^h$;

R$^h$ denotes halogen or C$_1$-C$_4$ alkyl;

R$^4$ denotes C$_1$-C$_4$-alkyl; or together with an adjacent OR$^1$ group, R$^4$ denotes —CH$_2$CH$_2$—O—; or together two adjacent R$^4$ groups denote —(CH)$_4$— or —(CH$_2$)$_4$—;

Y denotes OR$^5$ or NR$^6$R$^7$;

R$^5$ denotes H or C$_1$-C$_4$-alkyl;

R$^6$ and R$^7$ independently denote H, C$_1$-C$_8$-alkyl or C$_3$-C$_6$ cycloalkyl.

16. The method of claim 15, wherein

L$^1$ denotes —CH$_2$;

Ar$^1$ denotes phenyl optionally substituted with one or two R; pyridyl; 2-furyl;

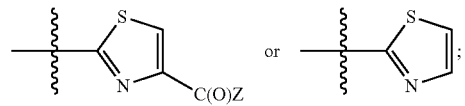

Z denotes OR$^a$ or NR$^b$R$^c$;

R$^a$ denotes H or C$_1$-C$_4$-alkyl;

R$^b$ denotes H or C$_1$-C$_4$-alkyl; and

R$^c$ denotes H, C$_1$-C$_4$ alkyl, cyclopropyl, cyclohexyl, Ar$^7$, C$_1$-C$_4$-alkyl substituted with one or two Ar$^7$; OH, or O—C$_1$-C$_4$-alkyl;

or together NR$^b$R$^c$ denotes

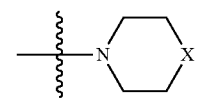

X denotes CHZ$^1$, O, or NZ$^1$;

Z$^1$ denotes H, C(=O)H, C(=O)C$_1$-C$_4$-alkyl, C(=O)OR$^z$, Ar$^7$, C$_1$-C$_4$-alkyl, or C$_1$-C$_4$-alkyl substituted with one or two Ar$^7$;

Z$^2$ denotes OR$^a$ or NR$^g$R$^g$;

Ar$^7$ denotes phenyl optionally substituted with one or two R;

R$^d$, R$^e$ and R$^f$ independently denote H or C$_1$-C$_4$-alkyl;

R$^g$ denotes R$^b$;

R$^z$ denotes H or C$_1$-C$_4$-alkyl;

R independently denotes F, Cl, CF$_3$, OR$^1$, C(=O)Y, C$_1$-C$_4$-alkyl, C$_1$-C$_4$-alkyl-phenyl or

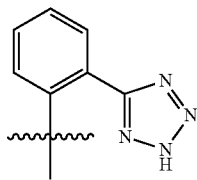 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.

17. The method of claim 15, wherein
$L^1$ denotes —$CH_2$;
$Ar^1$ denotes phenyl optionally substituted with one or two R; pyridyl;
R independently denotes F, Cl, $CF_3$, $OR^1$, C(=O)Y, $C_1$-$C_4$-alkyl, $C_1$-$C_4$-alkyl-phenyl or

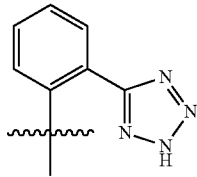 [SMILES: *c1ccccc1-c1nn[nH]n1]

$R^1$ denotes H, $C_1$-$C_4$-alkyl or $C_1$-$C_4$-alkyl-phenyl; or
together two adjacent $OR^1$ groups denote —O—$CH_2$—O—;
$R^2$ and $R^3$ independently denote H or $C_1$-$C_4$-alkyl;
$R^4$ denotes $C_1$-$C_4$-alkyl; or
together with an adjacent $OR^1$ group, $R^4$ denotes —$CH_2CH_2$—O—;
Y denotes $OR^5$ or $NR^6R^7$;
$R^5$ denotes H or $C_1$-$C_4$-alkyl;
$R^6$ and $R^7$ independently denote H and $C_1$-$C_6$-alkyl.

18. The method of claim 1 wherein the compound contains at least one group capable of acting as a hydrogen bond donor, and/or at least one group capable of acting as a hydrogen bond acceptor.

19. The method according to claim 1 wherein the cardiovascular disease is myocardial infarction or congestive heart failure.

20. A pharmaceutical composition comprising a compound according to formula (I), or a pharmaceutically acceptable salt thereof, including all stereoisomers and tautomers thereof, and one or more pharmaceutically acceptable excipients and/or diluents:

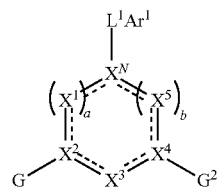

(I)

wherein
$X^N$ denotes N;
$L^1$ denotes C(=O)$C_1$-$C_3$-alkylene optionally substituted with one phenyl, or $C_1$-$C_4$-alkylene optionally substituted with one phenyl;
$G^2$ denotes H or $L^2Ar^2$;
$L^2$ denotes a bond or $C_1$-$C_3$-alkylene optionally substituted with one phenyl;
$X^1$ denotes CH or $CH_2$;
a and b independently denote 0 or 1;
$X^2G$ denotes C=O, C-$L^3$-$Ar^3$, CH-$L^3$-$Ar^3$ or

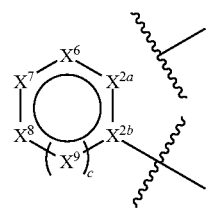

in which $X^{2a}$—$X^{2b}$ correspond to $X^2$ in the structure of formula (I);
c is 0 or 1;
$X^{2a}$, $X^{2b}$, $X^6$, $X^7$, $X^8$, and $X^9$ together form a 5-6 membered heteroaryl optionally substituted with —C(=O)Z or one or more R; or a 6 membered aryl optionally substituted with one or more R;
$L^3$ denotes a bond or $C_1$-$C_3$-alkylene optionally substituted with one phenyl;
$X^3$ denotes a bond, $Y^1$, $Y^1$—$Y^2$, $Y^1$—$Y^3$—$Y^2$, or

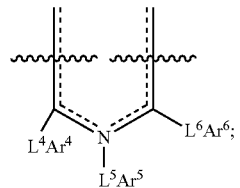

$L^4$ and $L^6$ independently denote a bond or $C_1$-$C_3$-alkylene optionally substituted with one phenyl;
$L^5$ denotes C(=O)$C_1$-$C_3$-alkylene optionally substituted with one phenyl, or $C_1$-$C_4$-alkylene optionally substituted with one phenyl;
$Y^1$, $Y^2$ and $Y^3$ independently denote CH, $CH_2$, N, $NZ^x$ or O, provided that when one of $Y^1$, $Y^2$ or $Y^3$ denotes O, the remainder denote CH, $CH_2$ or N;
$Z^x$ denotes H, $C_1$-$C_4$-alkyl, C(=O)H, C(=O)$C_1$-$C_4$-alkyl, or C(=O)$OR_z$;
$X^4$ denotes C, CH or N;
$X^5$ denotes CH or $CH_2$;
provided that $X^N$, $X^1$, $X^2$, $X^3$, $X^4$, $X^5$ together denote a 5-6 membered heterocycle or 5-6 membered heteroaryl;

$Ar^1$, $Ar^2$, $Ar^3$, $Ar^4$, $Ar^5$ and $Ar^6$ independently denote a 5-10 membered heteroaryl optionally substituted with —C(=O)Z or one or more R; or a 6-10 membered aryl optionally substituted with one or more R;

Z denotes $OR^a$ or $NR^bR^c$;

$R^a$ denotes H, $C_1$-$C_4$-alkyl, $C_3$-$C_6$-cycloalkyl, $C_2$-$C_4$-alkylene-O—$C_1$-$C_4$-alkyl, $C_2$-$C_4$-alkylene-CN; $C_1$-$C_4$-alkyl substituted with one or two $Ar^7$;

$R^b$ denotes H, $C_1$-$C_4$-alkyl, $C_3$-$C_6$-cycloalkyl, $C_2$-$C_4$-alkylene-CN; $C_2$-$C_4$-alkylene-O—$C_1$-$C_4$-alkyl; or $C_1$-$C_4$-alkyl substituted with one or two $Ar^7$;

$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_3$-$C_6$-cycloalkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H, $C_1$-$C_4$-alkyl or $C_3$-$C_6$-cycloalkyl;

R independently denotes F, Cl, Br, I, $C_1$-$C_4$-haloalkyl, $OR^1$, $SR^1$, $NO_2$, $NR^2R^3$, $R^4$, C(=O)Y, $SO_3H$ $C_1$-$C_4$-alkyl, $C_1$-$C_4$-alkyl-phenyl, a 5-membered heteroaryl; or a phenyl substituted with a 5-membered heteroaryl;

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl; or $NR^2R^3$ denotes —NHC(=O)—$NHAr^8$; or together two adjacent $NR^2R^3$ groups denote —$NR^2$—CH—N— or —$NR^2$—$CH_2$—$NR^2$—; or together with an adjacent $OR^1$ group, $NR^2R^3$ denotes —$NR^2$—$CH_2$—O— or —N—CH—O—; or together with an adjacent $SR^1$ group, $NR^2R^3$ denotes —$NR^2$—$CH_2$—S— or —N—CH—S—;

$Ar^8$ denotes phenyl optionally substituted with $R^h$;

$R^h$ denotes halogen or $C_1$-$C_4$ alkyl;

$R^4$ denotes $C_1$-$C_4$-alkyl; or together with an adjacent $OR^1$ group, $R^4$ denotes —$CH_2CH_2$—O—; or together two adjacent $R^4$ groups denote —(CH)$_4$— or —(CH$_2$)$_4$—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

21. A method of regulating SERCA2 activity in a human or non-human animal, the method comprising administering to a human or non-human animal in need thereof a compound according to formula (I), or a pharmaceutically acceptable salt thereof, including all stereoisomers and tautomers thereof:

(I)

wherein $X^N$ denotes N;

$L^1$ denotes C(=O)$C_1$-$C_3$-alkylene optionally substituted with one phenyl, or $C_1$-$C_4$-alkylene optionally substituted with one phenyl;

$G^2$ denotes H or $L^2Ar^2$;

$L^2$ denotes a bond or $C_1$-$C_3$-alkylene optionally substituted with one phenyl;

$X^1$ denotes CH or $CH_2$;

a and b independently denote 0 or 1;

$X^2G$ denotes C=O, C-$L^3$-$Ar^3$, CH-$L^3$-$Ar^3$ or in which $X^{2a}$—$X^{2b}$ correspond to $X^2$ in the structure of formula (I);

c is 0 or 1;

$X^{2a}$, $X^{2b}$, $X^6$, $X^7$, $X^8$, and $X^9$ together form a 5-6 membered heteroaryl optionally substituted with —C(=O)Z or one or more R; or a 6 membered aryl optionally substituted with one or more R;

$L^3$ denotes a bond or $C_1$-$C_3$-alkylene optionally substituted with one phenyl;

$X^3$ denotes a bond, $Y^1$, $Y^1$—$Y^2$, $Y^1$—$Y^3$—$Y^2$, or $L^4$ and $L^6$ independently denote a bond or $C_1$-$C_3$-alkylene optionally substituted with one phenyl;

$L^5$ denotes C(=O)$C_1$-$C_3$-alkylene optionally substituted with one phenyl, or $C_1$-$C_4$-alkylene optionally substituted with one phenyl;

$Y^1$, $Y^2$ and $Y^3$ independently denote CH, $CH_2$, N, $NZ^x$ or O, provided that when one of $Y^1$, $Y^2$ or $Y^3$ denotes O, the remainder denote CH, $CH_2$ or N;

$Z^x$ denotes H, $C_1$-$C_4$-alkyl, C(=O)H, C(=O)$C_1$-$C_4$-alkyl, or C(=O)$OR_z$;

$X^4$ denotes C, CH or N;

$X^5$ denotes CH or $CH_2$;

provided that $X^N$, $X^1$, $X^2$, $X^3$, $X^4$, $X^5$ together denote a 5-6 membered heterocycle or 5-6 membered heteroaryl;

$Ar^1$, $Ar^2$, $Ar^3$, $Ar^4$, $Ar^5$ and $Ar^6$ independently denote a 5-10 membered heteroaryl optionally substituted with —C(=O)Z or one or more R; or a 6-10 membered aryl optionally substituted with one or more R;

Z denotes $OR^a$ or $NR^bR^c$;

$R^a$ denotes H, $C_1$-$C_4$-alkyl, $C_3$-$C_6$-cycloalkyl, $C_2$-$C_4$-alkylene-O—$C_1$-$C_4$-alkyl, $C_2$-$C_4$-alkylene-CN; $C_1$-$C_4$-alkyl substituted with one or two $Ar^7$;

$R^b$ denotes H, $C_1$-$C_4$-alkyl, $C_3$-$C_6$-cycloalkyl, $C_2$-$C_4$-alkylene-CN; $C_2$-$C_4$-alkylene-O—$C_1$-$C_4$-alkyl; or $C_1$-$C_4$-alkyl substituted with one or two $Ar^7$;

$R^c$ denotes H, $C_1$-$C_8$ alkyl, $C_3$-$C_6$-cycloalkyl, $Ar^7$, $C_1$-$C_4$-alkyl substituted with one or two $Ar^7$; OH, O—$C_1$-$C_4$-alkyl, $C_2$-$C_4$-alkyl-O—$C_1$-$C_4$-alkyl, or $C_2$-$C_4$-alkyl-$NR^aR^a$; or together $NR^bR^c$ denotes

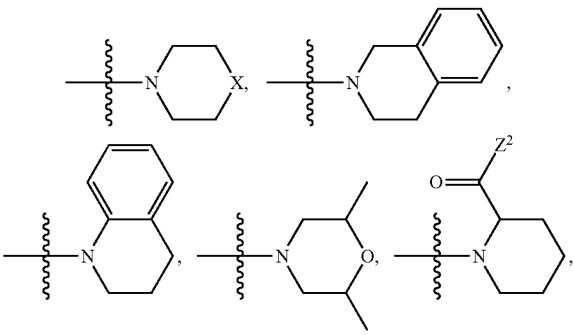

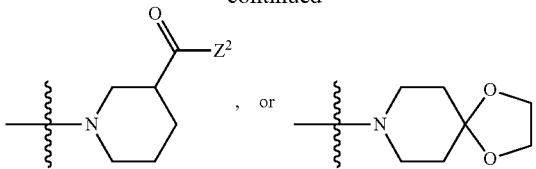

wherein X denotes $CHZ^1$, O, or $NZ^1$;

$Z^1$ denotes H, C(=O)H, C(=O)$C_1$-$C_4$-alkyl, C(=O)$OR^z$, $Ar^7$, $C_1$-$C_4$-alkyl, $C_3$-$C_6$-cycloalkyl, $C_1$-$C_4$-alkyl substituted with one or two $Ar^7$; $C_2$-$C_4$—$NR^dR^e$, or $C_2$-$C_4$—$OR^f$;

$Z^2$ denotes $OR^a$ or $NR^gR^g$;

$Ar^7$ denotes 5-6 membered heteroaryl; or phenyl optionally substituted with one or more R;

$R^d$, $R^e$ and $R^f$ independently denote H or $C_1$-$C_4$-alkyl;

$R^g$ denotes $R^b$;

$R^z$ denotes H, $C_1$-$C_4$-alkyl or $C_3$-$C_6$-cycloalkyl;

R independently denotes F, Cl, Br, I, $C_1$-$C_4$-haloalkyl, $OR^1$, $SR^1$, $NO_2$, $NR^2R^3$, $R^4$, C(=O)Y, $SO_3H$, $C_1$-$C_4$-alkyl, $C_1$-$C_4$-alkyl-phenyl, a 5-membered heteroaryl; or a phenyl substituted with a 5-membered heteroaryl;

$R^1$ denotes H, $C_1$-$C_4$-alkyl or $C_1$-$C_4$-alkyl-phenyl; or together two adjacent $OR^1$ groups denote —O—$CH_2$—O—;

$R^2$ and $R^3$ independently denote H or $C_1$-$C_4$-alkyl; or $NR^2R^3$ denotes —NHC(=O)—$NHAr^8$; or together two adjacent $NR^2R^3$ groups denote —$NR^2$—CH—N— or —$NR^2$—$CH_2$—$NR^2$—; or together with an adjacent $OR^1$ group, $NR^2R^3$ denotes —$NR^2$—$CH_2$—O— or —N—CH—O—; or together with an adjacent $SR^1$ group, $NR^2R^3$ denotes —$NR^2$—$CH_2$—S— or —N—CH—S—;

$Ar^8$ denotes phenyl optionally substituted with $R^h$;

$R^h$ denotes halogen or $C_1$-$C_4$ alkyl;

$R^4$ denotes $C_1$-$C_4$-alkyl; or together with an adjacent $OR^1$ group, $R^4$ denotes —$CH_2CH_2$—O—; or together two adjacent $R^4$ groups denote —$(CH)_4$— or —$(CH_2)_4$—;

Y denotes $OR^5$ or $NR^6R^7$;

$R^5$ denotes H or $C_1$-$C_4$-alkyl;

$R^6$ and $R^7$ independently denote H, $C_1$-$C_8$-alkyl or $C_3$-$C_6$ cycloalkyl.

* * * * *

UNITED STATES PATENT AND TRADEMARK OFFICE
CERTIFICATE OF CORRECTION

PATENT NO. : 9,585,880 B2
APPLICATION NO. : 14/549414
DATED : March 7, 2017
INVENTOR(S) : Jo Klaveness and Kjetil Tasken It is certified that error appears in the above-identified patent and that said Letters Patent is hereby corrected as shown below:

At Column 10, Lines 30-35:

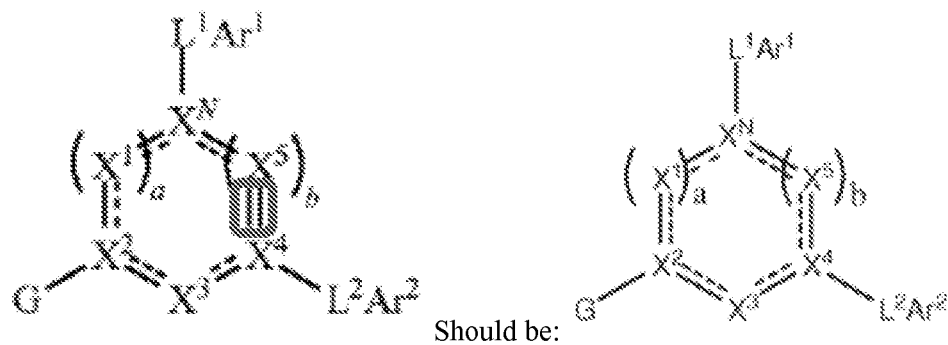
Should be:

At Column 16, Lines 40-45:

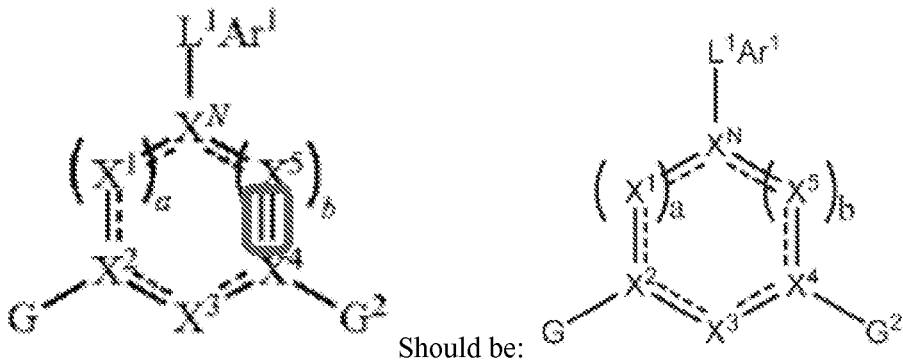
Should be:

At Column 24, Line 43:
$Ar^a$ denotes phenyl optionally
Should be:
$Ar^3$ denotes phenyl optionally Signed and Sealed this
Twenty-third Day of May, 2017

Michelle K. Lee
*Director of the United States Patent and Trademark Office*

CERTIFICATE OF CORRECTION (continued)
U.S. Pat. No. 9,585,880 B2

At Column 27, Line 14:
$Ar^a$ denotes phenyl optionally
Should be:
$Ar^3$ denotes phenyl optionally At Column 45, Line 63:
cross-titrating GST-AKAP186
Should be:
cross-titrating GST-AKAP18δ

At Column 56, Line 15:
between AKAP186 and PLB
Should be:
between AKAP18δ and PLB At Column 67, Line 51, Claim 20:
$SO_3H$ $C_1$-$C_4$-alkyl
Should be:
$SO_3H$, $C_1$-$C_4$-alkyl